(12) United States Patent
Hirose

(10) Patent No.: US 6,584,847 B1
(45) Date of Patent: Jul. 1, 2003

(54) ULTRASONIC DETECTOR AND METHOD FOR ULTRASONIC DETECTION

(75) Inventor: Masayuki Hirose, Tokyo (JP)

(73) Assignee: H & B System Co., Ltd., Tokyo (JP)

( * ) Notice: Subject to any disclaimer, the term of this patent is extended or adjusted under 35 U.S.C. 154(b) by 0 days.

(21) Appl. No.: 09/926,108

(22) PCT Filed: Feb. 1, 2000

(86) PCT No.: PCT/JP00/00543

§ 371 (c)(1),
(2), (4) Date: Sep. 4, 2001

(87) PCT Pub. No.: WO00/52418

PCT Pub. Date: Sep. 8, 2000

(30) Foreign Application Priority Data

Mar. 1, 1999 (JP) .......................................... 11-053288

(51) Int. Cl.$^7$ .............................................. G01N 29/06

(52) U.S. Cl. .............................. 73/579; 73/597; 73/602; 73/628; 73/598

(58) Field of Search ........................ 73/579, 597, 598, 73/599, 600, 602, 628

(56) References Cited

U.S. PATENT DOCUMENTS

| 5,675,085 A | * | 10/1997 | Hayashi et al. | 73/628 |
| 5,786,535 A | * | 7/1998 | Takeuchi et al. | 73/624 |
| 5,841,019 A | * | 11/1998 | Drabrin et al. | 73/12.11 |
| 5,955,669 A | * | 9/1999 | Egami | 73/579 |
| 6,029,521 A | * | 2/2000 | Lin et al. | 73/597 |
| 6,119,526 A | * | 9/2000 | Reigstad et al. | 73/803 |
| 6,301,967 B1 | * | 10/2001 | Donskoy et al. | 73/579 |
| 6,378,375 B1 | * | 4/2002 | Kobayashi | 73/600 |

FOREIGN PATENT DOCUMENTS

| JP | 60-185106 | 9/1985 |
| JP | 61-204523 | 9/1986 |
| JP | 62-206480 | 9/1987 |
| JP | 63-11855 | 1/1988 |
| JP | 1-96584 | 4/1989 |
| JP | 4-283610 | 10/1992 |
| JP | 6-3137 | 1/1994 |
| JP | 9-61144 | 3/1997 |
| JP | 9-189599 | 7/1997 |
| JP | 9-264735 | 10/1997 |
| JP | 9-269215 | 10/1997 |
| JP | 10-62395 | 3/1998 |
| JP | 11-6879 | 1/1999 |

* cited by examiner

Primary Examiner—Helen Kwok
Assistant Examiner—Jacques Saint-Surin
(74) Attorney, Agent, or Firm—Oblon, Spivak, McClelland, Maier & Neustadt, P.C.

(57) ABSTRACT

While a transmitting transducer (2a) for transmitting an ultrasonic wave and a receiving transducer (2b) for receiving an ultrasonic wave are moved within a predetermined circular region (7) on a surface of a material being measured, ultrasonic waves are transmitted and received 10,000 times. Then, arithmetic averaging is performed every time an ultrasonic wave is received, on the ultrasonic wave and ultrasonic waves that have been received until then. For example, the aforementioned predetermined frequency is given by $((n\pm(\frac{1}{2}))\times(10^6\times v/\Delta L))(Hz)$, where $\Delta L$ is a variation in distance between the transmitting transducer and the receiving transducer, v is a transmission velocity of an ultrasonic wave transmitting in a material being detected, and n is a natural number. Consequently, it is possible to detect, with high accuracy, the thickness of a concrete material having a narrow width and a thick thickness, the thickness of the covering of a reinforcing bar and the diameter thereof, the depth of a crack and the like.

18 Claims, 70 Drawing Sheets

FIG.8
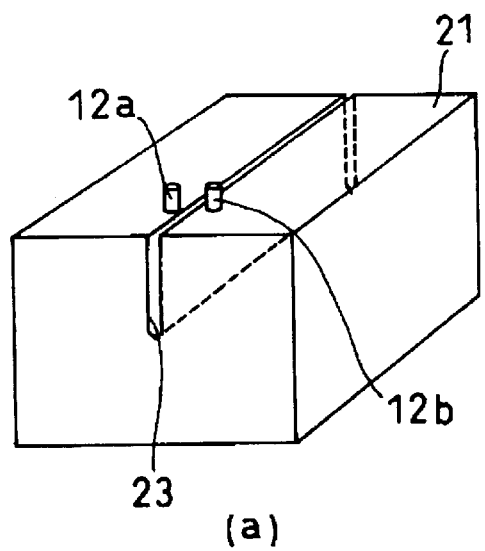
(a)
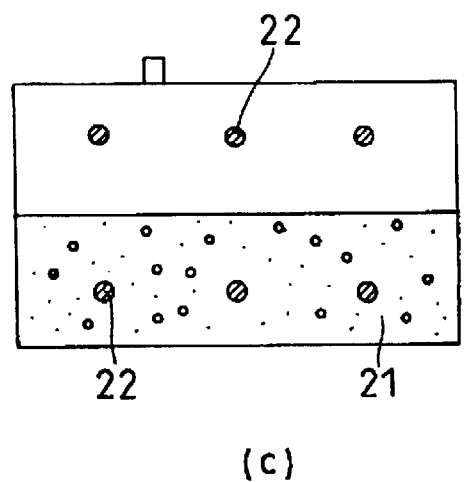
(c)
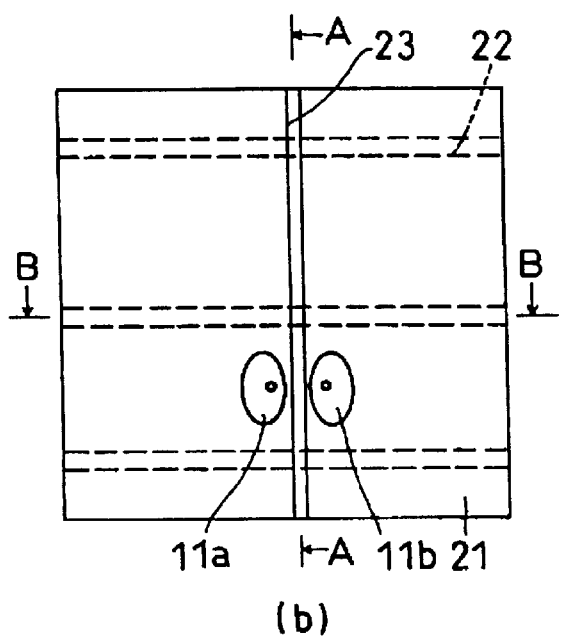
(b)
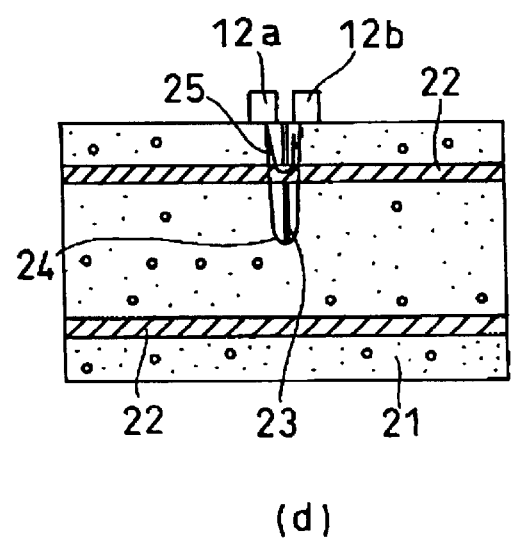
(d)

FIG.10
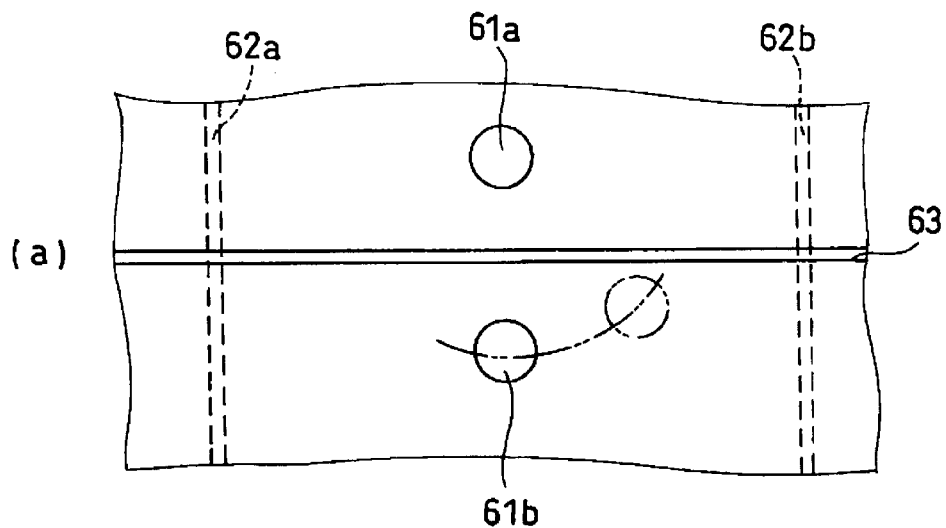
(a)
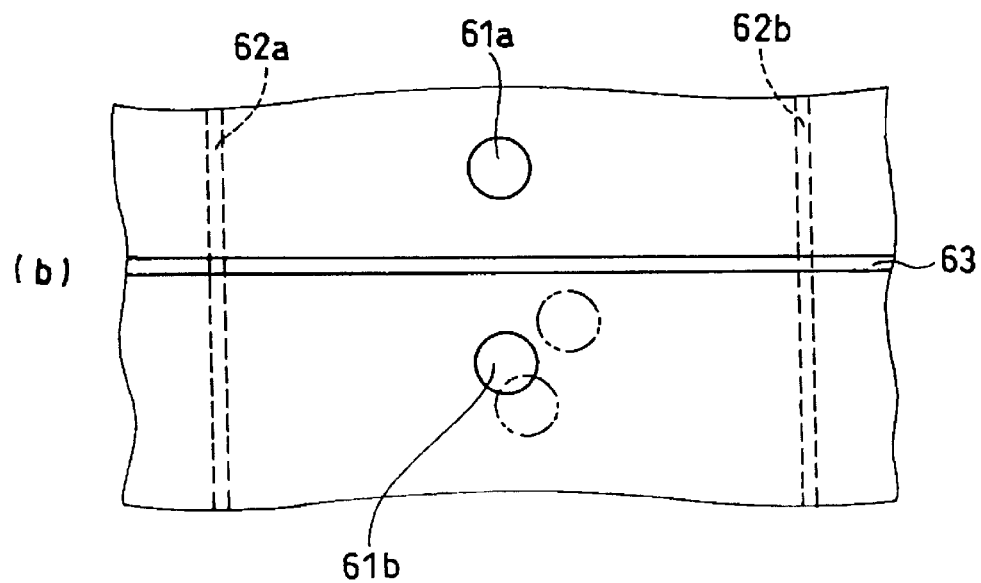
(b)

FIG.13
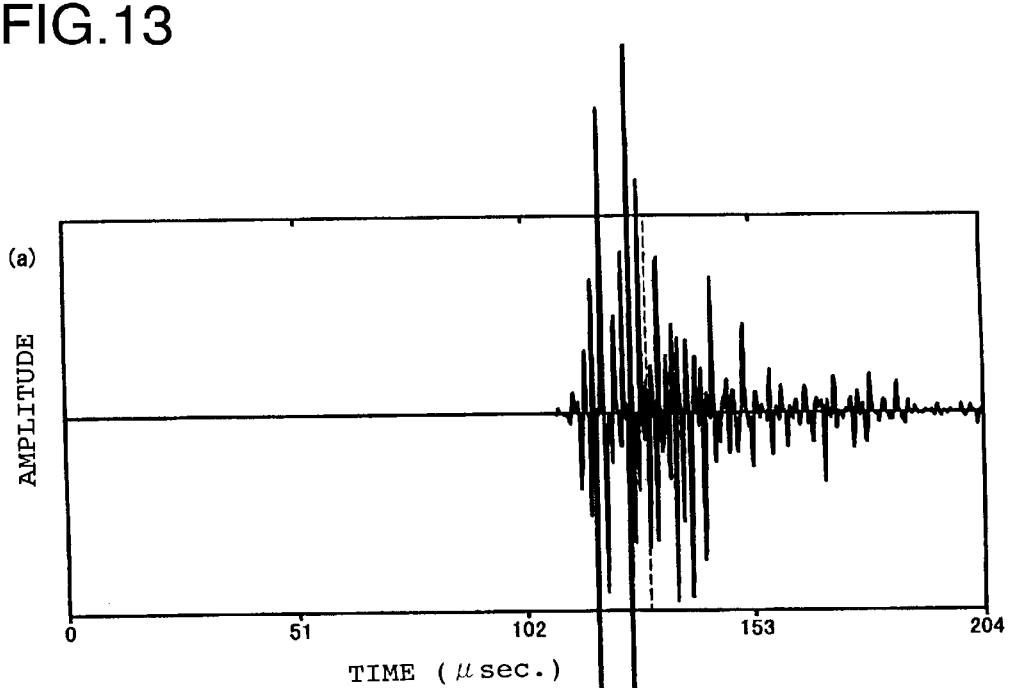
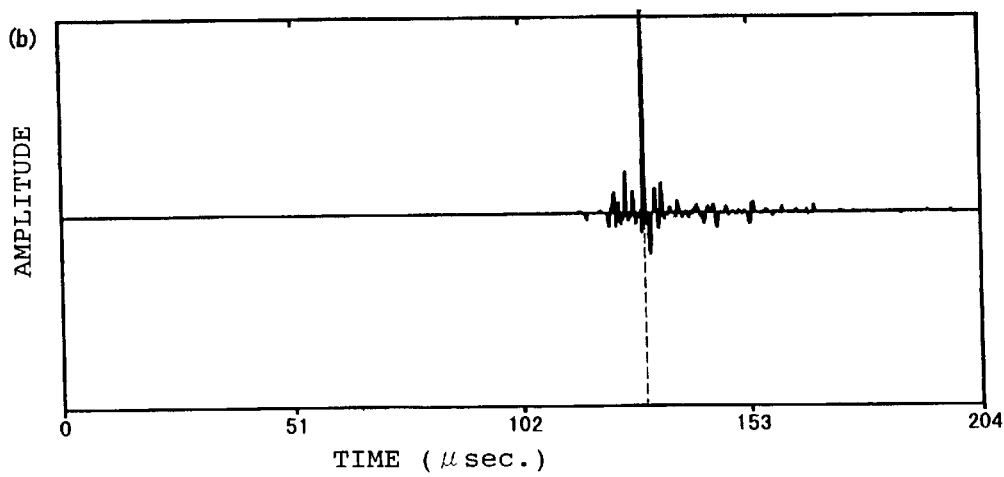

FIG.15
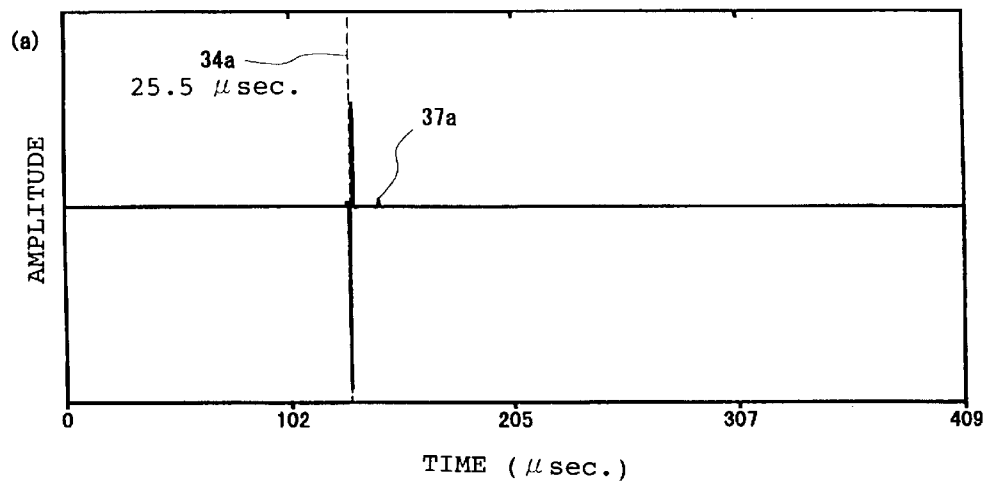
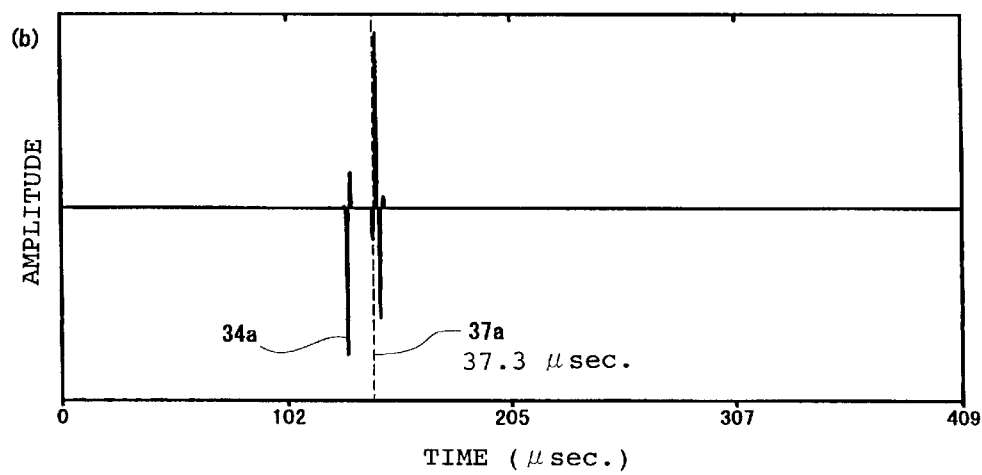

(a)         (b)

FIG.18
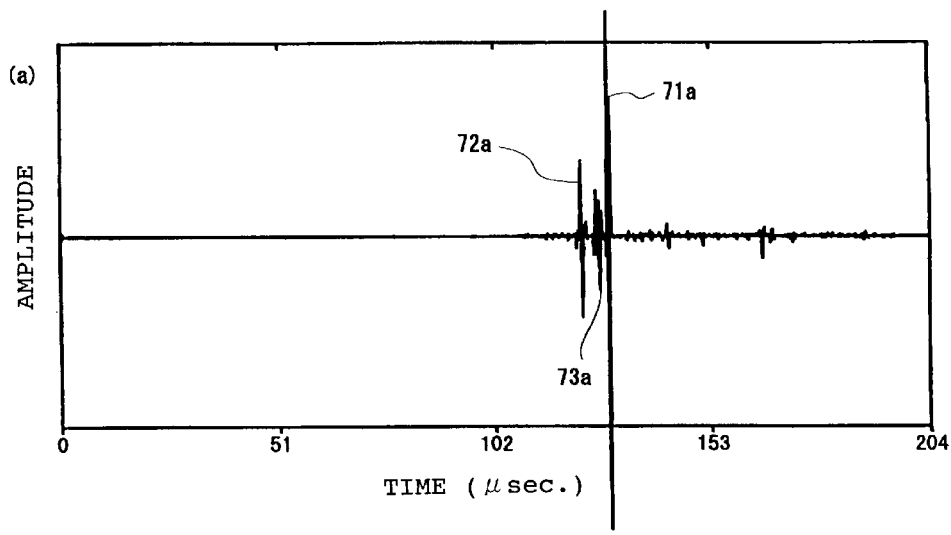
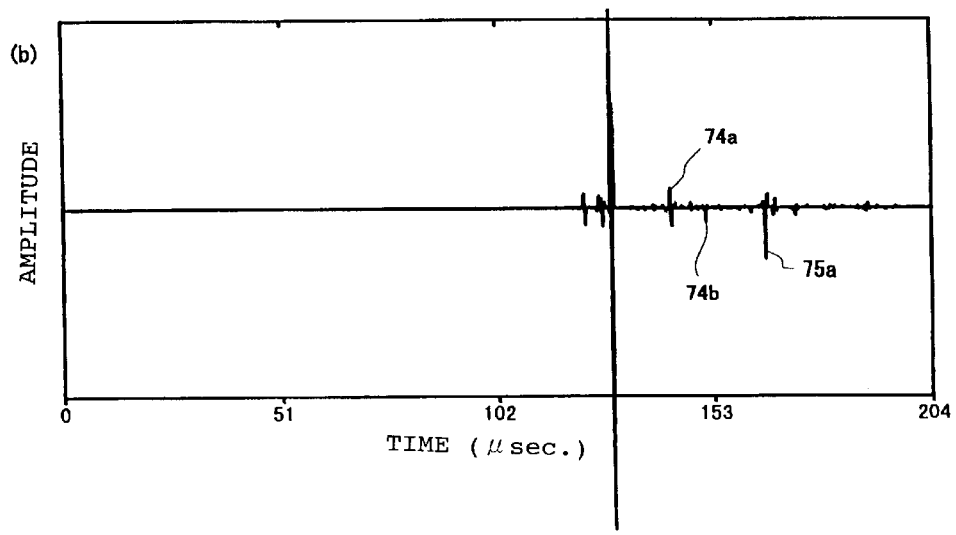

FIG.20
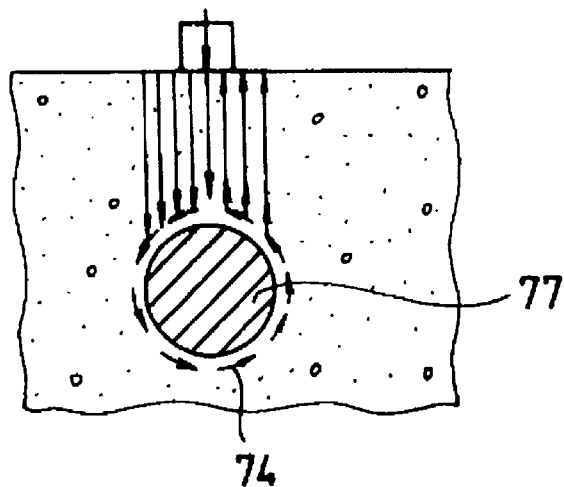
(a)
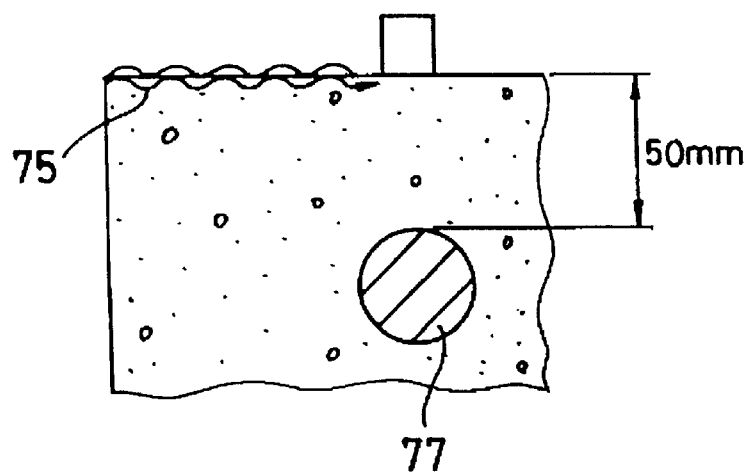
(b)

FIG.23
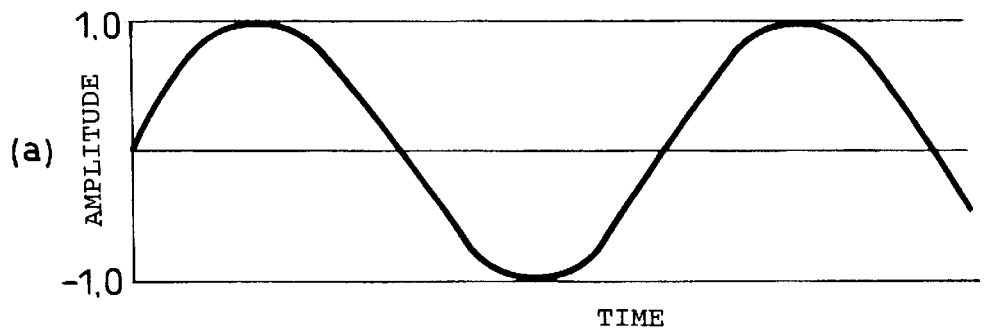
(a)
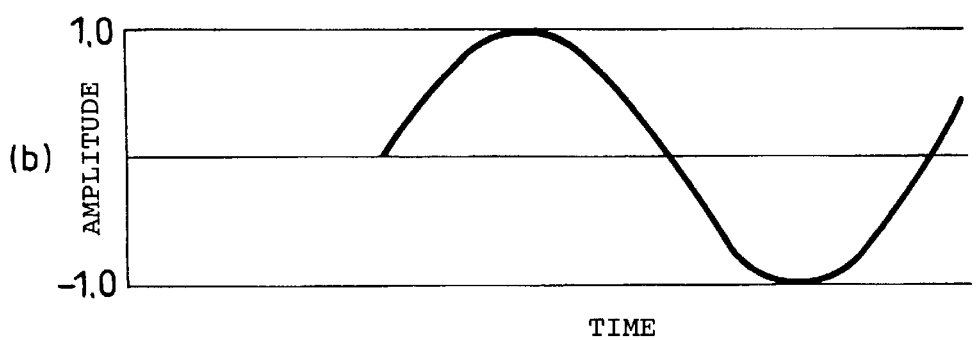
(b)
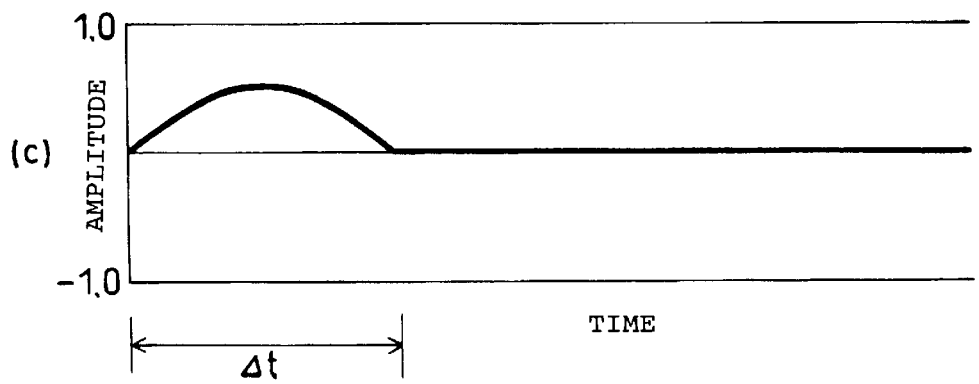
(c)

FIG.27
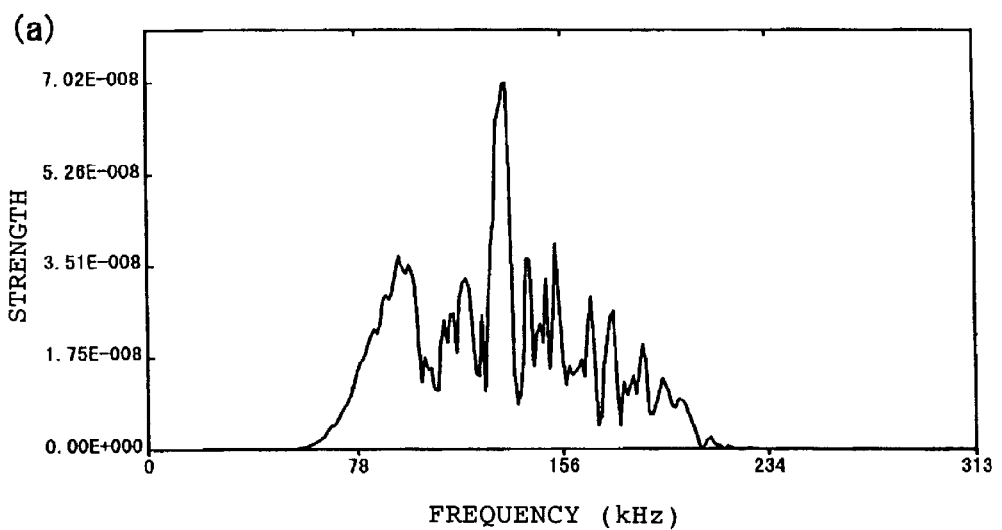
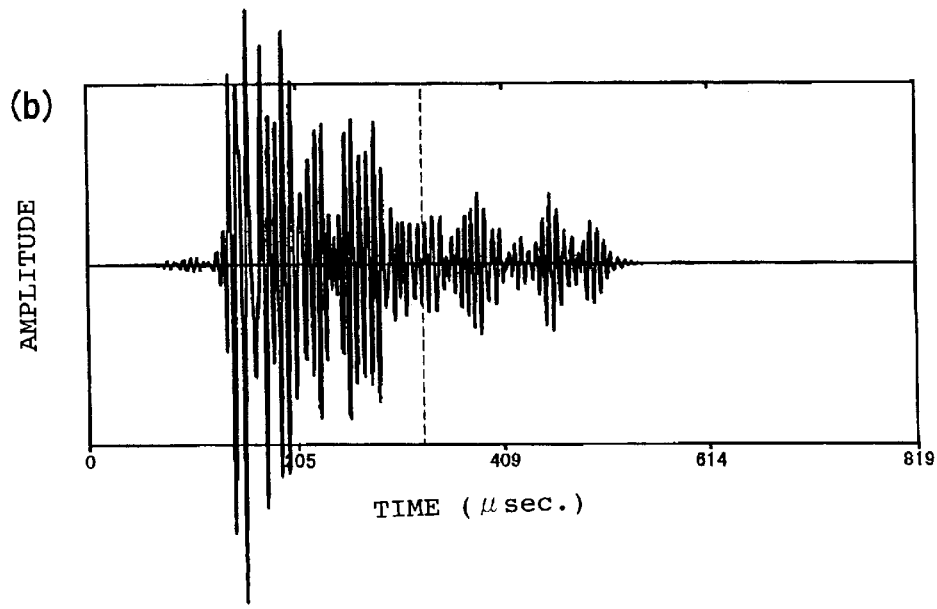

FIG.44
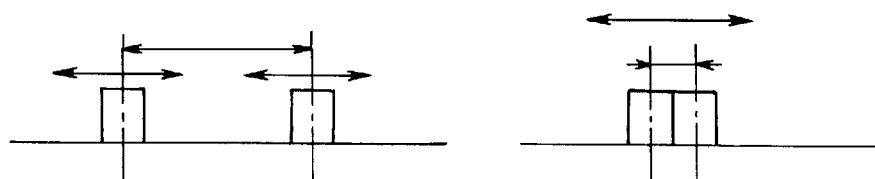
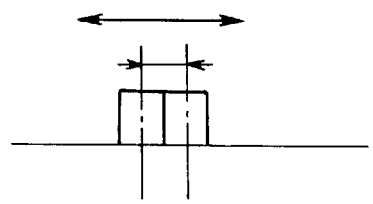
(a)  (b)
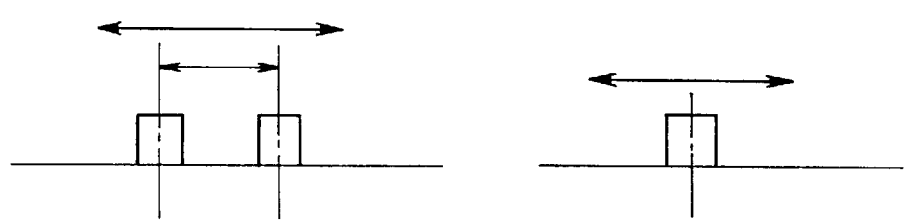
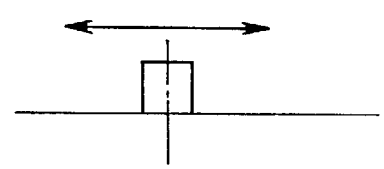
(c)  (d)

FIG.61
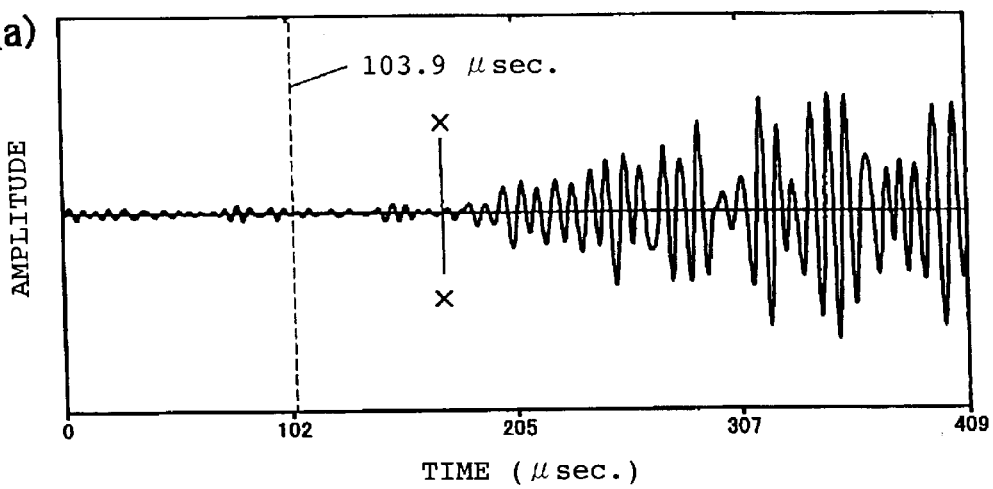
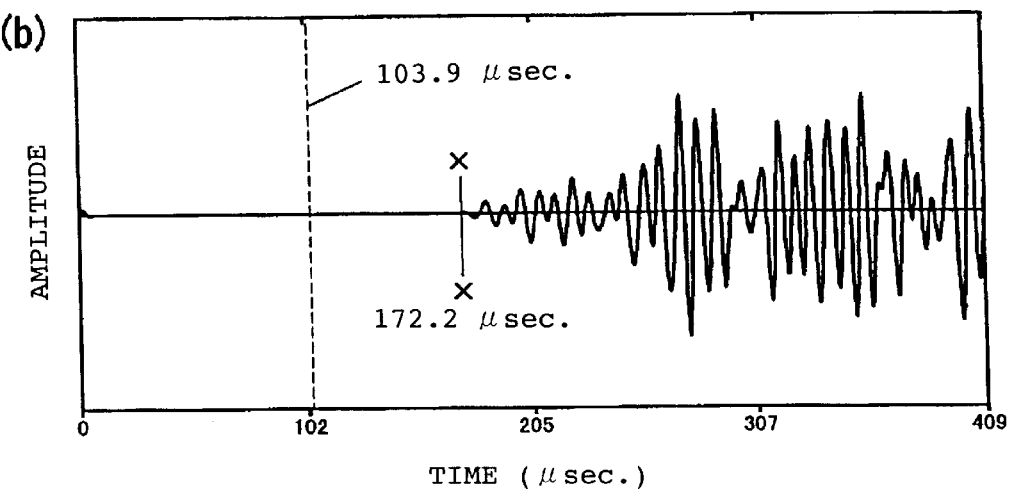

FIG.69
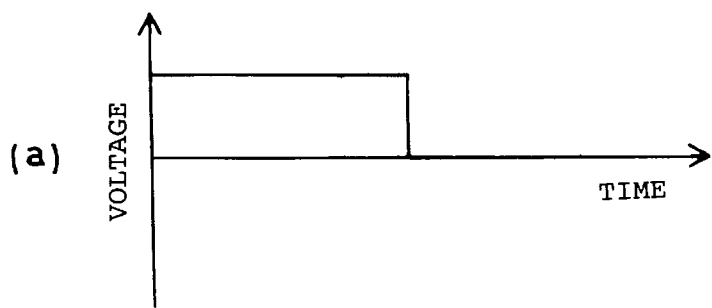
(a)
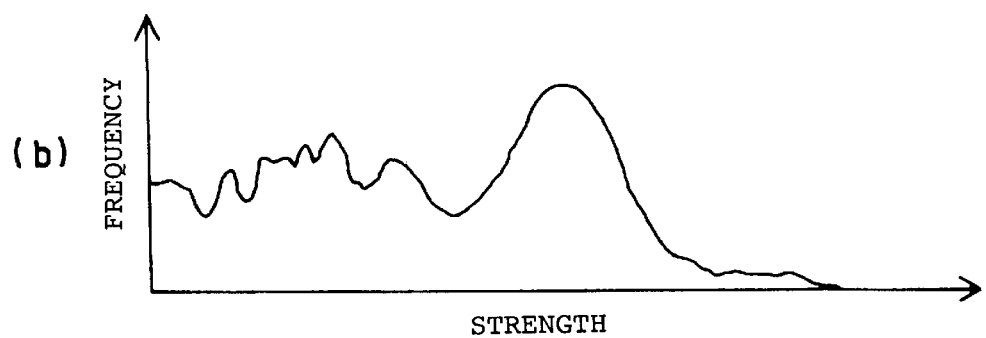
(b)
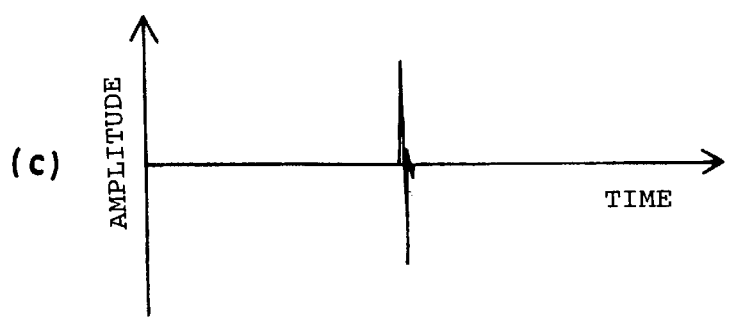
(c)

FIG.72
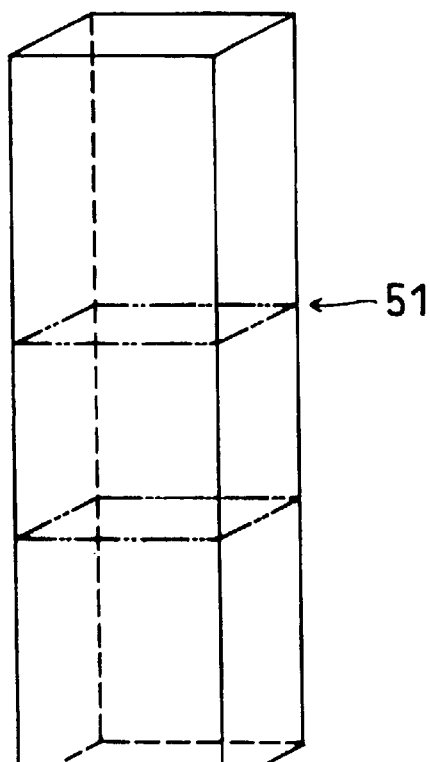
(a)
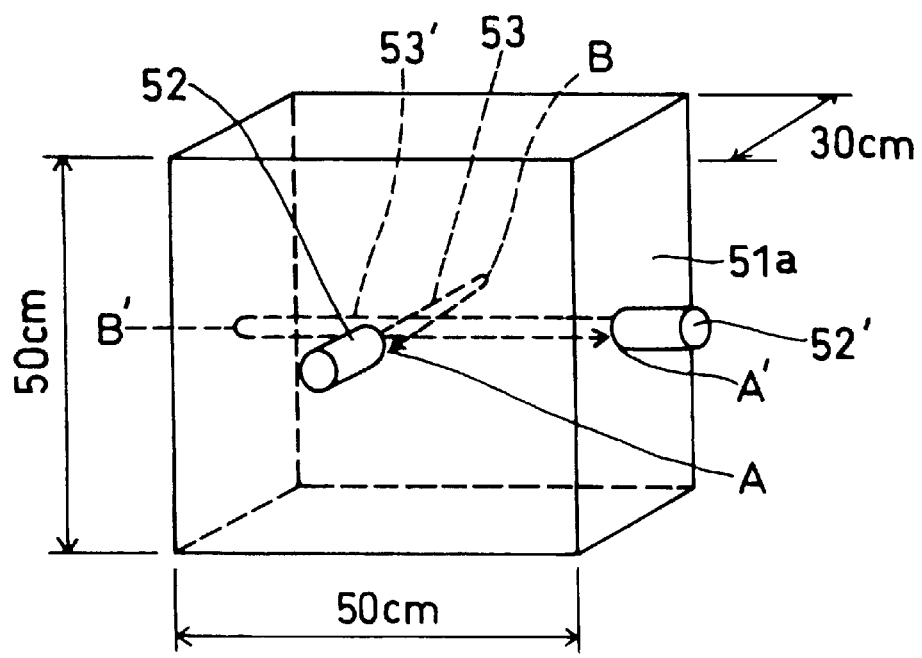
(b)

ULTRASONIC DETECTOR AND METHOD FOR ULTRASONIC DETECTION

TECHNICAL FIELD

The present invention relates to ultrasonic detection apparatuses to be employed such as for detecting internal defects or the like of concrete materials by means of ultrasonic waves and an ultrasonic detection method that employs the apparatus. More particularly, the present invention relates to an ultrasonic detection apparatus which provides accurate and high-speed detection of reinforcing bars arranged inside a concrete material, the depth of a crack, the thickness of concrete, gaps and the like, and to an ultrasonic detection method that employs the apparatus.

BACKGROUND OF ART

A concrete material is a composite structure of cement and coarse aggregates of 1 to 3 mm in diameter. Ultrasonic waves traveling through a concrete material are scattered while being reflected, refracted, and changed in mode repeatedly at the interface between the coarse aggregate and the cement.

This causes readily the ultrasonic waves to be diffused in the concrete material and significantly attenuated in strength in the orientation direction of the ultrasonic waves. The level of the attenuation would be acceleratingly increased as the ultrasonic waves have higher frequencies.

In addition, when longitudinal or transverse ultrasonic waves are input into a concrete material from a surface thereof, longitudinal or transverse ultrasonic waves and direct waves, each having a relatively large amount of energy, coexist with the longitudinal or transverse ultrasonic waves input to the inside of the concrete material. In addition, surface waves having a large amount of energy are generated at the surface of the concrete material.

These phenomena have conventionally made it difficult to detect the inside such as of a concrete material or a porous material by means of ultrasonic waves.

However, recent years have seen an improvement of internal detection methods employing ultrasonic waves. Thus, in some cases, with various conditions being satisfied, it is possible to measure the thickness of a concrete plate or detect gaps or the like therein within a detection depth range of about 20 to 50 cm. The conditions of the detection are shown below.

First, it is necessary to use ultrasonic wave transmitting and receiving transducers having a resonant frequency of about 100 to 500 kHz. Secondly, it is necessary to use transducers having an oscillator as large as about 50 to 70 mm in diameter. Thirdly, it is necessary to apply a stepped voltage to a ceramic oscillator or the like in the transducer instead of the pulsed voltage, which has been conventionally employed.

FIG. 68(*a*) is a graph showing a pulsed voltage, (b) being a graph showing the spectrum of the pulsed voltage, and (c) being a graph showing a time series waveform of the pulsed voltage. On the other hand, FIG. 69(*a*) is a graph showing a stepped voltage, (b) being a graph showing the spectrum of the stepped voltage, and (c) being a graph showing a time series waveform of the stepped voltage. The graphs represent pulsed and stepped voltages having values of 50 to 500V. Differences are found in the spectrum and time series waveform between the pulsed and stepped voltages. Incidentally, the peak frequencies of FIGS. 68(*b*) and 69(*b*) are resonant frequencies of oscillators, while FIGS. 68(*c*) and 69(*c*) show time series transmit ultrasonic waves.

Now, a conventional method for measuring a concrete material will be explained in which the stepped voltage shown in FIG. 69(*a*) is applied to the concrete material by using an ultrasonic transducer having an oscillator 56 mm in diameter whose resonant frequency is 1 MHz. FIG. 70 is a schematic view illustrating a concrete plate as a material to be detected. The concrete plate 41 as a material to be detected has a thickness of 20 cm and contains fine stones about 2 mm in diameter as coarse aggregate. In addition, the concrete plate 41 has a relatively small number of bubbles therein. Furthermore, it should be understood that this measuring method works as a method for making a measurement with one transducer, in which a transducer 42 functions as receiving and transmitting transducers. FIG. 71 is a graph illustrating a reflected wave obtained under the aforementioned conditions, with the horizontal axis representing the time and the vertical axis representing the amplitude.

Referring to FIG. 71, a peak 43*a* shows a longitudinal reflected wave 43 from the bottom surface of the concrete plate. The peak 43*a* is noticeable, showing that it is possible to measure the thickness of the concrete plate under the aforementioned conditions.

Suppose that like the concrete plate 41, the thickness is relatively thin when compared with the surface area. In this case, according to various types of measurement examples, since a corner-reflected wave 44 from a corner portion and a reflected wave of a surface wave 45 are generally small in amplitude, it is made possible to measure the thickness of a plate as thick as about down to 50 cm under the aforementioned conditions.

However, for a concrete plate having been subjected to aging, it is often difficult to confirm the generation of a reflected wave from the bottom surface thereof. Likewise, when a concrete plate is not a planar one, and great amounts of reflected waves from the corner portions and from surface waves are provided and lots of bubbles are contained in the concrete plate, it is also difficult in many cases to confirm the generation of a reflected wave from the bottom surface.

For example, the following cases make it difficult to measure thickness. FIG. 72 is a view illustrating a concrete pillar or a material to be detected, (a) being a schematic view thereof before being cut apart and (b) being a schematic view thereof after having been cut apart.

Here, such a concrete pillar 51 was made that has a side of length 30 cm and another side of length 50 cm in a cross section perpendicular to the longitudinal direction. Inside the concrete pillar 51, there is present a large number of bubbles about 1 to 10 mm in diameter. In addition, contained in the concrete pillar are 30 wt % of coarse aggregates having diameters greater than 5 mm and less than 1 cm, 40 wt % of coarse aggregates having diameters greater than 1 cm and less than 2 cm, and 40 wt % of coarse aggregates having diameters greater than 2 cm. In addition, a concrete material 51*a* having a height of 50 cm was cut from the concrete pillar 51.

Such a case is explained below in which a transducer 52 is placed at the center A of a plane having a width of 50 cm for measuring the thickness. FIG. 73 is a schematic view illustrating waves produced when the thickness is measured with the transducer 52 being placed at the center A.

When longitudinal ultrasonic waves are input into the concrete material 51*a* from a surface thereof directly downwards with the transducer 52 being placed at the center A, as shown in FIG. 73, a corner-reflected wave 54, a direct wave 55, a surface wave 56, and a longitudinal wave 57 low in strength as well as a reflected wave 53 from the bottom surface return to the center A. Accordingly, the received wave at the center A is a superimposed wave of the waves 53–57, making it difficult to determine the peak of the reflected wave from the bottom surface as shown in FIG. 71.

Various types of oscillators were actually used for the application of a stepped voltage of 500V for measurement, with the results being illustrated. FIG. 74(a) is a graph illustrating a time series waveform obtained by a measurement with a transmitting transducer having an oscillator of resonant frequency 2.5 MHz and 20 mm in diameter, (b) being a graph illustrating a time series waveform obtained by a measurement with a transmitting transducer having an oscillator of resonant frequency 500 kHz and 40 mm in diameter, and (c) being a graph illustrating a time series waveform obtained by a measurement with a transmitting transducer having an oscillator of resonant frequency 500 kHz and 70 mm in diameter. Incidentally, the receiving transducer employed an oscillator having a resonant frequency of 2.5 MHz and a diameter of 20 mm. Referring to FIGS. 74(a) through (c), ultrasonic waves are transmitted at time 104 μs on the horizontal axis. For example, time 205 μs in the figures shows that 101 μs have elapsed after the time of transmission.

For these measurements, a two-transducer method was employed in which a transmitting transducer and a receiving transducer are arranged extremely close to each other. Referring to FIGS. 74(a) through (c), the time shown by the dashed lines indicates the theoretical time of generation of the reflected wave 53 from the bottom surface of the concrete material 51a. However, in these time series waveforms, it is impossible to identify the time as the time of generation of the reflected wave 53. Therefore, in such cases, it is impossible to measure the thickness of the concrete material 51a.

The present invention was developed in view of such problems. It is an object of the present invention to provide an ultrasonic detection apparatus which can detect with accuracy the thickness of a concrete material having a narrow width and a thick thickness, the thickness of the covering of a reinforcing bar and the diameter thereof, the depth of a crack and the like, and a ultrasonic detection method that employs the apparatus.

DISCLOSURE OF THE INVENTION

A first ultrasonic detection apparatus according to the present invention is for allowing a transmitting transducer to transmit an ultrasonic wave a plurality of times to analyze an ultrasonic wave received by a receiving transducer. The ultrasonic detection apparatus comprises: an arithmetic averaging device which performs arithmetic averaging a plurality of times per one detection every time an ultrasonic wave is received, on the ultrasonic wave and ultrasonic waves having been received until then; and extracting means which extracts an ultrasonic wave having a predetermined frequency as a center frequency from received ultrasonic waves. The abovementioned predetermined frequency is given by $((n\pm(\frac{1}{2}))(10^6 \times v\Delta L))$(Hz), where $\Delta L$ is a variation in distance between the abovementioned transmitting transducer and the abovementioned receiving transducer, v is a transmission velocity of an ultrasonic wave transmitting in a material being detected, and n is a natural number.

The present invention allows the arithmetic averaging device to perform arithmetic averaging 1,000 times or more per one detection every time an ultrasonic wave is received, on the ultrasonic wave and the ultrasonic waves that have been received until then. This causes waves having variations in phase to gradually cancel out each other and only those waves having substantially no variation in phase to amplify each other to remain. Accordingly, measurements carried out under the conditions which cause substantially no change in phase of a desired wave would make it possible to detect, with high accuracy, the thickness of a concrete material narrow in width and thick in thickness or the like. Furthermore, the arithmetic averaging device performs directly the arithmetic averaging, thereby reducing the amount of processing to be performed by purpose-oriented software or the like and making it possible to perform processing at high speeds. For example, suppose that arithmetic averaging needs to be performed 10,000 times, in which the arithmetic averaging device performs arithmetic averaging up to 4,000 times and the software performs subsequent arithmetic averaging. In this case, arithmetic means obtained by performing arithmetic averaging 4,000 times, another 4,000 times, and further 2,000 times are processed by the arithmetic averaging device, and then the resulting values are processed by the software.

A second ultrasonic detection apparatus according to the present invention is for allowing a transmitting transducer to transmit an ultrasonic wave a plurality of times to analyze an ultrasonic wave received by a receiving transducer. The ultrasonic detection apparatus comprises an arithmetic averaging device which performs arithmetic averaging a plurality of times per one detection every time an ultrasonic wave obtained by applying a step function voltage to an oscillator is received, on the ultrasonic wave and ultrasonic waves having been received until then. The abovementioned predetermined frequency is given by $((n\pm(\frac{1}{2}))\times(10^6 \times v/\Delta L))$ (Hz), where $\Delta L$ is a variation in distance between the abovementioned transmitting transducer and the abovementioned receiving transducer, v is a transmission velocity of an ultrasonic wave transmitting in a material being detected, and n is a natural number.

A third ultrasonic detection apparatus according to the present invention is for allowing a transmitting transducer to transmit an ultrasonic wave a plurality of times to analyze an ultrasonic wave received by a receiving transducer. The ultrasonic detection apparatus comprises: an arithmetic averaging device for performing arithmetic averaging a plurality of times per one detection, every time an ultrasonic wave obtained by applying a step function voltage to an oscillator is received, on the ultrasonic wave and ultrasonic waves having been received until then; and extracting means which extracts an ultrasonic wave having a predetermined frequency as a center frequency from received ultrasonic waves. The abovementioned predetermined frequency is given by $((n\pm(\frac{1}{2}(10^6 \times v/66 L))(Hz)$, where $\Delta L$ is a variation in distance between the abovementioned transmitting transducer and the abovementioned receiving transducer, v is a transmission velocity of an ultrasonic wave transmitting in a material being detected, and n is a natural number.

A first method for detecting an ultrasonic wave according to the present invention comprises the steps of: transmitting and receiving an ultrasonic wave a plurality of times while a transmitting transducer for transmitting ultrasonic waves and a receiving transducer for receiving ultrasonic waves are moved within a predetermined region on a surface of a material being detected; performing arithmetic averaging every time the ultrasonic wave is received, on the ultrasonic wave and ultrasonic waves having been received until then; and extracting an ultrasonic wave having a predetermined frequency as a center frequency from ultrasonic waves obtained by the arithmetic averaging. The abovementioned predetermined frequency is given by $((n\pm(½))\times(10^6\times v/\Delta L))$ (Hz), where $\Delta L$ is a variation in distance between the abovementioned transmitting transducer and the abovementioned receiving transducer, v is a transmission velocity of an ultrasonic wave transmitting in a material being detected, and n is a natural number.

The present invention allows ultrasonic waves to be transmitted and received a plurality of times while a transmitting transducer for transmitting an ultrasonic wave and a receiving transducer for receiving an ultrasonic wave are moved within a predetermined region on a surface of a material being detected, thereby causing a received wave having variations in phase and a received wave having no variation in phase to exist. In addition, arithmetic averaging is performed, every time an ultrasonic wave is received, on the ultrasonic wave and ultrasonic waves that have been received until then. This makes it possible to allow received waves varied in phase to gradually vanish and only those waves not varied in phase to remain. This makes it possible to vanish unnecessary received waves to extract only desired received waves.

A second method for detecting an ultrasonic wave according to the present invention comprises the steps of: transmitting and receiving an ultrasonic wave a plurality of times while a transmitting-receiving transducer for transmitting and receiving ultrasonic waves is moved within a predetermined region on a surface of a material being detected; performing arithmetic averaging every time the ultrasonic wave is received, on the ultrasonic wave and ultrasonic waves having been received until then; and extracting an ultrasonic wave having a predetermined frequency as a center frequency from ultrasonic waves obtained by the arithmetic averaging. The abovementioned predetermined frequency is given by $((n\pm(½(10^6\times v/\Delta L))(Hz)$, where $\Delta L$ is a variation in distance between the abovementioned transmitting transducer and the abovementioned receiving transducer, v is a transmission velocity of an ultrasonic wave transmitting in a material being detected, and n is a natural number.

A third method for detecting an ultrasonic wave according to the present invention comprises the step of repeating a predetermined number of times the steps of: transmitting and receiving an ultrasonic wave a plurality of times while a transmitting transducer for transmitting ultrasonic waves and a receiving transducer for receiving ultrasonic waves, evenly spaced apart from each other, are moved within a predetermined region on a surface of a material being detected; performing arithmetic averaging every time the ultrasonic wave is received, on the ultrasonic wave and ultrasonic waves having been received until then; and varying a distance between the abovementioned transmitting transducer and the abovementioned receiving transducer by a predetermined amount. The method further comprises the steps of; determining an arithmetic mean of ultrasonic waves obtained as results of the arithmetic averaging; and extracting an ultrasonic wave having a predetermined frequency as a center frequency from ultrasonic waves obtained by the last arithmetic averaging. The abovementioned predetermined frequency is given by $((n\pm(½(10^6\times v/\Delta L))(Hz)$, where $\Delta L$ is a variation in distance between the abovementioned transmitting transducer and the abovementioned receiving transducer, v is a transmission velocity of an ultrasonic wave transmitting in a material being detected, and n is a natural number.

A fourth method for detecting an ultrasonic wave according to the present invention comprises the step of repeating the steps of: transmitting and receiving an ultrasonic wave a plurality of times while a transmitting transducer and a receiving transducer are evenly spaced apart from each other, the transmitting transducer transmitting ultrasonic waves by receiving an electrical signal to be output from a transmitting circuit, and the receiving transducer receiving ultrasonic waves to input an electrical signal to a receiving circuit disposed in a housing different from one for the transmitting circuit; performing arithmetic averaging every time the ultrasonic wave is received, on the ultrasonic wave and ultrasonic waves having been received until then; extracting an ultrasonic wave having a predetermined frequency as a center frequency from ultrasonic waves obtained by the arithmetic averaging; and moving the transmitting transducer and the receiving transducer on a surface of a material being detected. The abovementioned predetermined frequency is given by $((n\pm(½)\times(10^6\times v/\Delta L))(Hz)$, where $\Delta L$ is a variation in distance between the abovementioned transmitting transducer and the abovementioned receiving transducer, v is a transmission velocity of an ultrasonic wave transmitting in a material being detected, and n is a natural number.

BRIEF DESCRIPTION OF THE DRAWINGS

FIG. 8 is a view illustrating a material to be detected which is employed in an example of measurement of the depth of a crack, (a) being a perspective view, (b) being a plan view, (c) being a cross-sectional view taken along line A—A of (b), and (d) being a cross-sectional view taken along line B—B of (b).

FIGS. 10(*a*) and (*b*) are schematic views illustrating a method for moving one transducer.

FIGS. 13(*a*) and (*b*) are graphs illustrating time series waveforms resulted from the measurement of the depth of a deformed reinforcing bar.

FIGS. 15(a) and (b) are graphs illustrating time series waveforms corresponding to the spectra shown in FIG. 14.

FIGS. 18(a) and (b) are graphs illustrating time series waveforms obtained from a concrete material having no cracks formed thereon.

FIG. 20 is also a schematic view illustrating the transmission path of ultrasonic waves in a concrete material having no crack formed therein.

FIG. 23 is a view of an arithmetic mean $y_{Dk}(t)$, an arithmetic mean $y_{Dk+1}(t)$, and their arithmetic mean when a given frequency component is shifted by one-half cycle between the arithmetic mean $y_{Dk}(t)$ and the arithmetic mean $y_{Dk+1}(t)$, (a) being a schematic view illustrating the arithmetic mean $y_{Dk}(t)$, (b) being a schematic view illustrating the arithmetic mean $y_{Dk+1}(t)$, and (c) being a schematic view illustrating their arithmetic mean $_{f/2} y_{ave}(t)$.

FIG. 27 is a view illustrating a wave obtained with the center frequency being at 130 kHz, (a) being a graph illustrating a Fourier spectrum and (b) being a graph illustrating a time series waveform.

FIGS. 44(a) through (d) are schematic views illustrating various methods for scanning a transducer without using a measurement tool.

FIG. 61 is a view illustrating waves received at measurement position P28, (a) being a graph illustrating a case where no electrical noise nor disturbance has been eliminated and (b) being a graph illustrating a case where they have been eliminated.

FIG. 69(a) is a graph showing a stepped voltage, (b) being a graph showing the spectrum of the stepped voltage, and (c) being a graph showing a time series waveform of the stepped voltage.

FIG. 72 is a view illustrating a concrete pillar as a material to be detected, (a) being a schematic view thereof before being cut apart and (b) being a schematic view thereof after having been cut apart.

BEST MODE FOR CARRYING OUT THE INVENTION

Now, an ultrasonic detection apparatus according to embodiments of the present invention will be specifically explained below with reference to the accompanying drawings.

Figure 1:
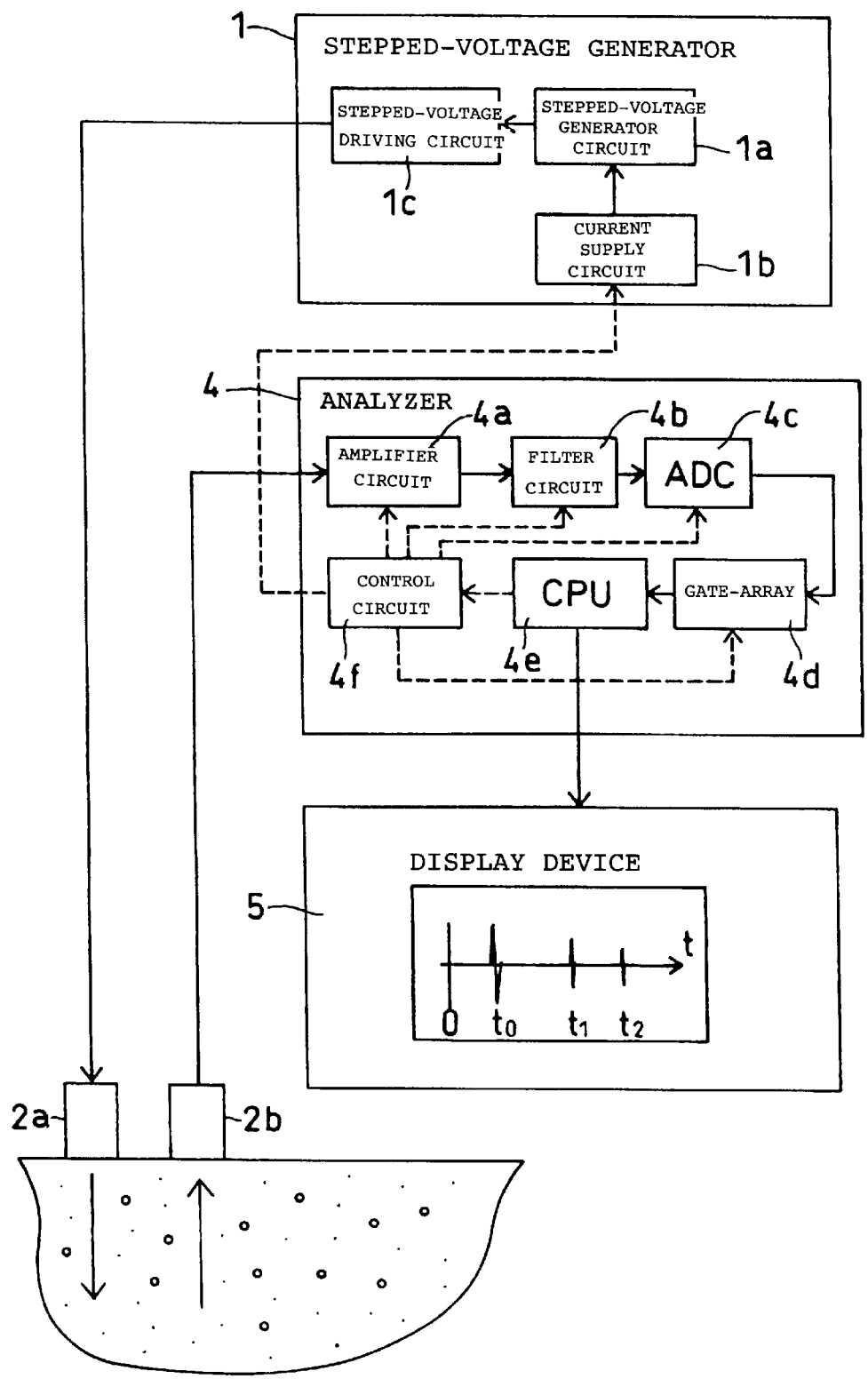
FIG. 1 is a block diagram illustrating an ultrasonic detection apparatus according to an embodiment of the present invention.

FIG. 1 is a block diagram illustrating an ultrasonic detection apparatus according to an embodiment of the present invention.

The ultrasonic detection apparatus according to this embodiment of the present invention is provided with a stepped-voltage generator 1 for applying a stepped voltage outwardly, a transmitting transducer 2a for receiving a stepped voltage applied by the stepped-voltage generator 1 to transmit ultrasonic waves to a material to be detected, and a receiving transducer 2b for receiving a reflected wave or the like from the interior of the material being detected. The ultrasonic detection apparatus is also provided with an analyzer 4 for analyzing an electrical signal provided by the receiving transducer 2b, and a display device 5 for displaying the result of analysis provided by the analyzer 4 and the waveform of a stepped voltage generated by the stepped-voltage generator 1.

The stepped-voltage generator 1 is provided with a stepped-voltage generator circuit 1a for generating a stepped voltage, a current supply circuit 1b for supplying a current to the stepped-voltage generator circuit 1a at controlled intervals, and a stepped-voltage driving circuit 1c for feeding the stepped voltage to outside the stepped-voltage generator 1. Incidentally, for example, the stepped-voltage generator 1 generates a stepped voltage of 500V.

Furthermore, the analyzer 4 is provided with an amplifier circuit 4a for amplifying an electrical signal received, a filter circuit 4b for filtering the amplified signal, an analog-to-digital converter (ADC) 4c for converting the filtered signal, a gate-array (arithmetic averaging device) 4d, and a central processing unit (CPU) 4e. The gate-array 4d performs arithmetic averaging on received waves every time a wave is received.

The analyzer 4 is further provided with a control circuit 4f, which controls the interval of current supply by the current supply circuit 1b, the range of amplification by the amplifier circuit 4a, the operation of the filter circuit 4b, the recording interval and the record data length of the ADC 4c, and the number of times of addition by the gate-array 4d. Incidentally, the control circuit 4f is controlled by the CPU 4e or an external notebook-type personal computer.

Figure 2:
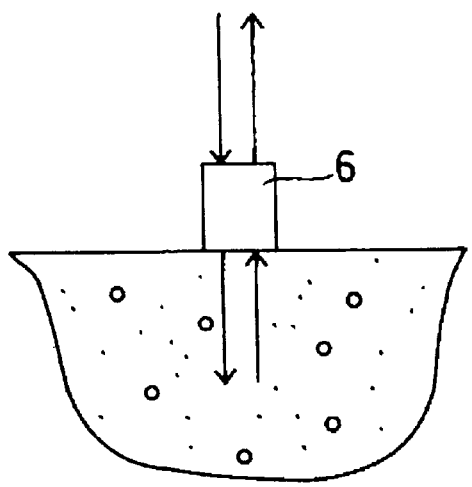
FIG. 2 is a schematic view illustrating an embodiment that employs a one-transducer method.

Incidentally, the ultrasonic detection apparatus according to this embodiment shown in FIG. 1 is expressed with the two-transducer method; however, the one-transducer method may be employed. FIG. 2 is a schematic view illustrating an embodiment that employs the one-transducer method. In this case, one transducer 6 functions as transmitting and receiving transducers.

In addition, in detecting the thickness of a porous material such as a concrete material or in detecting a reinforcing bar, ultrasonic waves are significantly attenuated in the material and thus tend to provide feeble reflected waves from a detected target, which are included in received waves. For this reason, it is preferable to design an ultrasonic detection apparatus so as to prevent electrical noise, or among other things, standing noise from entering the ultrasonic detection apparatus as much as possible.

In this regard, it is preferable to extremely reduce the voltage generator circuit 1a and the voltage driving circuit 1c in the stepped-voltage generator 1 to a size enough to be placed on-board, thereby incorporating the circuits not into the stepped-voltage generator 1 but into the transmitting transducer 2a. This prevents electrical noise from entering the analyzer 4 at the time of high-voltage drive.

Furthermore, waves that are received by the receiving transducer 2b and converted into an electrical signal (voltage) is feeble. For this reason, the electrical noise entering between the transmitting transducer 2a and the analyzer 4 has a significant effect on the S/N ratio of the wave received.

In this regard, it is preferable to extremely reduce the amplifier circuit 4a in the analyzer 4 to a size enough to be placed on-board, thereby incorporating the circuit not into the analyzer 4 but into the receiving transducer 2b.

As described above, to obtain further improved measurement accuracy, it is preferable to incorporate the voltage generator circuit 1a and the voltage driving circuit 1c into the transmitting transducer 2a, and the amplifier circuit 4a into the receiving transducer 2b.

Now, described is a method according to a first embodiment of the present invention, which employs the aforementioned detection apparatus. The first embodiment method allows the pair of the transmitting transducer 2a and the receiving transducer 2b to move arbitrarily within a circular region having a radius of 5 to 7 cm with center at center A in FIG. 72(b).

Figure 3:
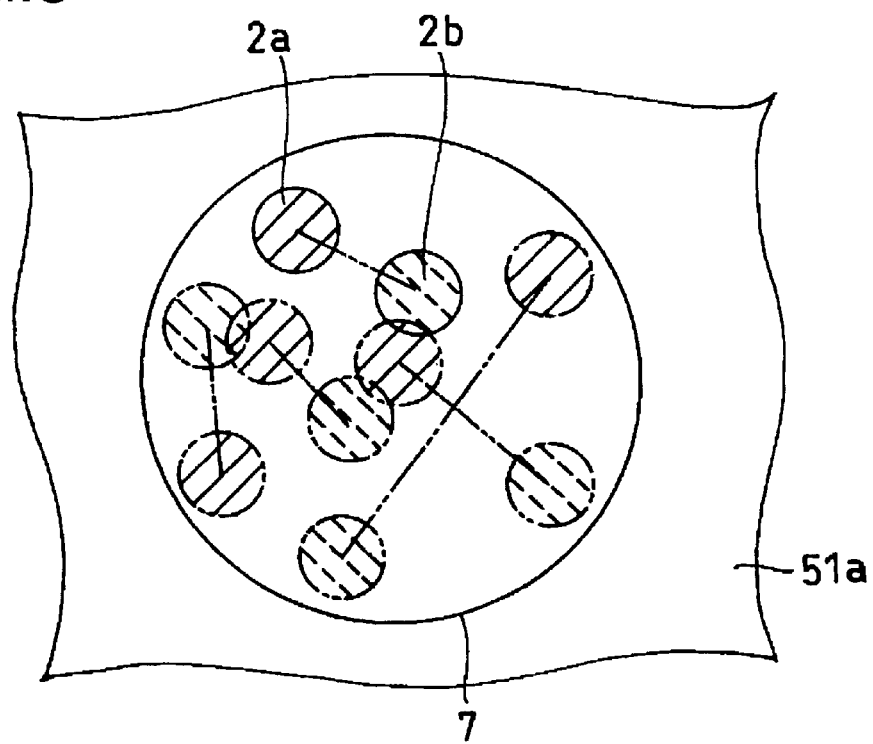
FIG. 3 is a schematic view illustrating the positional relationship between a transmitting transducer and a receiving transducer in the method according to a first embodiment method of the present invention.

FIG. 3 is a schematic view illustrating the positional relationship between a transmitting transducer and a receiving transducer in the method according to the first embodiment of the present invention. Incidentally, in FIG. 3, the transmitting transducer 2a having a diameter of 20 mm is hatched with solid lines, while the receiving transducer 2b having a diameter of 20 mm is hatched with dashed lines. In addition, a pair of transducers connected to each other with a chain double-dashed line indicates each transducer at a moment.

The first embodiment method employs the ultrasonic detection apparatus shown in FIG. 1 and performs measurements a large number of times, for example, 10,000 times while allowing the position of each of the transducers 2a and 2b to be varied within a predetermined circular region 7 as shown in FIG. 3. At this time, the receive and transmit faces of the transducers 2a and 2b each have to be always in contact with a surface of the concrete material 51a. Thus, it is necessary to apply oil or the like in advance as an ultrasonic wave transmitting medium to measurement regions.

When the thickness of the concrete material 51a is measured by this embodiment method, the transmission distance of the corner-reflected wave 54, the direct wave 55, the surface wave 56, and the feeble longitudinal wave 57 low in strength varies as the position of each of the transducers 2a and 2b varies. On the other hand, if the distance is sufficiently short between the transmitting transducer 2a and the receiving transducer 2b, it is possible to assume that the path length of the reflected wave 53 from the bottom surface of the concrete material 51a as a detected target will not vary.

Thus, although the phase of the waves 54–57 varies every time the position of each of the transducers 2a and 2b varies, the phase of the reflected wave 53 will not vary. Even with a variation in phase of the reflected wave 53, the amount of the variation is negligible in low-frequency ultrasonic waves. Accordingly, as shown in FIG. 3, arithmetic averaging may be performed on a number of measurements after receive waves $\omega_i(t)$ have been obtained by making the measurements while the position of each of the transducers 2a and 2b is being varied, thereby reducing the amplitude contributed to by the waves 54–57 and increasing the amplitude of the reflected wave 53 as a detected target. Accordingly, it can be readily possible to recognize the generation of the reflected wave 53. Incidentally, though not shown in the drawings, a number of scattered waves are also included in the waves received. These scattered waves are generated in a non-standing manner with respect to the position of the transducer, thereby allowing the arithmetic averaging to eliminate the scattered waves. M-time arithmetic averaging is expressed by the following equation 1.

$$y(t) = \frac{1}{m} \sum_{i=1}^{m} \omega_i(t) \tag{1}$$

Incidentally, about 10 to 1000 times of measurements are not enough to sufficiently reduce the amplitude of the waves 54–57. Thus, it is difficult to recognize the generation of the reflected wave 53. Many measurements show that it is necessary to make about 1,000 times or more of measurements. Thus, it is necessary to measure the thickness such as of a concrete pillar or a beam material by performing arithmetic averaging on such an enormous number of measurement waves, and this calculation is preferably carried out as fast as possible.

In this regard, this exemplary method employs the gate-array 4d to perform the aforementioned arithmetic averaging by the control of the CPU 4e or an external notebook-type personal computer. In this case, the stepped-voltage generator 1 is allowed to apply a stepped voltage to the transmitting transducer at any interval of 1.5–10 ms intervals. Then, each of the transducers 2a and 2b is moved to perform arithmetic averaging every time a wave is received while the stepped voltage is applied, for example, 10,000 times.

Incidentally, for example, the time required to perform arithmetic averaging 10,000 times during the application of the stepped voltage at 1.5 ms intervals is only about 15 seconds, which is sufficiently practical. In addition, it is more preferable to perform the arithmetic averaging in a shorter time. Accordingly, every predetermined number of times, for example, 1,000 times, a waveform indicative of the arithmetic mean at that point may be displayed on the display device 5 to allow the operator to recognize the generation of a reflected wave from the detected target. The operator may be thereby allowed to determine to terminate the measurement and the calculation of the arithmetic averaging.

Now, explained is the measurement result obtained by performing arithmetic averaging 10,000 times using a transmitting transducer having a resonant frequency of 2.5 MHz or 500 kHz. Here, the oscillator of the transmitting transducer is 20 mm in diameter for a resonant frequency of 2.5 MHz and is 40 mm or 70 mm for a resonant frequency of 500 kHz, while the oscillator of the receiving transducer is 20 mm in diameter for either cases with a resonant frequency of 2.5 MHz. In addition, the magnitude of the stepped voltage is 500V.

Figure 4:
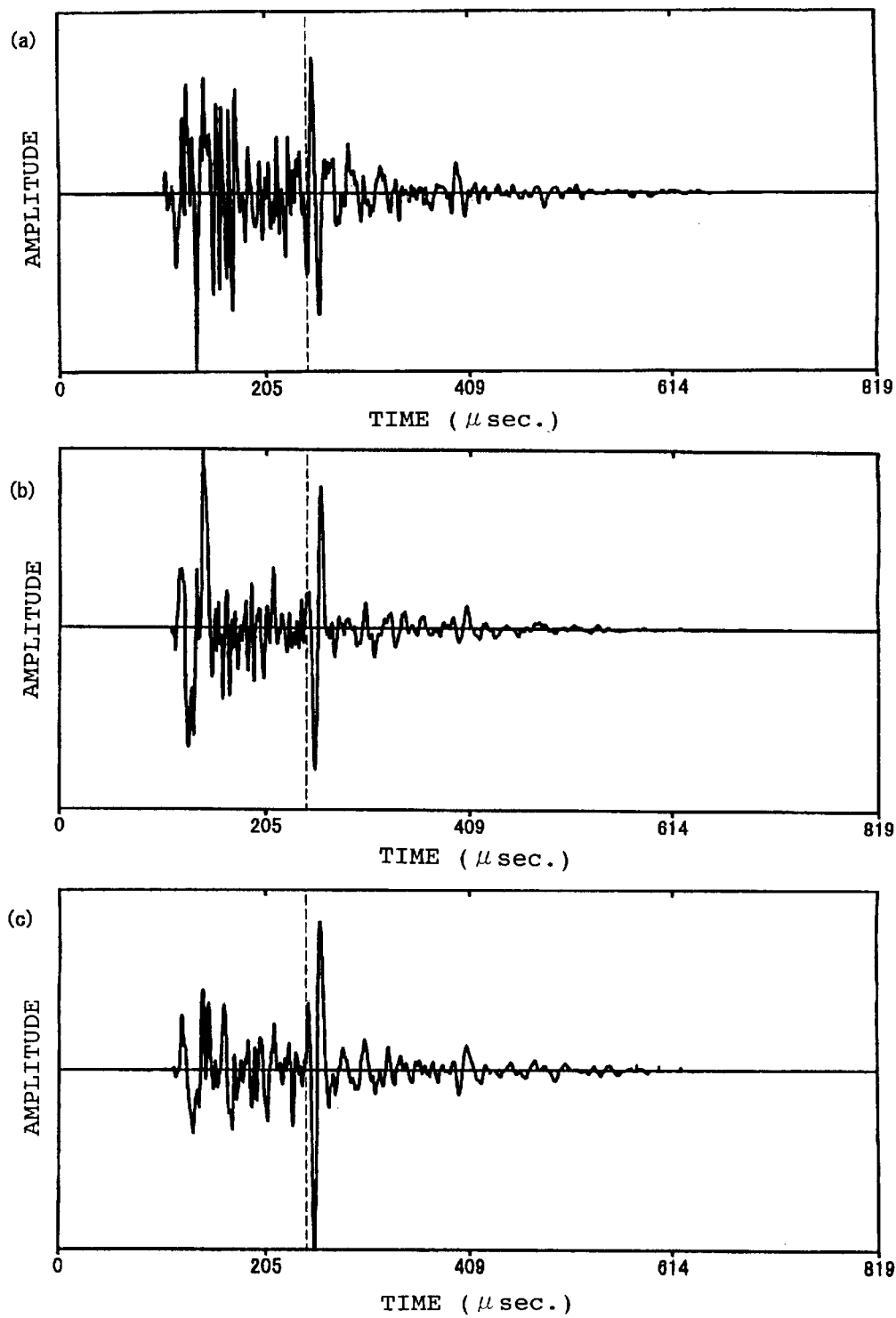
FIGS. 4(*a*) through (*c*) are graphs illustrating time series waveforms resulted from a measurement according to the method of the first embodiment.

FIG. 4 is a view illustrating the results of measurements according to the first exemplary method. FIG. 4(a) is a graph illustrating a time series waveform provided by a measurement using a transmitting transducer having a resonant frequency of 2.5 MHz and a diameter of 20 mm. FIG. 4(b) is a graph illustrating a time series waveform provided by a measurement using a transmitting transducer having a resonant frequency of 500 kHz and a diameter of 40 mm. FIG. 4(c) is a graph illustrating a time series waveform provided by a measurement using a transmitting transducer having a resonant frequency of 500 kHz and a diameter of 70 mm. Incidentally, in FIGS. 4(a) through (c), ultrasonic waves are transmitted at time 104 μs on the horizontal axis. For example, time 205 μs in the figures shows that 101 μs have elapsed after the time of transmission.

In FIGS. 4(a) through (b), the time indicated by the dashed lines shows the time of generation of the reflected wave 53 from the center B of the bottom face of the concrete material 51a, and the peak of a longitudinal reflected wave emerges distinctly at that time. Referring to FIG. 4(a), a peak indicative of the reflected wave appears at the time after a lapse of 142.3 μs from the transmit time. In FIGS. 4(b) and (c), a peak indicative of the reflected wave appears at the time after a lapse of 141.3 μs from the transmit time. Thus, the thickness of the concrete material according to the former is expressed by the following equation 2, while the thickness of the concrete material according to the latter is expressed by the following equation 3. Here, the propagation velocity of a longitudinal ultrasonic wave through the concrete material of this model is assumed to be 4.3 mm/μs.

$$\frac{1}{2} \times 142.3 \times 4.3 \times 10^{-1} = 30.6 \text{ (cm)} \quad (2)$$

$$\frac{1}{2} \times 141.3 \times 4.3 \times 10^{-1} = 30.4 \text{ (cm)} \quad (3)$$

As shown above, the latter employing a low-frequency ultrasonic wave provided a closer value to the actual value of 30 cm, and it was also possible to make a measurement with an error of about 2% even in the former employing an oscillator having a small radius to transmit a comparatively high-frequency ultrasonic wave.

Incidentally, in the first embodiment method, the transmitting transducer and the receiving transducer are placed in close proximity to each other for measurement; however, the one-transducer method may be employed in which one transducer 6, as shown in FIG. 2, functions as transmitting and receiving transducers. In this case, for a measurement of the thickness of a concrete material, the path length of the reflected wave from the bottom face thereof would not vary and thus it is easily possible to identify the generation of a reflected wave or a detected target, like in the case where the two-transducer method is employed.

However, in some cases, it is difficult to identify a reflected wave even by the first embodiment method according to the present invention, described in the foregoing. For example, in the concrete material shown in FIG. 72(b), it is difficult to identify the reflected wave or a detected target when a transducer 52' is placed at center A' of a surface 30 cm in width to measure the thickness according to the first exemplary method.

Figure 5:
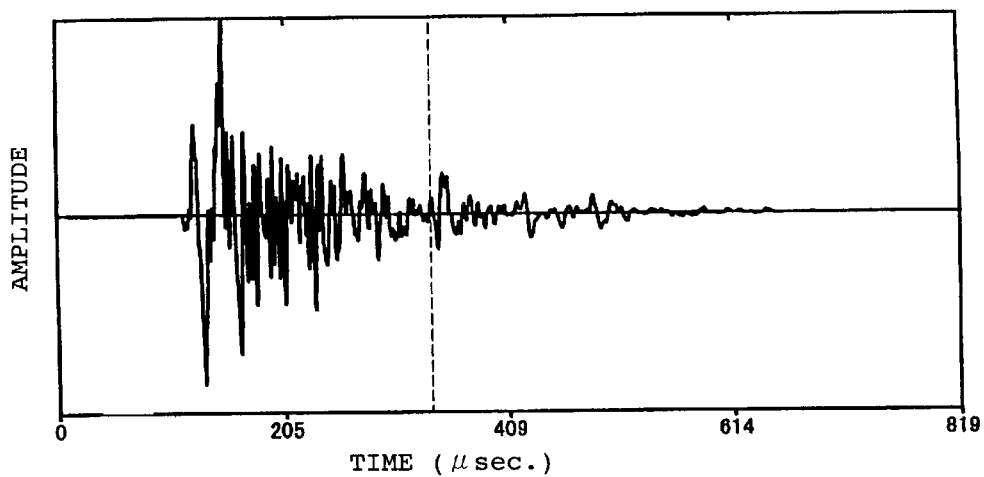
FIG. 5 is a graph illustrating a time series waveform provided by the measurement of the width of a concrete material 51*a*.

FIG. 5 is a graph illustrating a time series waveform provided by the measurement of the width (50 cm) of the concrete material 51a. Incidentally, this measurement employed a transmitting transducer having an oscillator 40 mm in diameter whose resonant frequency is 500 kHz and a receiving transducer having an oscillator 20 mm in diameter whose resonant frequency is 2.5 MHz, with the magnitude of a stepped voltage being 500V. In addition, the number of times of arithmetic averaging was 10,000 times. That is, it was under the same conditions as those of the measurement in FIG. 4(b). Incidentally, referring to FIG. 5, ultrasonic waves are transmitted at time 104 μs on the horizontal axis. For example, time 205 μs in the figure shows that 101 μs have elapsed after the time of transmission.

In FIG. 5, the time indicated by the dashed line is the theoretical time of generation of the reflected wave 53' from the center B' of a side of the concrete material 51a; however, unlike FIG. 4(b), it is difficult to identify the time as the time of generation of the reflected wave 53' in this time series waveform.

This is because, in the measurement at the center A and at the center B, the width of the surface on which the transducer is placed is 50 cm for the former and 30 cm for the latter, while the thickness to be measured is 30 cm for the former and 50 cm for the latter. As the width of the surface on which the transducer is placed is reduced or the thickness to be measured is increased, the energy of a direct wave, a surface wave, and a feeble longitudinal wave on a surface of the concrete becomes relatively large, making it easier to superimpose these waves upon a reflected wave to be detected. Furthermore, a corner-reflected wave and a reflected wave from the bottom face are received substantially at the same time. For this reason, even when measurement is made using the same detection apparatus by the same method, measurable and immeasurable waves are produced.

In this regard, a second embodiment method of the present invention allows the transmitting transducer and the receiving transducer to move within predetermined regions different from each other.

Figure 6:
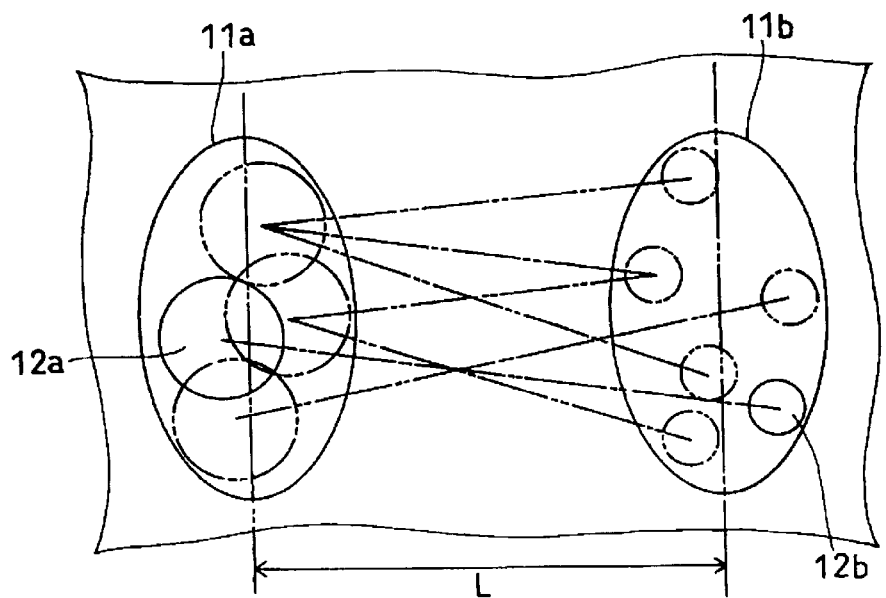
FIG. 6 is a schematic view illustrating the positional relationship between a transmitting transducer and a receiving transducer specified by a method according to a second embodiment method of the present invention.

FIG. 6 is a schematic view illustrating the positional relationship between a transmitting transducer and a receiving transducer in the second embodiment method of the present invention. Incidentally, referring to FIG. 6, a pair of transducers connected to each other by a chain double-dashed line indicates each of the transducers at a moment. In FIG. 6, a transmitting transducer 12a is greater than a receiving transducer 12b in diameter; however, they may be equal to each other or the transmitting transducer 12a may be smaller than the receiving transducer 12b in diameter.

As shown in FIG. 6, the second embodiment method allows an extremely large number of measurements, for example, 10,000 times of measurements to be made while allowing the position of the transmitting transducer 12a to be continuously varied within an elliptical region 11a and the position of the receiving transducer 12b to be continuously varied within an elliptical region 11b. Incidentally, for example, the distance L between the centers of the elliptical region 11a and the elliptical region 11b is 15 cm. Here, like in the first embodiment method, it is necessary to apply oil or the like in advance as an ultrasonic wave transmitting medium to a surface of a material being detected. Then, like in the first embodiment method, using the detection apparatus shown in FIG. 1, received waves are recorded every time a stepped voltage is applied to the transmitting transducer, allowing the gate-array 4d to go automatically perform the calculation of arithmetic averaging.

Figure 7:
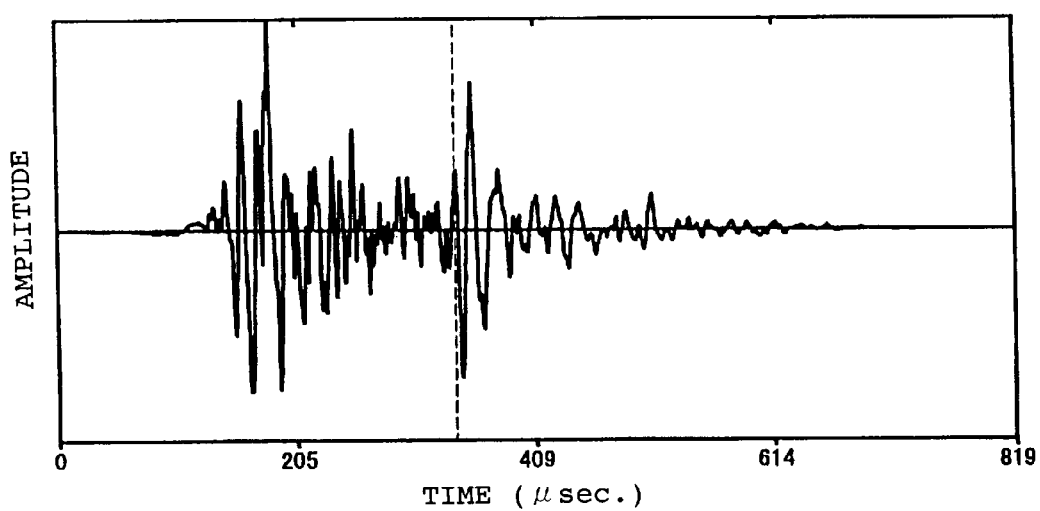
FIG. 7 is a graph illustrating a time series waveform resulted from a measurement according to the method of the second embodiment.

Illustrated are the results actually provided by the use of the transducers and application of a 500V stepped voltage for measurement according to the second embodiment. FIG. 7 is a graph illustrating a time series waveform resulted from a measurement according to the second embodiment method. Incidentally, referring to FIG. 7, ultrasonic waves are transmitted at time 104 μs on the horizontal axis. For example, time 205 μs in the figure shows that 101 μs have elapsed after the time of transmission.

In FIG. 7, the time indicated by the dashed line shows the time of generation of the reflected wave 53' from the center B' of a side of the concrete material 51a, and the peak of a longitudinal reflected wave emerges distinctly at that time. In addition, a peak indicative of the reflected wave 53' appears at the time after a lapse of 237.3 μs from the transmit time. Thus, the width of the concrete material obtained from these peaks is 51.0 cm. Accordingly, it is possible to make measurement with an error of about 2%.

Incidentally, in the second embodiment, an elliptical region is employed in which the position of the transmitting transducer or the receiving transducer varies; however, the region may be circular or rectangular. Nevertheless, in the case where the transducer is placed on a surface reduced in width of one like the material being detected in this embodiment, it is possible to make a very smooth measurement in an elliptical region or a rectangular region by employing the direction orthogonal to the width as the direction of the minor axis or shorter side. In addition, what type of region should be employed as the region can be determined by the detected target or the measuring method (the one-transducer method or the two-transducer method). Furthermore, for an elliptical region or a rectangular region, the direction of the material being detected, in which the longitudinal direction of the region is directed, can be determined in accordance with the shape of the material and the direction of a reinforcing bar arranged therein or the like.

Incidentally, the measurement of the thickness of a concrete material according to the first and second embodiment methods has been explained in the foregoing; however, the present invention is also applicable to the measurement such as of a gap inside a concrete material and the depth of a crack or the detection of a reinforcing bar.

Now, an actual example of measurement of the depth of a crack will be explained below. FIG. 8 is a view illustrating a material to be detected which is employed in an example of measurement of the depth of a crack, (a) being a perspective view, (b) being a plan view, (c) being a cross-sectional view taken along line A—A of (b), and (d) being a cross-sectional view taken along line B—B of (b).

A concrete block 21 as a material being detected has the shape of a rectangular solid having a thickness of 30 cm and the other two sides 50 cm in length. Inside the block, a total of six through reinforcing bars 22 having a diameter of 19 mm are embedded to a depth of 5 cm from the front or reverse surface and spaced apart by 15 cm. In addition, there is formed a crack 23 about 1 mm in width and 15 cm in depth.

For the measurement of the depth of the crack 23 in the concrete block 21 mentioned above, two transducers 12a, 12b having an oscillator 20 mm in diameter whose resonant frequency was 2.5 MHz were placed across the crack 23 in between two through reinforcing bars 22. In addition, a stepped voltage of 500V was employed and successively applied to the transmitting transducer 12a at 5 ms intervals. That is, ultrasonic waves were input to the concrete block 21 from the surface thereof directly downwards at intervals of 5 ms. At this time, the transmitting transducer 12a and the receiving transducer 12b were moved quickly at random within the regions 11a, 11b while each of the ultrasonic-wave transmit and receive surfaces was being kept in contact with the surface of the concrete block 21 via the ultrasonic wave transmitting medium. Then, received ultrasonic waves were recorded for each of input ultrasonic waves and arithmetic averaging was performed by the detection apparatus shown in FIG. 1.

Figure 9:
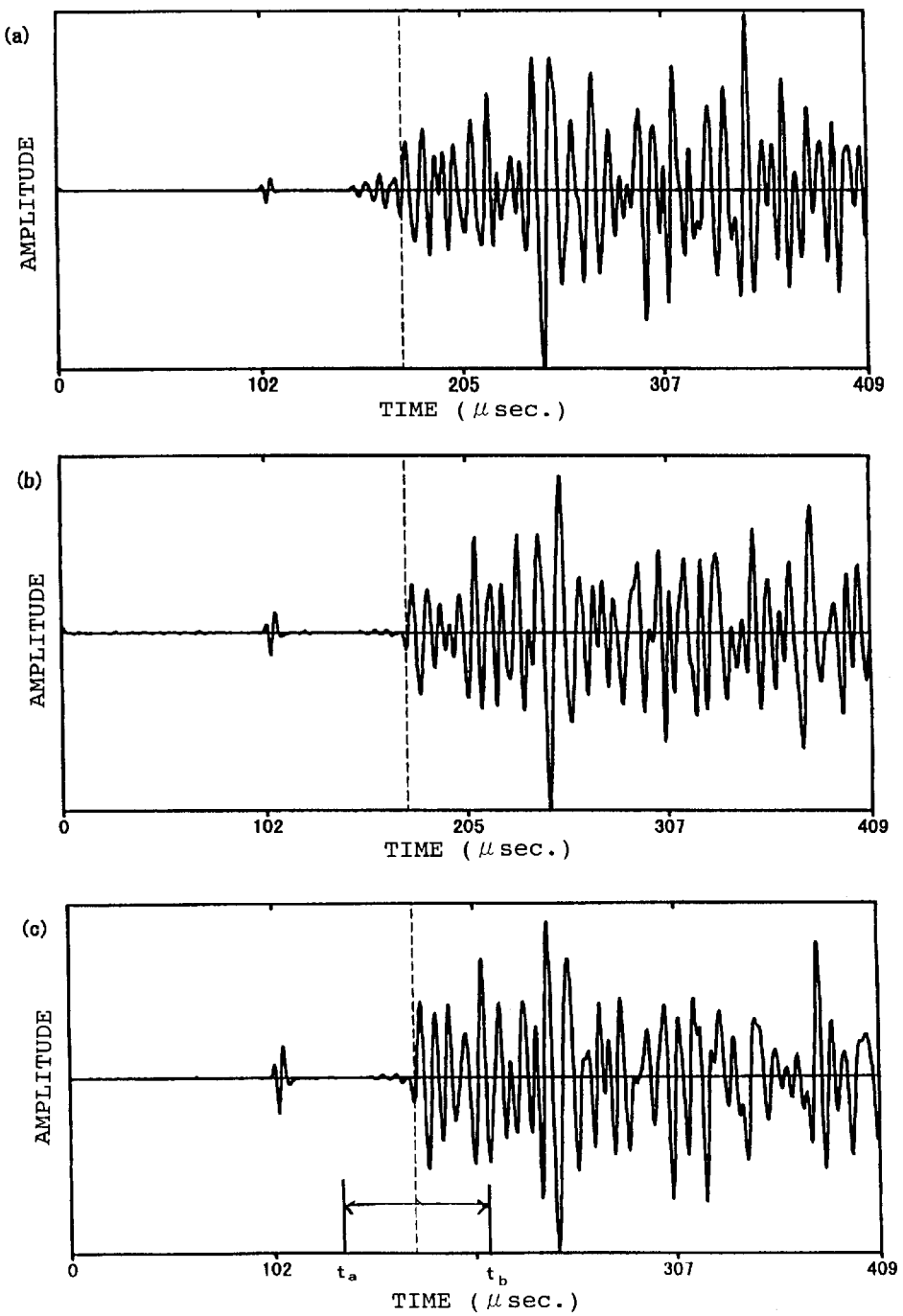
FIGS. 9(*a*) through (*c*) are graphs illustrating time series waveforms resulted from the measurement of the depth of a crack.

FIG. 9 is a view illustrating the result of a measurement of the depth of a crack, (a) being a graph illustrating a time series waveform with no arithmetic averaging having been performed, (b) being a graph illustrating a time series waveform with arithmetic averaging having been performed 1,000 times, and (c) being a graph illustrating a time series waveform with arithmetic averaging having been performed 10,000 times. Incidentally, referring to FIGS. 9(a) through (c), ultrasonic waves are transmitted at time 104 μs on the horizontal axis. For example, time 205 μs in the figures shows that 101 μs have elapsed after the time of transmission.

As shown in FIG. 9(a), with no arithmetic averaging having been performed, a waveform indicative of the generation of a wave passing through a through reinforcing bar 22 having a short transmission distance appears prior to the time indicated by the dashed line. This makes it difficult to identify the time of generation of a wave that detours around the bottom portion of the crack 23.

On the other hand, as shown in FIGS. 9(b) and (c), with arithmetic averaging having been performed 1,000 times or 10,000 times, the waveform indicative of the generation of a wave passing through the through reinforcing bar 22 is diminished, making it possible to readily identify the time (69.8 μsec) indicated by the dashed line as the time of generation of the wave that detours around the bottom portion of the crack 23. Suppose the propagation velocity of an ultrasonic wave is 4.3 m/μs in the concrete block 21. Then, the depth of the crack 23 can be determined by the following equation 4.

$$\frac{1}{2} \times 4.3 \times 69.8 \times 10^{-1} = 15.0 \text{ (cm)} \tag{4}$$

As can be seen from above, the value that is perfectly consistent with the actual value was obtained. Like the aforementioned measurement of thickness, this is because it can be assumed that a detouring wave 24 which detours around the bottom portion of the crack 23 will not have a change in its path length, even when the position of each of the transducers 12a and 12b varies within each of the movement regions 11a and 11b, due to their geometric relationship, whereas the transmission distance of a wave 25 passing through the through reinforcing bar 22 varies significantly to thereby cause its phase to significantly vary. This caused the time series wave indicative of the generation of the detouring wave 24 to increase in amplitude as the number of times of arithmetic averaging increased, thereby causing the amplitude of the wave 25 to disappear.

Incidentally, the time series waveform shown in FIG. 9 is of neither the received wave nor the very one provided by performing arithmetic averaging on the received wave but the one provided by performing the following processing on them.

First, letting an original measurement wave be y(t), filtering was performed twice in accordance with the following equation 5 and 6 between time 0 and 409 μs.

$$y_1(t) = \frac{y(t) - y(t - \Delta t)}{2} \tag{5}$$

$$y_2(t) = \frac{y_1(t) - y_1(t + \Delta t)}{2} \tag{6}$$

Furthermore, filtering was performed six times in accordance with the following equations 7 to 2.

$$y_3(t) = \frac{y_2(t) - y_2(t - \Delta t)}{2} \quad (7)$$

$$y_4(t) = \frac{y_3(t) - y_3(t + \Delta t)}{2} \quad (8)$$

$$y_5(t) = \frac{y_4(t) - y_4(t - \Delta t)}{2} \quad (9)$$

$$y_6(t) = \frac{y_5(t) - y_5(t + \Delta t)}{2} \quad (10)$$

$$y_7(t) = \frac{y_6(t) - y_6(t - \Delta t)}{2} \quad (11)$$

$$y_8(t) = \frac{y_7(t) - y_7(t + \Delta t)}{2} \quad (12)$$

where $\Delta t$ is $(10^6/(2 \times f_{HL}))$ and $f_{HL}$ is 625 kHz.

Then, $y_8(t)$ was illustrated in FIG. 9 as the time series waveform. Such filtering obviates the necessity of the inverse fast Fourier transform (FFT), thereby shortening the time for analysis. In addition, this prevents an error caused by the inverse FFT operation from entering the time series waveform. Furthermore, the aforementioned subject to be analyzed is the original measurement wave from time 0 to 409 μs; however, the time for analysis can be significantly reduced by filtering only the original measurement wave from time $t_a$ to $t_b$ shown in FIG. 9(c) as a subject to be analyzed.

Incidentally, the waveforms shown in FIGS. 9(b) and (c) ere obtained by arbitrarily moving both of the transmitting transducer and the receiving transducer within each of the movement regions 11a and 11b as shown in FIG. 8. However, measurement may be made with the position of any one transducer being fixed and only the other being moved. FIGS. 10(a) and (b) are schematic views illustrating a method for moving one transducer.

As shown in FIG. 10(a), methods for moving only one transducer 61b with the other transducer 61a being fixed include a method for providing an arithmetic averaged time series wave while the transducer 61b is moved on a segment of a general circle with center at the transducer 61a. On the other hand, as shown in FIG. 10(b), the transducer 61b may be arbitrarily moved within a predetermined region. In this case, a person skilled in the method of operating the detection apparatus can recognize the time of generation without performing arithmetic averaging with the gate-array. That is, since waves passing through right and left through reinforcing bars 62a and 62b interfere with each other, the waves passing through the through reinforcing bars 62a and 62b will substantially disappear. Thus, the time of generation of a wave detouring around the bottom portion of a crack 63 can be recognized by displaying a time series waveform on a display device every time the transducer 61b is moved. However, since this method requires a highly skilled experience to recognize the time of generation, it is necessary to perform arithmetic averaging to readily obtain the time of generation.

Figure 11:
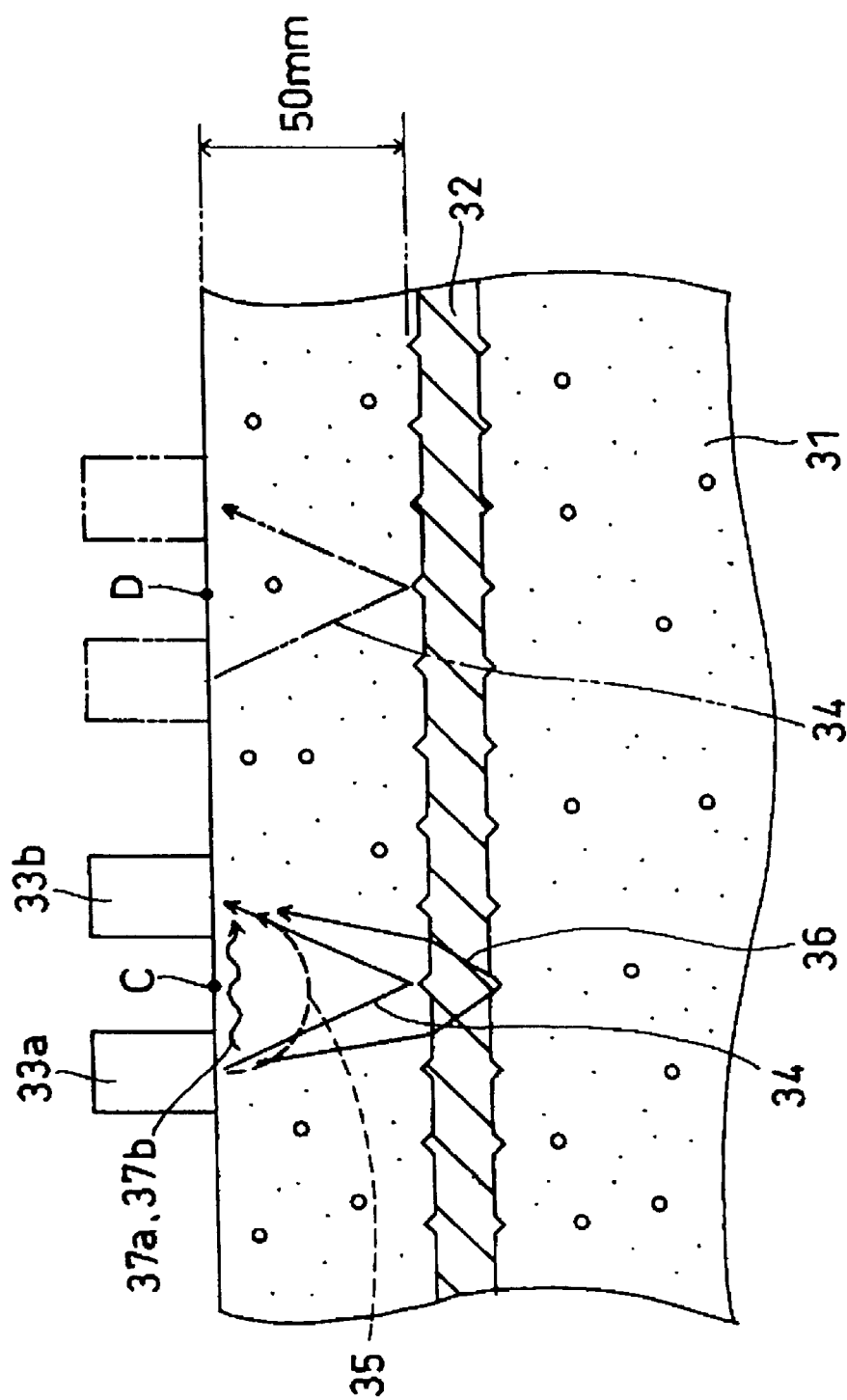
FIG. 11 is a cross-sectional view illustrating a material to be detected which is employed in an embodiment of measuring the depth of a deformed reinforcing bar.

Now, an embodiment of measuring the depth and diameter of a deformed reinforcing bar embedded in a concrete material will be explained. FIG. 11 is a cross-sectional view illustrating a material being detected which is employed in the embodiment of measuring the depth and diameter of the deformed reinforcing bar.

In a concrete material 31 to be detected, a deformed reinforcing bar 32 having a diameter of 19 mm is embedded to a depth of 50 mm from a surface thereof.

In the measurement of the depth of the deformed reinforcing bar 32 in the concrete material 31 mentioned above, a transmitting transducer 33a and a receiving transducer 33b, each having a resonant frequency of 2.5 MHz, were placed immediately above the deformed reinforcing bar 32 and spaced apart by 40 mm form each other. In addition, a stepped voltage of 500V was applied to the transmitting transducer 33a successively 1,000 times at 2.5 ms intervals. That is, the time is measured for about 2.5 s. Then, received ultrasonic waves were recorded for each of input ultrasonic waves and arithmetic averaging was performed with the detection apparatus shown in FIG. 1. Subsequently, filtering was performed on the waveform obtained by the arithmetic averaging.

In this filtering, used as a filter was the function shown by the following equation 13, which was obtained by multiplying $\sin^k((\pi/2) \times (f/f_{HL}))$ by $\cos^n((\pi/2) \times (f/f_{HL}))$, and $Y_B$ of arithmetic averaging wave $y_B(t) = Y_B 19 \exp(i\omega_y t)$ was multiplied by this function.

$$\sin^k\left(\frac{\pi}{2} \cdot \frac{f}{f_{HL}}\right) \cdot \cos^n\left(\frac{\pi}{2} \cdot \frac{f}{f_{HL}}\right) \quad (13)$$

Hereinafter, $\sin((\pi/2) \times (f/f_{HL}))$ is denoted as $C_1$ and $\cos((\pi/2) \times (f/f_{HL}))$ is denoted as $C_2$.

Figure 12:
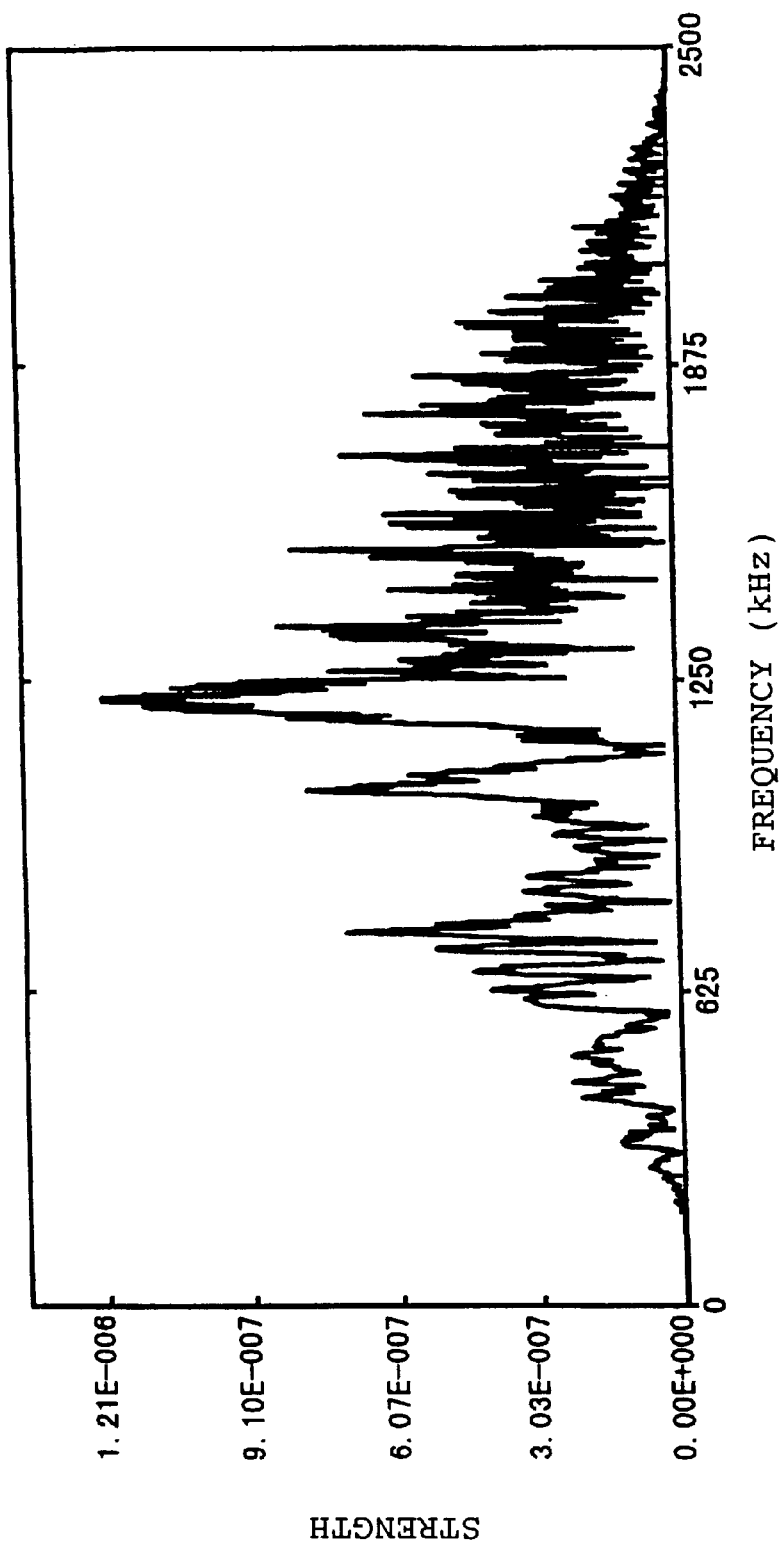
FIG. 12 is a graph illustrating a spectrum obtained when a measurement is made with transducers 33*a* and 33*b* remaining fixed at both sides across a fixed point C.

FIG. 12 is a graph illustrating a spectrum obtained when a measurement is made with the transducers 33a and 33b remaining fixed at both sides across a fixed point C. Incidentally, the spectrum shown in FIG. 12 derives from a wave having broadband (0 to 2.5 MHz) oscillation components that have been subjected to a filtering of $C_1^6 \cdot C_2^4 \cdot Y$ (where $f_{HL}$=2.5 MHz) under the conditions of a 1,000-time arithmetic-averaging received wave, $y(t) = Y \cdot \exp(i\omega_y t)$, and $f_{HL}$=2.5 MHz.

In addition, FIG. 13 is a view illustrating the results of the measurement of the depth of the deformed reinforcing bar, (a) being a graph illustrating a time series waveform obtained by making a measurement with each of the transducers 33a and 33b remaining fixed at both sides across the fixed point C, and (b) being a graph illustrating a time series waveform obtained by making a measurement while each of the transducers 33a and 33b was being moved from point C to point D. Incidentally, referring to FIGS. 13(a) and (b), ultrasonic waves are transmitted at time 104 μs on the horizontal axis. For example, time 204 μs in the figure shows that 100 μs have elapsed after the time of transmission.

A longitudinal ultrasonic wave in the concrete material 31 shown in FIG. 11 has a propagation velocity of 4.2 mm/μs, and the generation of a reflected wave 34 from the upper end of the reinforcing bar would be recognized 25.6 μs after the transmission in accordance with the following equation 14.

$$2 \times \sqrt{\left(\frac{40}{2}\right)^2 + 50^2} \bigg/ 4.2 = 25.6 \ (\mu s) \quad (14)$$

However, as shown in FIG. 13(a), for the measurement performed with each of the transducers 33a and 33b remaining fixed, it is impossible to identify the generation of the reflected wave 34 at time 25.6 μs shown by the dashed line.

On the other hand, as shown in FIG. 13(b), for a wave that has been obtained at each transmission of an ultrasonic wave by performing arithmetic averaging 1,000 times while each of the transducers 33a and 33b is moved linearly from point C to point D immediately above the deformed reinforcing bar 32 at a generally constant velocity with the transducers 33a and 33b being kept spaced apart by 40 mm, the generation of a large amplitude in the reflected wave 34 can be recognized at time 25.7 μs shown by the dashed line.

Incidentally, an ultrasonic wave transmitting medium was applied in advance to a surface of the concrete material 31 so that the transmit and receive face of each of the transducers 33a and 33b could tightly contact with the surface.

The vertical axes of FIGS. 13(*a*) and (*b*) have the same scale. A number of waves having a large amplitude, generated in FIG. 13(*a*), show the generation of a direct wave 35, a surface wave 37, a longitudinal wave (not shown), and scattered wave (not shown). Since the distance between the transmitting transducer 33a and the receiving transducer 33b is as short as 40 mm, the direct wave 35, the surface wave 37, the longitudinal wave, and the scattered wave are provided with a large amplitude, which last-for a long time. In addition, the reflected wave 34 as a target to be detected is submerged among these waves.

Incidentally, the presence of coarse aggregates (fine stones of diameters about 1 to 2 cm) and bubbles about 1 to 2 mm in diameter near the position of measurement causes the amplitude and phase of the direct wave 35 and the scattered wave to significantly vary depending on the position of measurement. Accordingly, waves having different phases cancel out each other by performing arithmetic averaging on the received waves while the transmitting transducer 33a and the receiving transducer 33b are moved, thereby causing the direct wave 35 and the scattered wave to disappear as the number of times of addition increases. At this time, with the distance between the transducers being kept unchanged, the reflected wave 34 from the upper end of the reinforcing bar and a reflected wave 36 from the lower end would not vary in their path length and in their phase as well. For this reason, the amplitude of the reflected wave 34 increases relatively as the number of times of addition increases. Accordingly, as shown in FIG. 13(*b*), the reflected wave 34 from the upper end of the reinforcing bar become prominent by performing arithmetic averaging 1,000 times.

However, only the generation of the reflected wave 34 can be recognized in FIG. 13(*b*), but the generation of the reflected wave 36 from the lower end of the reinforcing bar cannot be recognized. For detection of a reinforcing bar or the like having a circular cross section, the reflected wave 36 from the lower end of the reinforcing bar contains an extremely small amount of oscillation components. However, many examples of measurement show that other generated waves that provide information for measuring the diameter of a reinforcing bar can be gained as a low-frequency component wave. A method for gaining a low-frequency component wave will be explained below.

First, a filtering of $C_2{}^n \cdot Y_{1,1}$ is carried out under the conditions of a time series wave, $y_{s1,1}(t) = Y_{1,1} \cdot \exp(i\omega_y t)$, and $f_{HL} = 2.5$ MHz. In practice, the calculations shown in the following equation 15 and 16 may be carried out.

$$y_{n,1}(t) = \frac{y_{n-1,1}(t) - y_{n-1,1}(t - \Delta t)}{2} \quad (n: \text{an odd number}) \tag{15}$$

$$y_{n,1}(t) = \frac{y_{n-1,1}(t) - y_{n-1,1}(t + \Delta t)}{2} \quad (n: \text{an even number}) \tag{16}$$

where $\Delta t$ is $(10^6/(2 \times f_{HL}))$ and $f_{HL}$ is 2.5 MHz. Then, $y_{n,1}(t)$ is determined and subjected to the fast Fourier transform to determine $C_2{}^n \cdot Y_{1,1}$.

Figure 14:
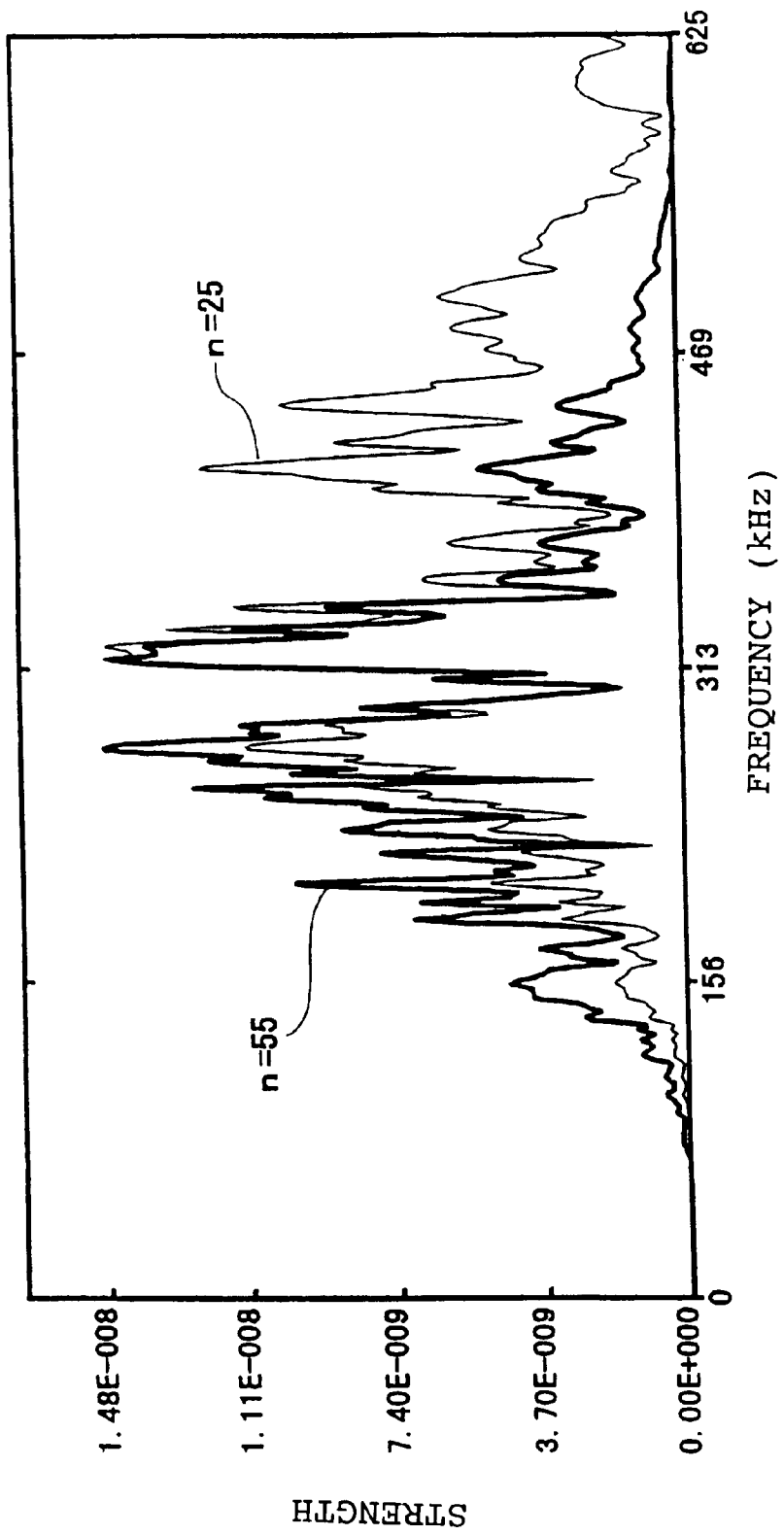
FIG. 14 is a graph illustrating spectra obtained by filtering of $C_2^n \cdot Y_{1,1}$.

FIG. 14 is a graph illustrating spectra obtained by a filtering of $C_2{}^n \cdot Y_{1,1}$. Referring to FIG. 14, a thin line represents a spectrum for n=25 and a bold line represents a spectrum for n=55.

FIG. 15 is a view illustrating time series waveforms corresponding to the spectra shown in FIG. 14, (*a*) being a graph for n=25 and (*b*) being a graph for n=55. The time series waveforms shown in FIGS. 15(*a*) and (*b*) are provided by raising actually obtained time series waves to the fourth power at each point in time. Incidentally, referring to FIGS. 15(*a*) and (*b*), ultrasonic waves are transmitted at time 104 $\mu$s on the horizontal axis. For example, time 205 $\mu$s in the figure shows that 101 $\mu$s have elapsed after the time of transmission.

As shown in FIGS. 15(*a*) and (*b*), the time series wave for n=55 contains a larger number of low-frequency components than the time series wave for n=25. In addition, in the time series ave for n=55, it is possible to recognize a peak 37 indicative of the generation of a wave for providing information about the diameter of the deformed reinforcing bar 32, which cannot be recognized in the time series wave that contains a large number of high-frequency components shown in FIGS. 13(*a*) and (*b*), at the time shown by the dashed line after a peak 34a of the reflected wave 34 from the upper end of the reinforcing bar.

Figure 16:
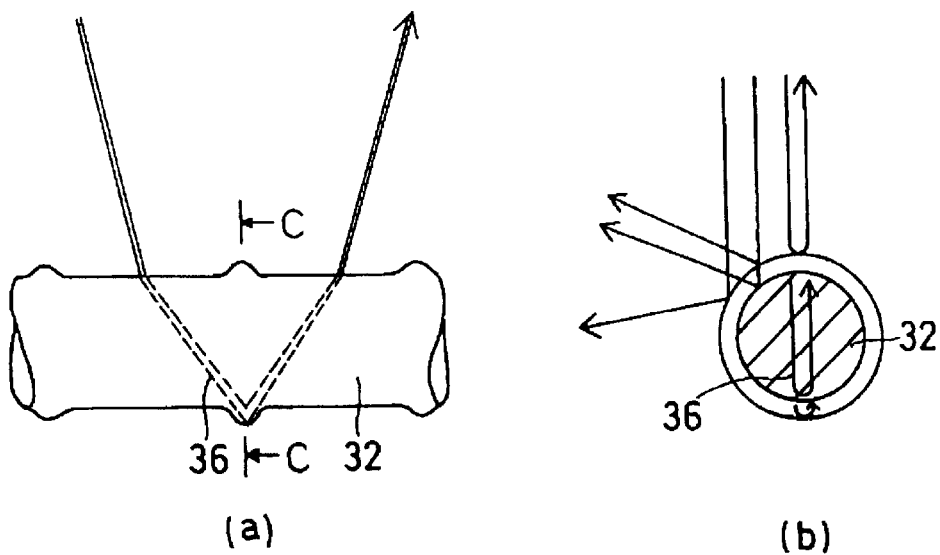
FIG. 16 is a view illustrating a path of ultrasonic waves in a deformed reinforcing bar, (a) being a side view and (b) being a cross-sectional view taken along line C—C of (a).

However, the wave indicated by the peak 37 does not show the reflected wave 36 from the lower end of the reinforcing bar. FIG. 16 is a view illustrating a path of ultrasonic waves in a deformed reinforcing bar, (a) being a side view and (b) being a cross-sectional view taken along line C—C of (a). As shown in FIGS. 16(*a*) and (*b*), a reinforcing bar or the like, circular in cross section, provides the reflected wave 36 extremely feeble in strength from the lower end thereof, making it difficult to recognize the wave in a number of measurements without using other special measuring methods.

On the other hand, a time series wave that has been gained with a low-frequency broadband of 150 to 500 kHz as shown in FIG. 14 would make it possible to recognize the peak 37a shown in FIG. 15(*b*) in any measurement embodiments of the same type.

Figure 17:
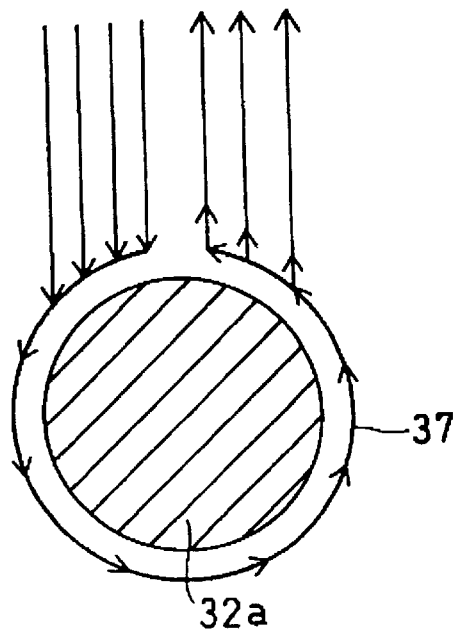
FIG. 17 is a schematic view illustrating ultrasonic waves transmitting in a circumferential direction of a circular reinforcing bar.

In this regard, it is conceivable that, in a reinforcing bar embedded in a concrete material and having a circular cross section, a pipe, a circular gap, and the like, there exists an ultrasonic wave that transmits in their circumferential direction. FIG. 17 is a schematic view illustrating ultrasonic waves transmitting in a circumferential direction of a circular reinforcing bar. As a result of actually measuring about 50 times and examining a circular reinforcing bar 32a, it was confirmed that the peak 37 was the generation of superimposition of waves transmitting in the reinforcing bar and detouring around the concrete material in the direction of the circumference of the reinforcing bar. Consequently, derived was the following equation 17 for calculating the diameter of the reinforcing bar in accordance with the time of generation of the reflected wave from the upper end of the reinforcing bar and the time of generation of a detouring wave that detours around the reinforcing bar or the like.

$$d = (t_1 - t_2) \times \frac{V_P}{\pi} \tag{17}$$

where d is the diameter of the reinforcing bar, $t_1$ is the time of generation of the reflected wave from the upper end of the reinforcing bar, $t_2$ is the time of generation of the detouring wave that detours around the reinforcing bar, and $V_P$ is the propagation velocity of a longitudinal ultrasonic wave in the iron material.

By substituting $t_1 = 25.5$ ($\mu$s), $t_2 = 37.3$ ($\mu$s), and $V_P = 5.9$ (mm/$\mu$s) obtained from the aforementioned measurement, into equation 17, it is given that d=22 (mm). The actual deformed reinforcing bar 32 of diameter 19 mm has the maximum diameter of 21.5 and the minimum diameter of 18 mm. Thus, the diameter is generally measured with accuracy.

Incidentally, the equation 17 holds not only for a reinforcing bar circular in cross section but also for the aforementioned pipe and circular gap.

In addition, on the surface of the concrete material 31 shown in FIG. 11, a plurality of fine cracks thinner than a hair have been produced. In contrast, different waveforms would be obtained by the same measurement made on a concrete material on which such cracks are not formed. FIGS. 18(a) and (b) are graphs illustrating time series waveforms obtained from such a concrete material having no crack formed thereon.

As shown in FIG. 18(a), the time series wave obtained from the concrete material having no cracks formed thereon is significantly different from that obtained from the concrete material having cracks formed thereon as shown in FIG. 13(b) ). FIGS. 19(a) through (c) and FIGS. 20(a) and (b) are schematic views illustrating the transmission path of ultrasonic waves in a concrete material having no cracks formed therein. In FIG. 18(a), a generation 71a of a reflected wave 71 appears in an extremely strong manner from a portion of the minimum diameter of a deformed reinforcing bar 77. In addition, a generation 72a of a surface wave 72 between the transducers and a generation 73a of a reflected wave 73 from a portion of the maximum diameter of the deformed reinforcing bar 77 also appear strongly.

Figure 19:
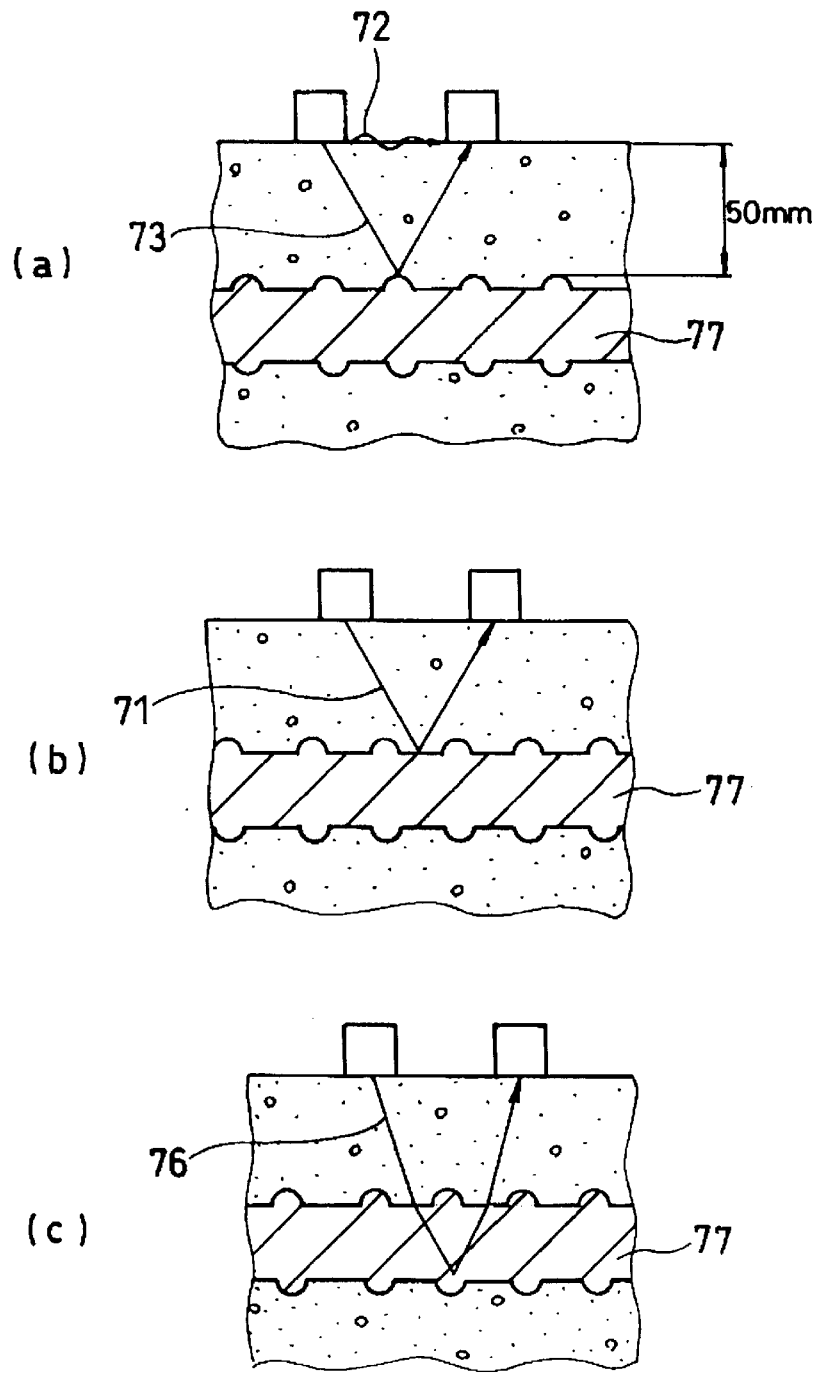
FIG. 19 is a schematic view illustrating the transmission path of ultrasonic waves in a concrete material having no crack formed therein.

On the other hand, FIG. 18(b) is a view illustrating increased generations 74a (within the reinforcing bar) and 74b (within the concrete material) of a detouring wave 74 that detours around the periphery of the reinforcing bar, and a generation 75a of a corner-reflected wave 75 from an edge portion 7.5 cm apart, with the reflected waves 71 and 73 and the surface wave 72 being diminished in amplitude. As described above, it is also possible to amplify the amplitude of a desired wave. Incidentally, the distance between the transducers is 40 mm and the deformed reinforcing bar 77 is embedded to a depth of 50 mm from a surface of the concrete material. In addition, the generation of a reflected wave 76 from the lower end of the deformed reinforcing bar 77 as shown in FIG. 19(c) was not recognized even in FIGS. 18(a) and (b). Furthermore, the time series waveform shown in FIG. 18(a) is provided by raising an actually obtained time series wave to the third power at each point in time, while the time series waveform shown in FIG. 18(b) is provided by raising the wave to the third power in the same manner.

In general, there exist a number of unrecognizable fine cracks on a surface of a concrete material and the deterioration or the like of the concrete material due to aging cannot be avoided. Accordingly, the time series waves as shown in FIGS. 18(a) and (b) can be obtained only by extremely good luck. Thus, as shown in FIG. 14 and FIGS. 15(a), (b), it is necessary to gain a low-frequency component wave by performing the aforementioned processing.

In the foregoing, it is shown that the thickness of a concrete material and the depth of a crack thereof, and the thickness of a covering and the diameter of a reinforcing bar can be measured. However, in some cases, a satisfactory measurement cannot be provided only by the aforementioned method depending on the condition of the concrete material. This is because of the following six properties of a concrete material. First, cement and stones (coarse aggregates) 1 to 3 cm in diameter are mixed and hardened into a concrete material, in which ultrasonic waves are scattered at the interface between the cement and the coarse aggregates. Secondly, typical concrete materials include an infinite number of bubbles 1 to 10 m in diameter therein and these bubbles amplify the scattering phenomenon. Thirdly, the strength of concrete materials varies greatly ranging from 360 to 700 (kg/cm$^2$) depending on the subject being constructed therewith, and the transmission and attenuation properties of ultrasonic waves vary significantly depending on this strength. Fourthly, there exist a deterioration phenomenon due to aging in concrete materials, and the transmission and attenuation properties of ultrasonic waves vary greatly depending on the level of the deterioration. Fifthly, occurrence of the scattering phenomenon in causes the shape of a subject being detected such as a floor, pillar, beam or the like to have a significant effect on the waveform of received ultrasonic waves. For example, in pillars and beams, a large number of waves or the so-called direct waves that detour around in the concrete material are produced, causing a reflected wave or the like from the subject being detected to be buried therein. Sixthly, a number of fine wide-range cracks are generally formed on a surface of the concrete material, and such cracks make detection difficult in some cases.

For example, for a concrete material being detected that has been left in adverse environments for 10 to 20 years, it is difficult to measure the thickness of the concrete material.

Figure 21:
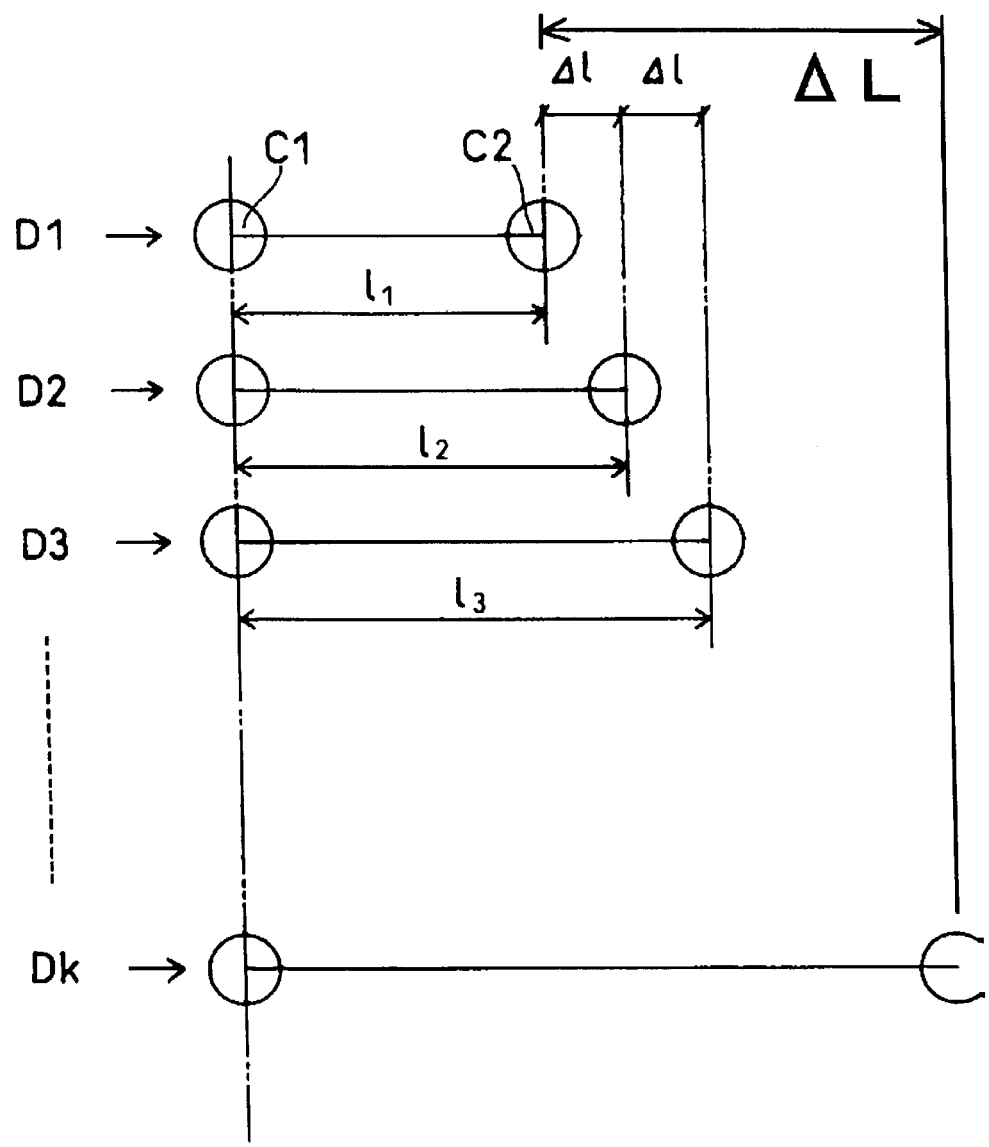
FIG. 21 is a schematic view illustrating a jig for a third embodiment of the present invention.

In such a case, measurement may be carried out with the following jig being attached to the transmitting transducer and the receiving transducer, thereby making it possible to make the measurement with accuracy. This measurement with the jig is to be employed as a third embodiment. FIG. 21 is a schematic view illustrating the jig for the third embodiment of the present invention.

The third embodiment is provided with k types of jigs D1, D2, D3, . . . Dk for keeping the distance unchanged between a transmitting transducer C1 and a receiving transducer C2. The distance between the transducers in the jig D1 is $l_1$, the distance between the transducers in the jig D2 is $l_2$, the distance between the transducers in the jig D3 is $l_3$, and the distance between the transducers in the jig Dk is $l_k$. In addition, the relationship that $1_{k+1}-1_k=\Delta l$ (constant) holds for the distances between the transducers.

In the detection method employing the third embodiment provided with such a jig, arithmetic averaging is performed on measured waves for the same number of times (n) for each jig in the same manner as in the aforementioned detection method, and thereafter arithmetic averaging is further performed on these arithmetic mean waves. Letting the received wave at the jth measurement with the jig Di be $\omega_{Di,j}$ (t), the arithmetic averaging $y_{D_i}$ (t) with the jig Di is expressed by the following equation 18.

$$y_{Di}(t) = \frac{1}{n}\sum_{j=1}^{n} \omega_{Di,j}(t) \qquad (18)$$

Then, the gate-array or the CPU incorporated into the detection apparatus is allowed to perform the arithmetic averaging of the following equation 19 or 20, thereby calculating the arithmetic mean $y_{ave}(t)$ in accordance with all measurements. Incidentally, this arithmetic averaging may be carried out with an external notebook-type personal computer.

$$y_{ave}(t) = \frac{1}{n-1}\sum_{k=1}^{n-1} \frac{1}{2}(y_{Dk}(t) + y_{Dk+1}(t)) \qquad (19)$$

-continued $$y_{ave}(t) = \frac{1}{n}\sum_{k=1}^{n} y_{Dk}(t) \quad (20)$$

Figure 22:
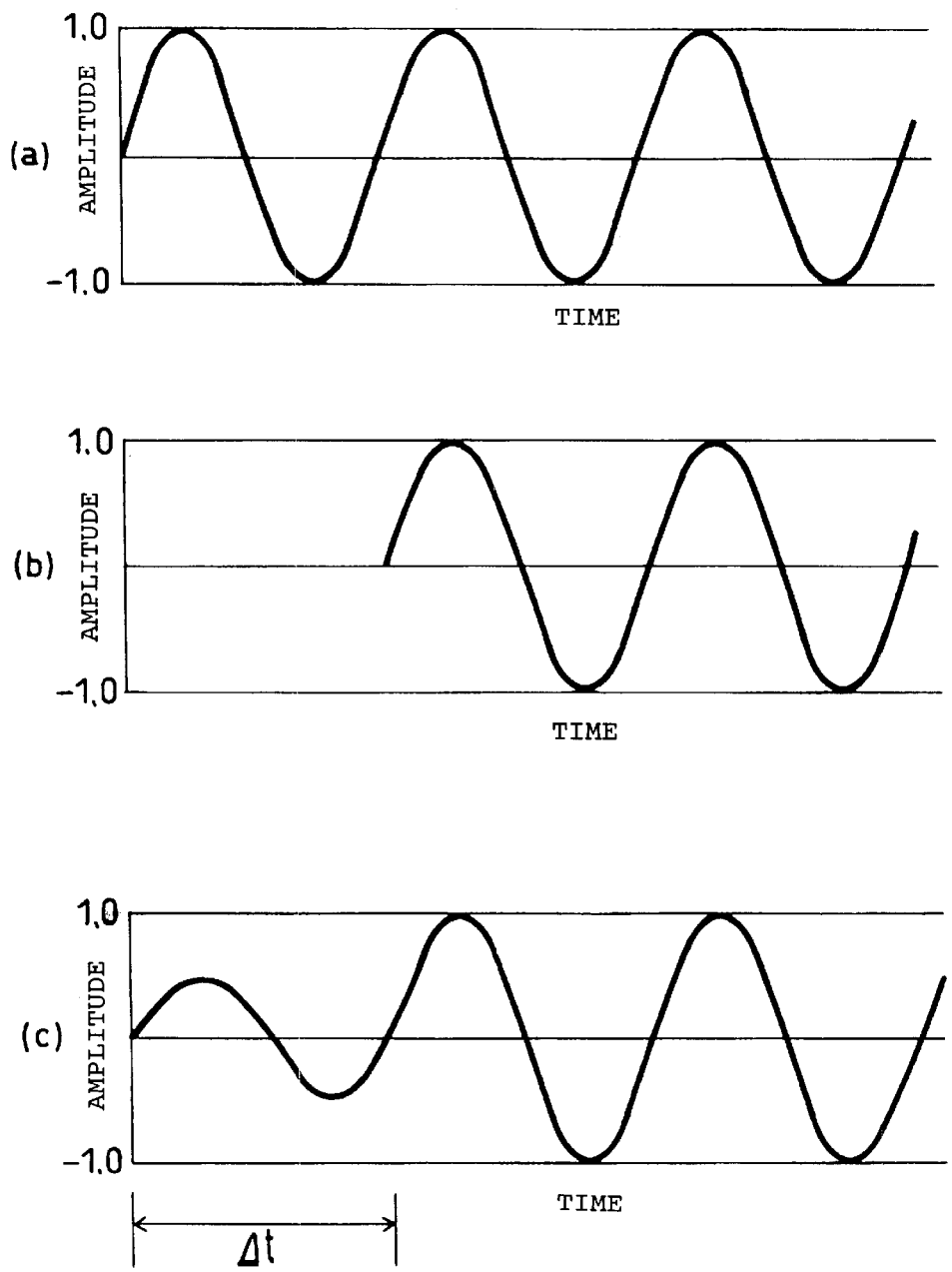
FIG. 22 is a view of an arithmetic mean $y_{Dk}(t)$, an arithmetic mean $y_{Dk+1}(t)$, and their arithmetic mean when a given frequency component is shifted by one cycle between the arithmetic mean $y_{Dk}(t)$ and the arithmetic mean $y_{Dk+1}(t)$, (a) being a schematic view illustrating the arithmetic mean $y_{Dk}(t)$, (b) being a schematic view illustrating the arithmetic mean $y_{Dk+1}(t)$, and (c) being a schematic view illustrating their arithmetic mean $_f y_{ave}(t)$.

Now, an effect that is obtained by calculating such an arithmetic mean will be described hereafter. FIG. 22 is a view of an arithmetic mean $y_{Dk}(t)$, an arithmetic mean $y_{Dk+1}(t)$, and their arithmetic mean when a given frequency component is shifted by one cycle between the arithmetic mean $y_{Dk}(t)$ and the arithmetic mean $y_{Dk+1}(t)$, (a) being a schematic view illustrating the arithmetic mean $y_{Dk}(t)$, (b) being a schematic view illustrating the arithmetic mean $y_{Dk+1}(t)$, and (c) being a schematic view illustrating their arithmetic mean $_f y_{ave}(t)$. When a given frequency component is shifted by one cycle between the arithmetic mean $y_{Dk}(t)$ and the arithmetic mean $y_{Dk+1}(t)$ as shown in FIGS. 22(a) and (b), the amplitude of the first one cycle is half that of the arithmetic mean $y_{Dk}(t)$, and the amplitude in the subsequent cycles is the same as that of the arithmetic means $y_{Dk}(t)$ and $y_{Dk+1}(t)$, as shown in FIG. 22(a). Here, it is assumed that the amplitude of each component wave of the arithmetic means $y_{Dk}(t)$ and $y_{Dk+1}(t)$ is 1.0.

FIG. 23 is a view of an arithmetic mean $y_{Dk}(t)$, an arithmetic mean $y_{Dk+1}(t)$, and their arithmetic mean when a given frequency component is shifted by one-half cycle between the arithmetic mean $y_{Dk}(t)$ and the arithmetic mean $y_{Dk+1}(t)$, (a) being a schematic view illustrating the arithmetic mean $y_{Dk}(t)$, (b) being a schematic view illustrating the arithmetic mean $y_{Dk-1}(t)$, and (c) being a schematic view illustrating their arithmetic mean $_{f/2}y_{ave}(t)$ When a given frequency component is shifted by one-half cycle between the arithmetic mean $y_{Dk}(t)$ and the arithmetic mean $y_{Dk+1}(t)$ as shown in FIGS. 23(a) and (b), the amplitude of the first one cycle is half that of the arithmetic mean $y_{Dk}(t)$, and the amplitude in the subsequent cycles is zero, as shown in FIG. 23(a).

Incidentally, a frequency component wave has zero amplitude in the second and subsequent cycles not only at a frequency of (½)f, but such a phenomenon occurs to a frequency component of (n±½)×f(n: natural number).

Figure 24:
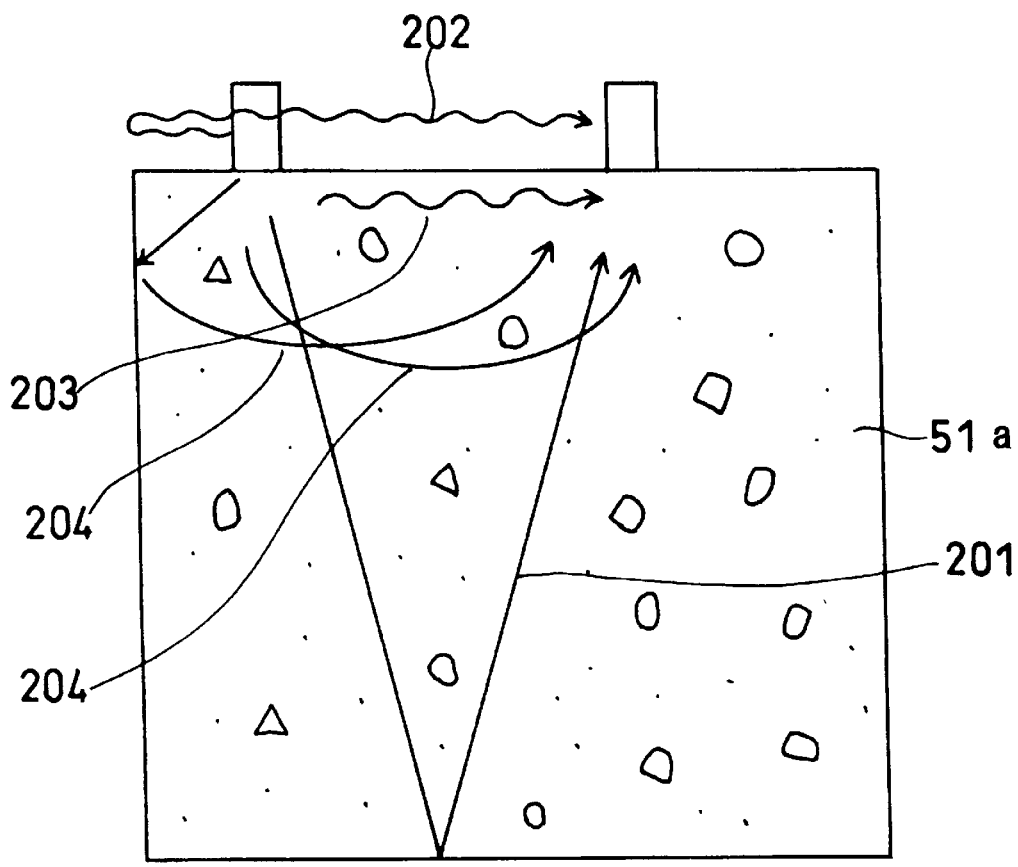
FIG. 24 is a schematic view illustrating the transmission of waves produced when a measurement is made between A' and B' shown in FIG. 72(b) by employing a two-transducer method.

Now, take an example of measurement or the like of the thickness of a concrete material. In two arithmetic mean waves measured with jigs for providing different distances between the transducers by Δl, there exist waves in transmission paths that cause the time of reception such as of reflected waves to significantly vary. FIG. 24 is a schematic view illustrating the transmission of waves produced when a measurement is made between A' and B' shown in FIG. 72(b) by employing the two-transducer method.

The time of reception of a reflected wave 201 from the bottom face of the concrete material 51a hardly varies even when the distance between the transducers varies. However, variations in distance between the transducers would cause the time of reception of path waves 202, 203, and 204 to significantly vary as described above.

Letting the transmission velocity of an ultrasonic wave be v(mm/μs), the following equation 21 holds for the difference Δt(μs) in time of reception between the two waves.

$$\Delta t = \frac{\Delta l}{v} \quad (21)$$

Figure 30:
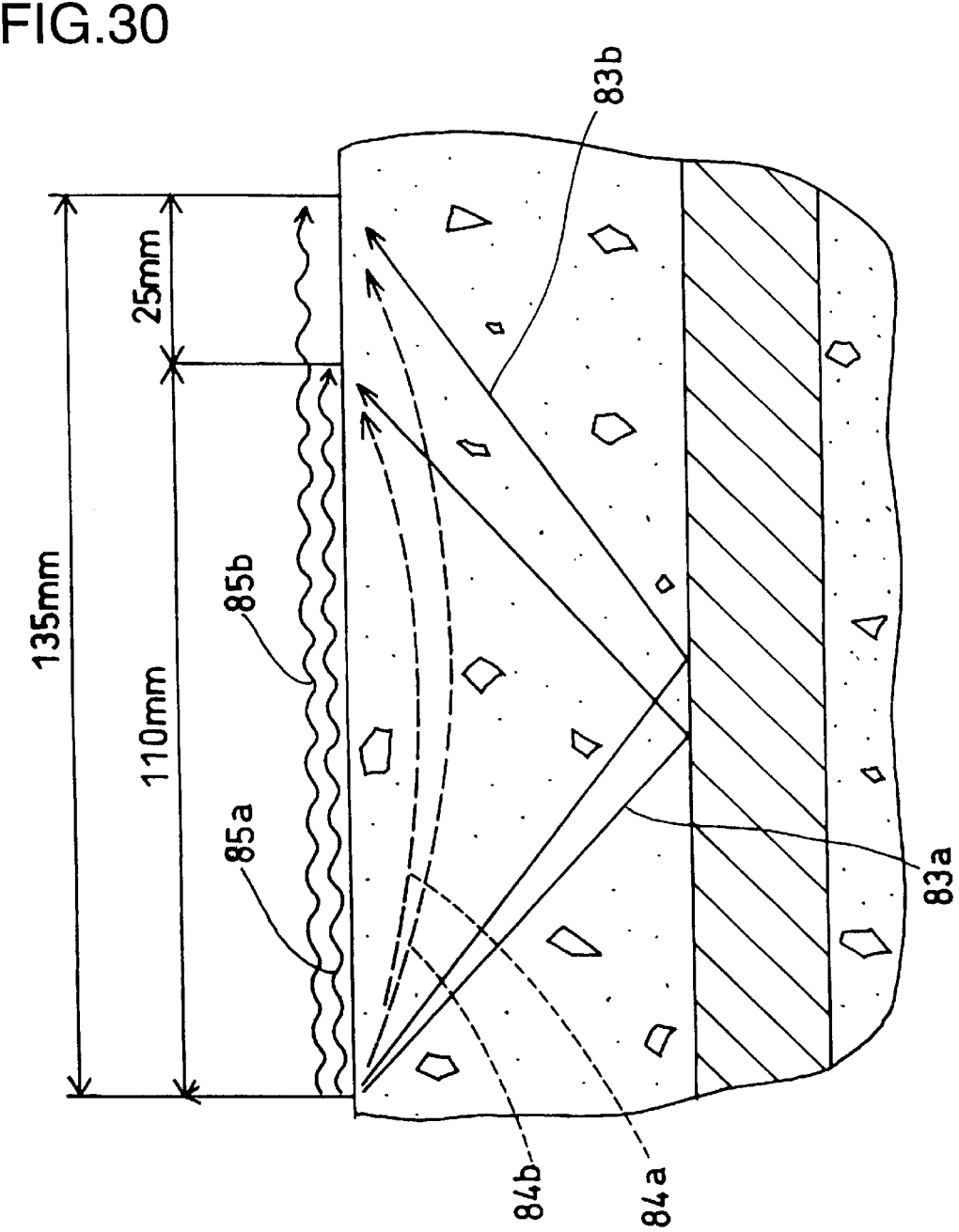
FIG. 30 is a schematic view illustrating the transmission of a wave produced upon detection of a deformed reinforcing bar 82 shown in FIG. 73.

In addition, the frequency f corresponding thereto and having an arithmetic mean $y_{ave}(t)$ shown in FIGS. 22 and 30 is expressed by the following equation 22.

$$f = \frac{10^6}{\Delta t} \quad (22)$$

Moreover, by making use of an equivalent sound velocity between the transducers $A_1$ and $A_2$, it is possible to determine a general value of the frequency f.

Letting the transmission velocity of a longitudinal ultrasonic wave in a typical concrete material be 4.0(mm/μs), the transmission velocity of the aforementioned path waves 202 to 204 would vary from 3 to 4 (mm/μs). Accordingly, as shown in FIGS. 22(a) and (b), in the arithmetic averaging obtained by using the equation 19 or 20, the path waves 202 to 204 would not be attenuated but last for a long time, assuming that the component waves within the range of frequencies shown in the following equation 23 are not attenuated. This causes the reflected wave 201 being detected to be buried in the path waves 202 to 204.

$$f = \frac{10^6}{\Delta t/3} \sim \frac{10^6}{\Delta t/4} \quad (23)$$

On the other hand, with a frequency component of (½)f, the path waves 202 to 204 are significantly attenuated as shown in FIG. 23(c). Furthermore, the transmission length of the reflected wave 201 hardly varies due to its geometric relationship, or a shift in phase hardly occurs, thereby relatively amplifying the reflected wave 201.

As described above, using the aforementioned two jigs, by gaining the component having a center frequency corresponding to one-half of the frequency f, which is obtained by the equations 21 and 22 with respect to a variation Δl in distance between the transducers, from the wave obtained by the arithmetic averaging in accordance with the equation 19 or 20, the reflected wave 201 would emerge from the path waves 202 to 204 without being buried therein.

Now, the method for measuring the thickness of an actual concrete material according to the third embodiment of the present invention and the results of the measurement will be described below.

Figure 25:
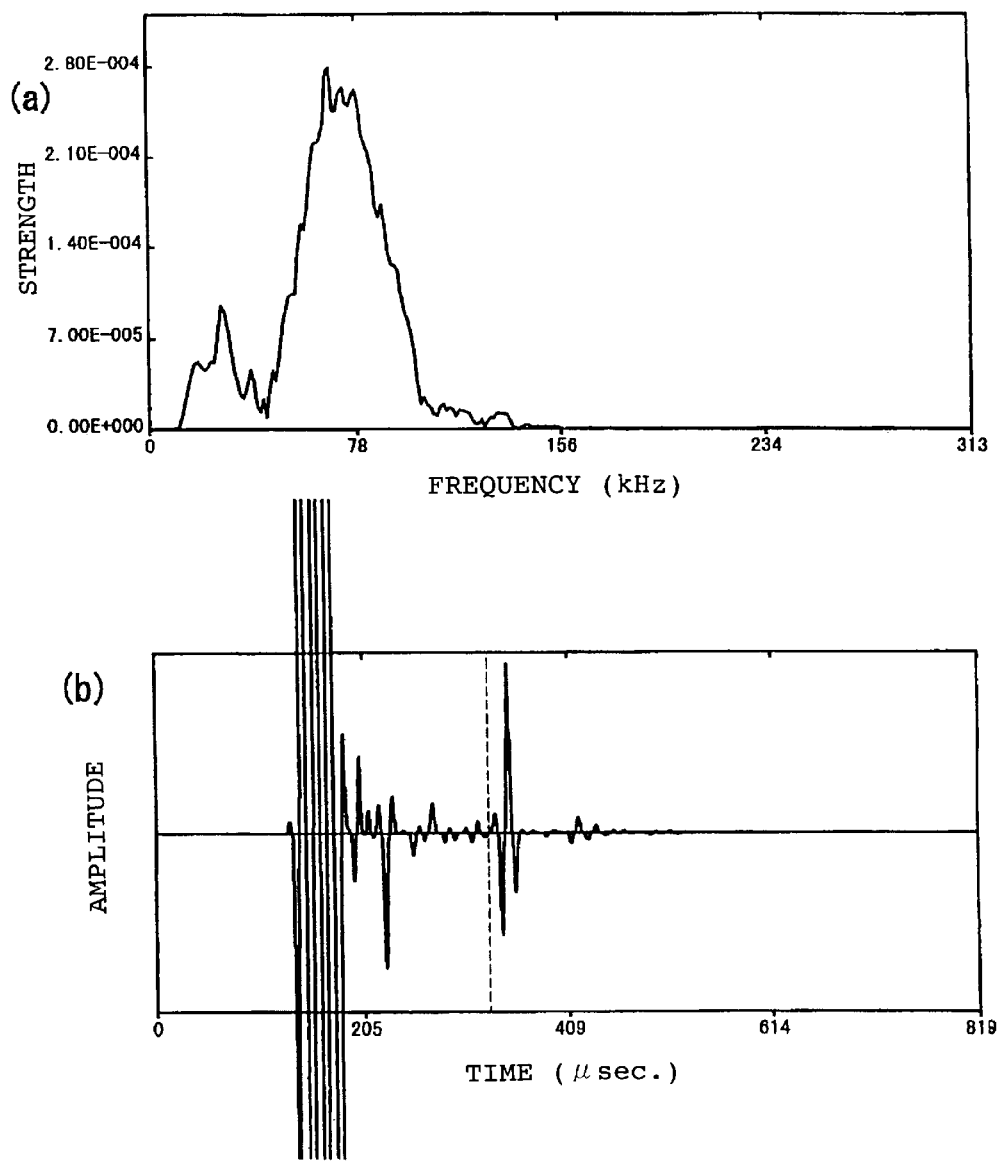
FIG. 25 is a view illustrating a wave obtained through arithmetic averaging with two types of jigs being employed, (a) being a graph illustrating a Fourier spectrum and (b) being a graph illustrating a time series waveform.

Here, employed were two oscillators, having a resonant frequency of 2.5 MHz and a diameter of 20 mm, and the jig D1 for keeping the transducers spaced apart by 81 mm, and the jig D2 for keeping the transducers spaced apart by 108 mm, where a stepped voltage was applied. That is, Δl is 27 mm. Then, as shown in FIG. 3, while the transducers were being moved within a predetermined region, arithmetic averaging was performed 4,000 times for each of the jigs to measure the distance between Δland B' of FIG. 72(b). Thereafter, the arithmetic averaging shown by equation 20 was performed and the resulting wave was gained to yield a component wave having a center frequency of 65 kHz. FIG. 25 is a view illustrating a wave of $y_{ave}(t)$ for this case, (a) being a graph illustrating a Fourier spectrum and (b) being a graph illustrating a time series waveform. As shown by the dotted line in FIG. 25(b), the generation of a reflected wave emerges distinctly from the bottom face.

Figure 26:
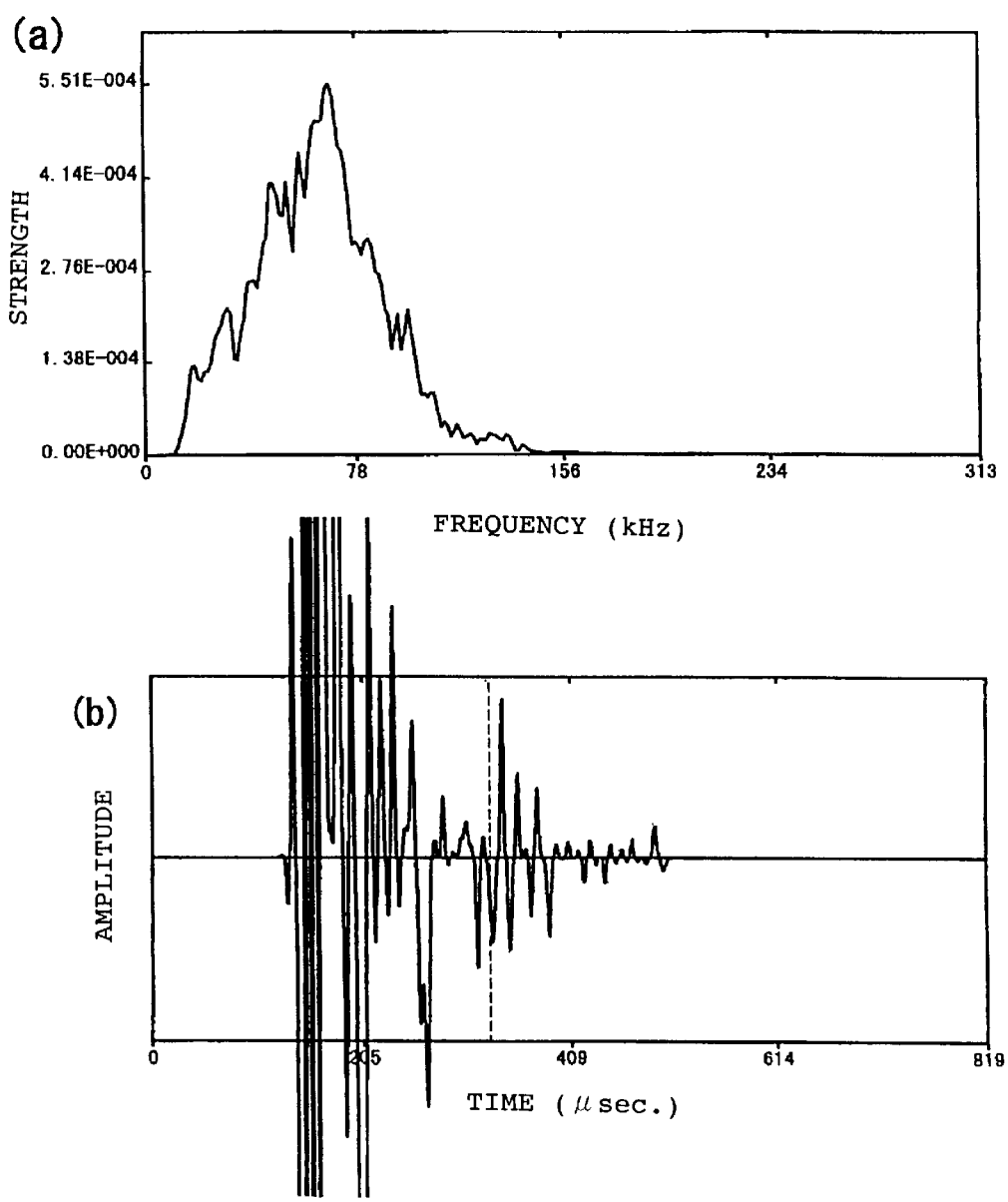
FIG. 26 is a view illustrating a wave obtained with only jig D2 being employed, (a) being a graph illustrating a Fourier spectrum and (b) being a graph illustrating a time series waveform.

On the other hand, with only the jig D2 and without the arithmetic averaging shown by the equation 19 or 20, it was difficult to recognize the generation of a reflected wave. FIG. 26 is a view illustrating a wave obtained with only the jig D2, (a) being a graph illustrating a Fourier spectrum and (b) being a graph illustrating a time series waveform. In this case, a component wave having a center frequency of 65 kHz was also gained from a combined wave indicative of arithmetic averaging performed on 4,000-time measurements. The time indicated by the dotted line in FIG. 26(b) is the theoretical time for the generation of a reflected wave, which is difficult to determine.

Incidentally, in the aforementioned detection, a component wave of 65 kHz was finally gained because of the following reasons. Substituting Δl=27 mm into equation 23 would give a frequency f of 110 to 150 kHz. One-half of this value is 55 to 75 kHz. Moreover, the center of this range is 65 kHz.

Now, the wave obtained not by using the one-halve value of the frequency but by using the center frequency 130 kHz of the range is described below. In this case, since path waves except for a reflected wave are amplified, the determination of the arithmetic mean in accordance with the equation 20 would cause the reflected wave 201 to be buried in the path waves 202 to 204 as described above. FIG. 27 is a view illustrating a wave obtained with the center frequency being at 130 kHz, (a) being a graph illustrating a Fourier spectrum and (b) being a graph illustrating a time series waveform. The time indicated by the dotted line in FIG. 27(b) is the theoretical time for the generation of the reflected wave 201, which is difficult to determine.

Incidentally, the reflected wave 201 allows a component wave of (n+½)×f to emerge, where the frequency of f is calculated in accordance with the equations 21 and 22 using a variation Δl in path length due to the aforementioned two jigs;

however, this never happens in practice because of the following reasons. For the arithmetic mean of the component waves shown in FIGS. 22(c) and 23(c), it was assumed that the component waves have not been attenuated. In practice, as shown in FIG. 25, since a reflected wave or the like consists of several waves, the reflected wave 201 is not amplified but caused to disappear when the frequency is greater than that determined in accordance with the equations 21 and 22. In addition, this phenomenon is acceleratingly amplified as the concrete material being measured becomes thicker in thickness and the wave components become higher in frequency. Because of these reasons, reflected waves are not allowed to emerge in some cases.

Now, an actual method for measuring the planar position of a reinforcing bar and the thickness of a covering thereof according to the third embodiment of the present invention and the results thereof will be described below.

Figure 28:
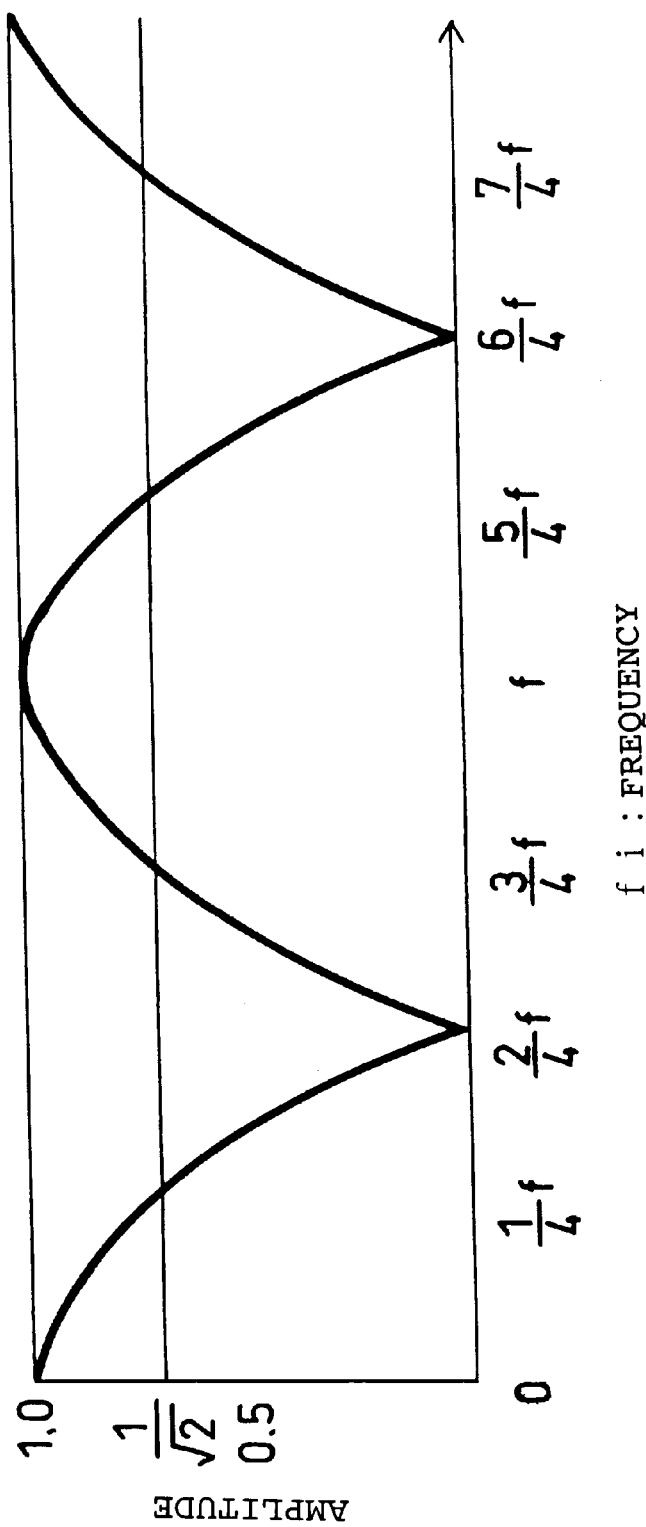
FIG. 28 is a graph illustrating the relationship between a frequency fi and a normalized amplitude.

FIGS. 22 and 30 are views illustrating how to obtain the arithmetic mean of a given low-frequency wave of frequency f, the phase of which is shifted by one cycle in each of the arithmetic mean waves measured with two jigs, and a component wave of a frequency of (½)f. By extending this, FIG. 28 illustrates the horizontal axis representing the frequency and the horizontal axis representing the amplitude value of the arithmetic mean of the arithmetic mean wave having the frequency component. The amplitude is the absolute value of a cosine function. Incidentally, the f in the figure has been calculated for a distance Δl between the transducers in accordance with the equations 21 and 22.

Figure 29:
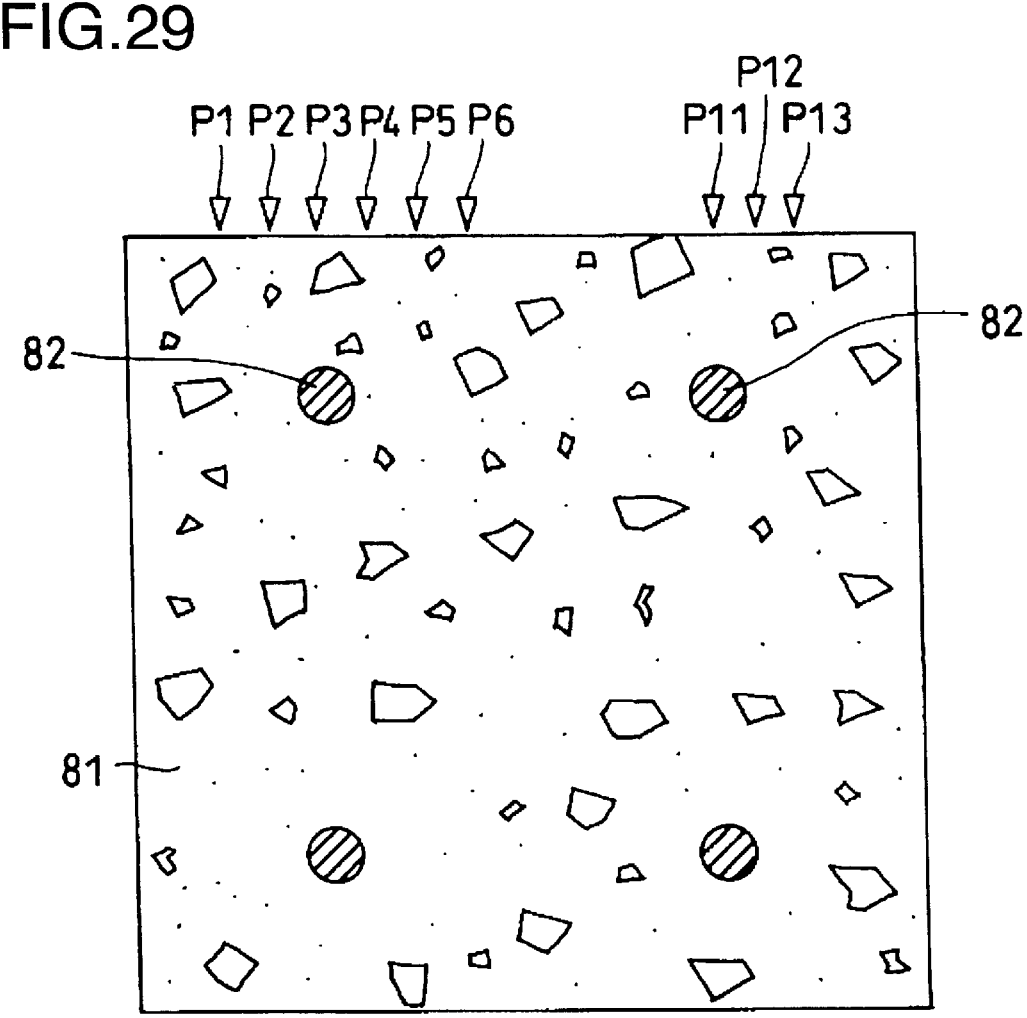
FIG. 29 is a cross-sectional view illustrating a concrete material in which a reinforcing bar as a subject to be detected is embedded.

FIG. 29 is a cross-sectional view illustrating a concrete material in which embedded is a reinforcing bar being detected. A concrete material 81 to be used for this detection is 300 mm in length, width, and height. In addition, a total of four deformed reinforcing bars 82, having a diameter of 19 mm, are embedded at positions 75 mm from both sidewalls. Furthermore, two deformed reinforcing bars 82 are embedded to a depth of 50 mm from a surface, while the other tow are at 230 mm from the surface. In addition, thirteen measurement positions P1 to P13 were set in the direction orthogonal to the longitudinal direction of the deformed reinforcing bars 82.

Then, using two types of jigs at each of the measurement positions, a 600-time arithmetic mean was determined (equation 18), respectively, and then their arithmetic mean $y_{ave}(t)$ was calculated. Furthermore, as the measuring method at this time, the transmitting transducer and the receiving transducer were slidably moved as shown in FIG. 11. Incidentally, one jig keeps the transducers spaced apart by 110 mm and the other jig keeps the transducers spaced apart by 135 mm, with a difference Δl of 25 mm therebetween. The transducers used here are the same as those used for the measurement of the thickness of the concrete material according to the aforementioned third embodiment.

FIG. 30 is a schematic view illustrating the transmission of a wave produced upon detection of the deformed reinforcing bars 82 shown in FIG. 29. The difference between the time of reception of a reflected wave 83a from the upper end of the upper reinforcing bar 82 with the transducers being spaced apart by 110 mm and that with the transducers being spaced apart by 135 mm is expressed by the following equation 24 in accordance with the equation 21 since the transmission velocity of ultrasonic waves in the concrete material 81 is 4.44 mm/µs.

$$\Delta t = \frac{2 \times \left(\sqrt{(13.5/2)^2 + 5^2} - \sqrt{(11/2)^2 + 5^2}\right)}{4.44} = 0.44 \text{ (µs)} \tag{24}$$

Accordingly, a frequency $f_A$ corresponding to this is found to be 2,300 kHz from the equation 22. That is, in FIG. 28, these arithmetic averaged component waves have the maximum amplitude at $f=f_A=2,300$ kHz and the minimum amplitude at $(½)f_A=1,150$ kHz. In addition, as the frequency fi approaches zero from $(½)f_A$, its amplitude increases in accordance with a cosine function.

On the other hand, the difference Δt in time of reception between waves 85a and 85b, transmitting on a surface of the concrete material 81, and the frequency f, corresponding to the difference are expressed by the following equations 25 and 26 for surface waves and by the following equations 27 and 28 for longitudinal waves, where the velocity of sound is 4.44×0.25 mm/µs.

$$\Delta t = \frac{25}{(4.44 \times 0.68)} = 8.33 \text{ (µs)} \tag{25}$$

$$f_B = \frac{1000}{8.33} \approx 120 \text{ (kHz)} \tag{26}$$

$$\Delta t = \frac{25}{4.44} = 5.63 \text{ (µs)} \tag{27}$$

$$f_B = \frac{1000}{5.63} \approx 180 \text{ (kHz)} \tag{28}$$

In addition, the difference Δt in time of reception between direct waves 84a and 84b and the frequency $f_B$ corresponding to the difference are expressed by the following equations 29 and 30, assuming that the equivalent velocity of the direct wave is about one-half that of the longitudinal wave.

$$\Delta t = \frac{25}{(4.44 \times 0.5)} = 11.26 \text{ (µs)} \tag{29}$$

$$f_B = \frac{1000}{11.26} = 88 \text{ (kHz)} \tag{30}$$

Figure 31:
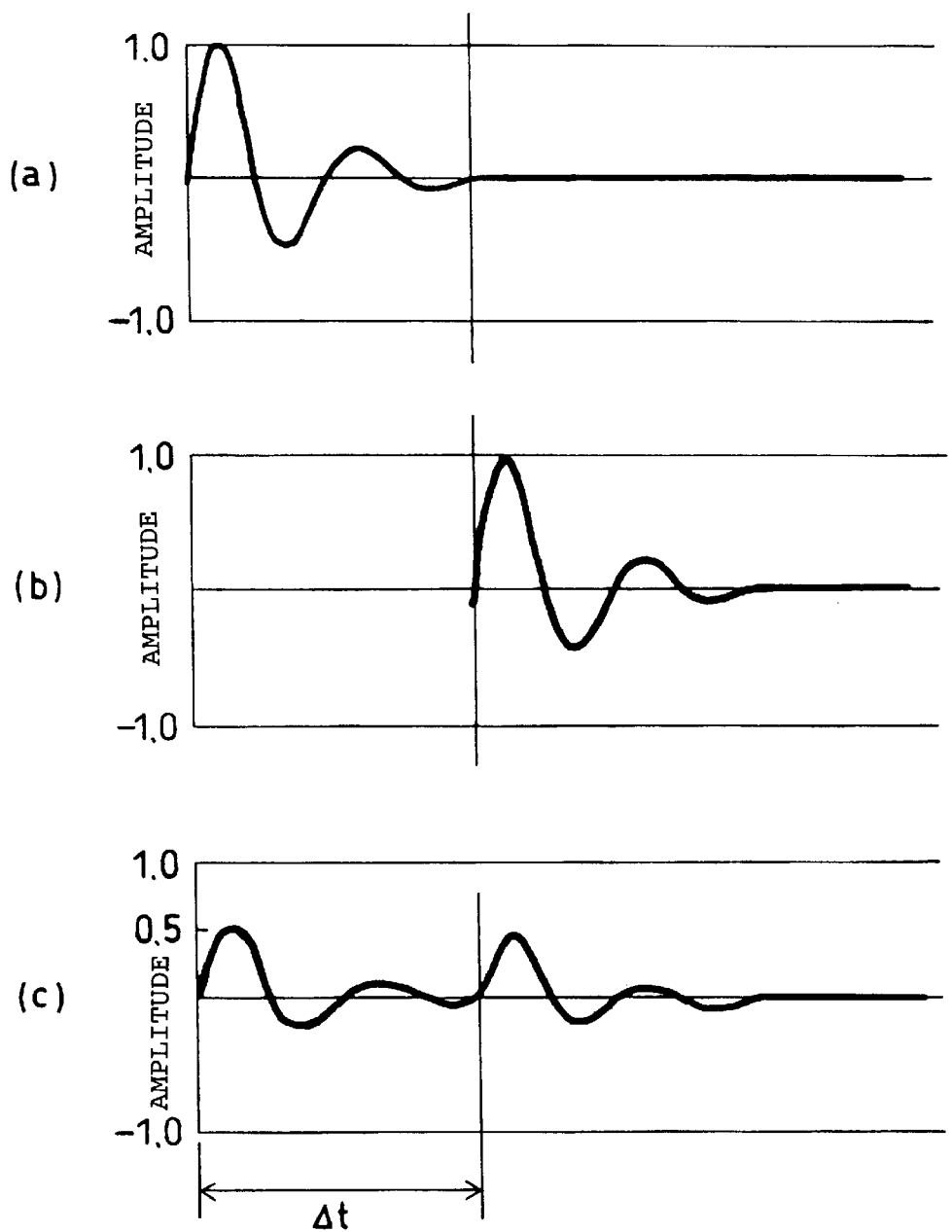
FIG. 31 is a view illustrating waves with a frequency component being $2f_B$ and two types of jigs being employed, (a) being a schematic view illustrating arithmetic mean $y_{D1}(t)$ obtained with one transducer being placed at a short distance from the other, (b) being a schematic view illustrating arithmetic mean $y_{D2}(t)$ obtained with one transducer being placed at a long distance from the other, and (c) being a schematic view illustrating their arithmetic mean $y_{ave}(t)$.

Accordingly, as shown in FIG. 28, these waves have the maximum amplitude with the frequency fi being equal to $f_B$, $2f_B$, $3f_B$ . . . . However, if the component waves of an input ultrasonic wave are attenuated in several waves, the same component wave contained in an arithmetic mean waves is to be attenuated in several waves. For example, suppose that a 50 kHz wave is attenuated in about two waves and a 500 kHz or higher wave is attenuated in about one wave. In this case, at a frequency higher than a frequency corresponding to the frequency $f_B$, the wave would disappear. FIG. 31 is a view illustrating waves with a frequency component being $2f_B$, and two types of jigs being employed, (a) being a schematic view illustrating arithmetic mean $y_{D1}(t)$ obtained with one transducer being placed at a short distance from the other, (b) being a schematic view illustrating arithmetic mean $y_{D2}(t)$ obtained with one transducer being placed at a long distance from the other, and (c) being a schematic view illustrating their arithmetic mean ye(t) obtained in accordance with the equation 20. As shown in FIGS. 31(a) and (b), with the wave number of a wave having a cycle of Δt, determined by the equations 21 and 22, being about two waves, the amplitude of their arithmetic mean $y_{ave}(t)$ is one-half that of the arithmetic mean $y_{D1}(t)$ and $Y_{D2}(t)$.

Figure 32:
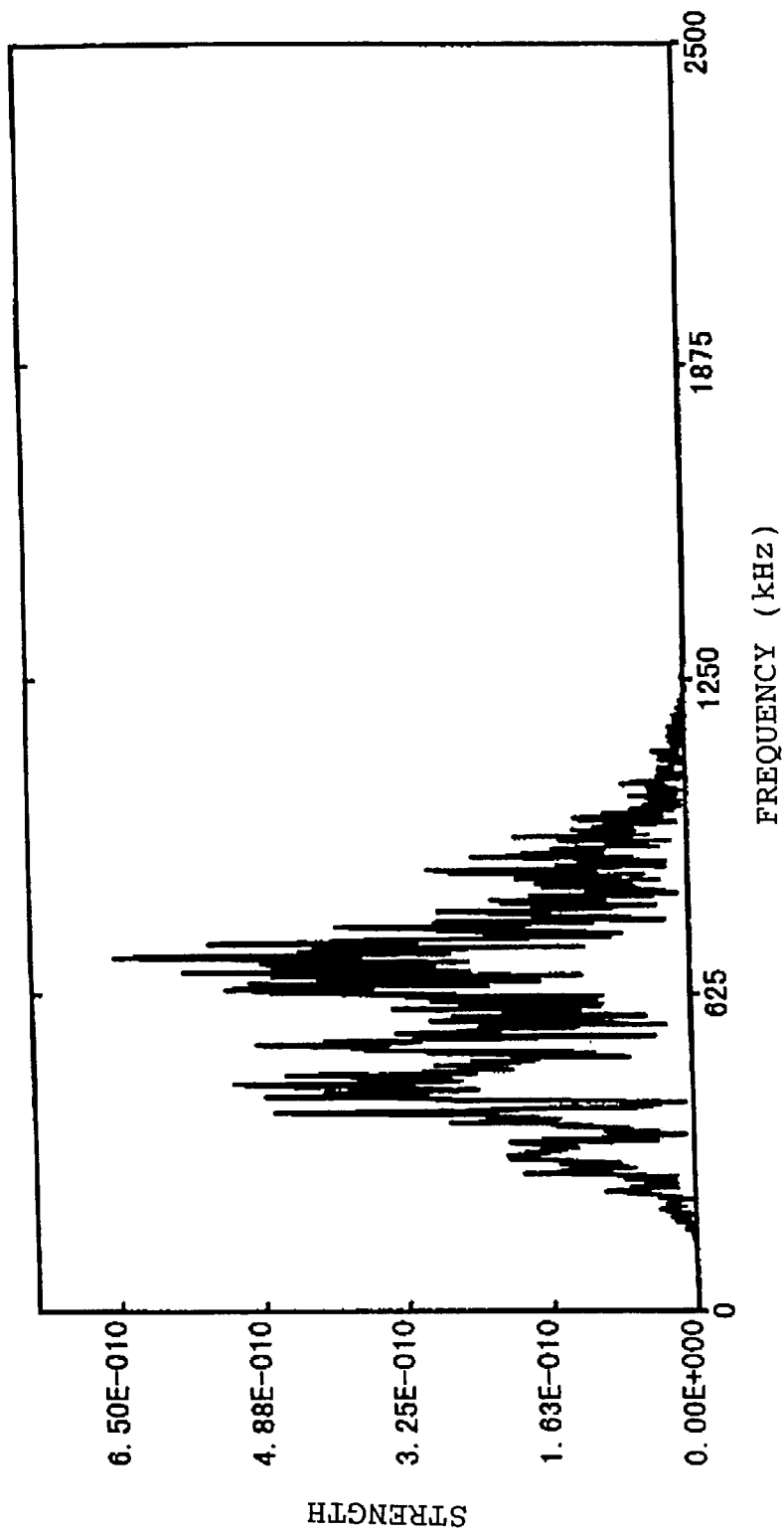
FIG. 32 is a graph illustrating the Fourier spectrum of a frequency component having a center frequency of 590 kHz used for gaining.

As described above, using the aforementioned two jigs in the measurement shown in FIG. 29, the arithmetic mean $y_{ave}(t)$ is calculated in accordance with the equation 19 or 20 and then a component wave having a given center frequency is gained by filtering in the range of frequency from $2f_B$ to $(½)f_A$, thereby making it possible to gain a reflected wave or the like from the reinforcing bar to be detected. FIG. 32 is a graph illustrating the Fourier spectrum of the gained frequency component having a center frequency of 590 kHz, while FIG. 33 is a schematic view illustrating a time series waveform at each position of measurement.

Figure 33:
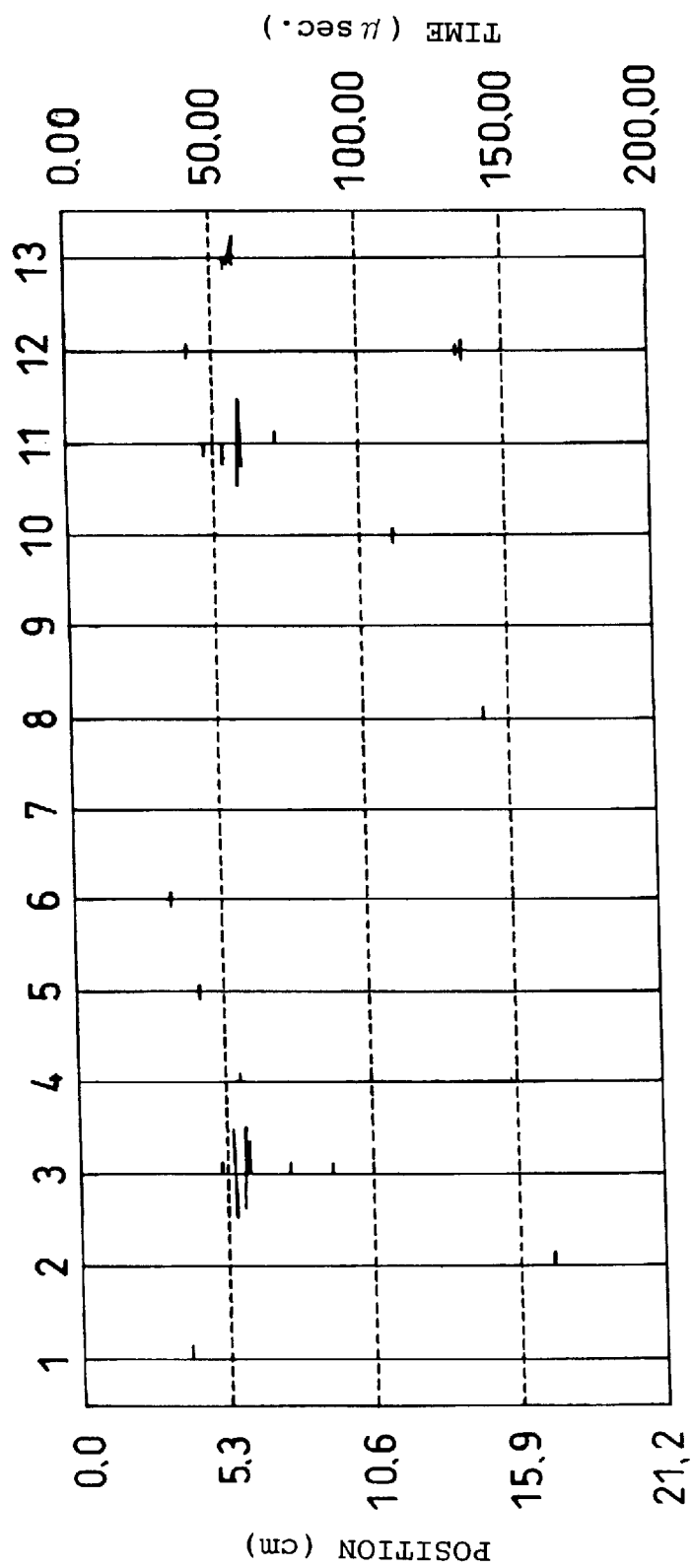
FIG. 33 is a schematic view illustrating a time series waveform at each position of measurement.

As shown in FIG. 33, a scattered wave, a direct wave, and a longitudinal and surface wave transmitting at a surface of the concrete are eliminated, causing only a reflected wave and the like from the deformed reinforcing bars 82 being detected to emerge at the measurement positions P3 and P11. That is, it is shown that the deformed reinforcing bars 82 exists generally immediately below the measurement positions P3 and P11 and the covering thereof is about 5cm in thickness. Incidentally, the numerical value on the vertical axis representative of the thickness of covering in FIG. 33 has been determined from the transmission velocity of the transverse wave. In addition, one shown in FIG. 33 was obtained by raising an actually obtained waveform to the fourth power.

Figure 34:
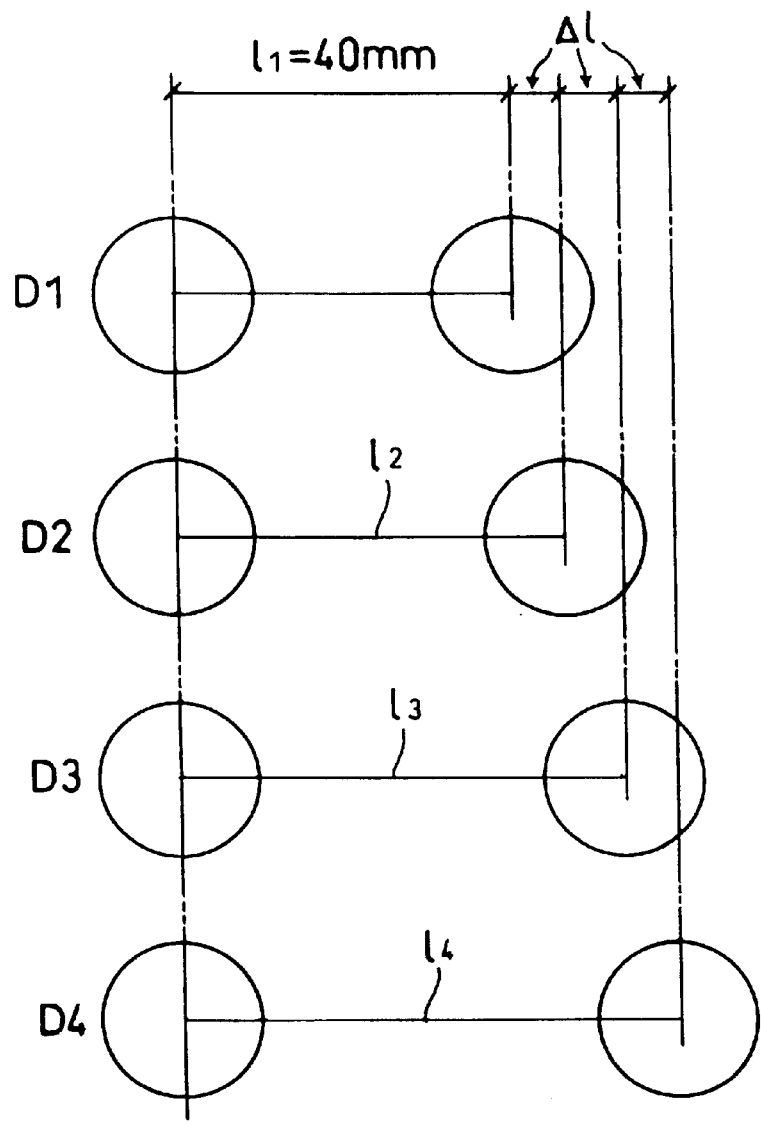
FIG. 34 is a schematic view illustrating distances between the transducers of each jig.

Furthermore, the following measurement was carried out to determine the thickness of the covering of the aforementioned deformed reinforcing bars 82, having a diameter of 19 mm, with higher accuracy and the diameter thereof. Here, employed were four jigs with the transducers of one jig being spaced apart by 4 mm longer than those of another. FIG. 34 is a schematic view illustrating the distance between the transducers of each jig. The jig D1 has a distance $l_1$ of 40 mm between the transducers, the jig D2 has a distance $l_2$ of 44 mm between the transducers, the jig D3 has a distance $l_3$ of 48 mm between the transducers, and the jig D4 has a distance $l_4$ of 52 mm between the transducers. In addition, their average distance $l_{ave}$ is 46 mm. Incidentally, the deformed reinforcing bars 82 have a maximum diameter of 21.5 mm and a minimum diameter of 18 mm, with the distance between the positions of the maximum diameter being 12 mm.

First, like in the measurement shown in FIG. 11, while the transducers are moved 10 cm on the measurement position P3 of FIG. 29 for each jig, a 1,000-time arithmetic mean $y_{Di}(t)$ was determined. Then, the arithmetic mean yac(t) shown by the following equations 31 was calculated in accordance with the equation 20.

$$y_{ave}(t) = \frac{1}{4}\sum_{i=1}^{4} y_{Di}(t) \tag{31}$$

Figure 35:
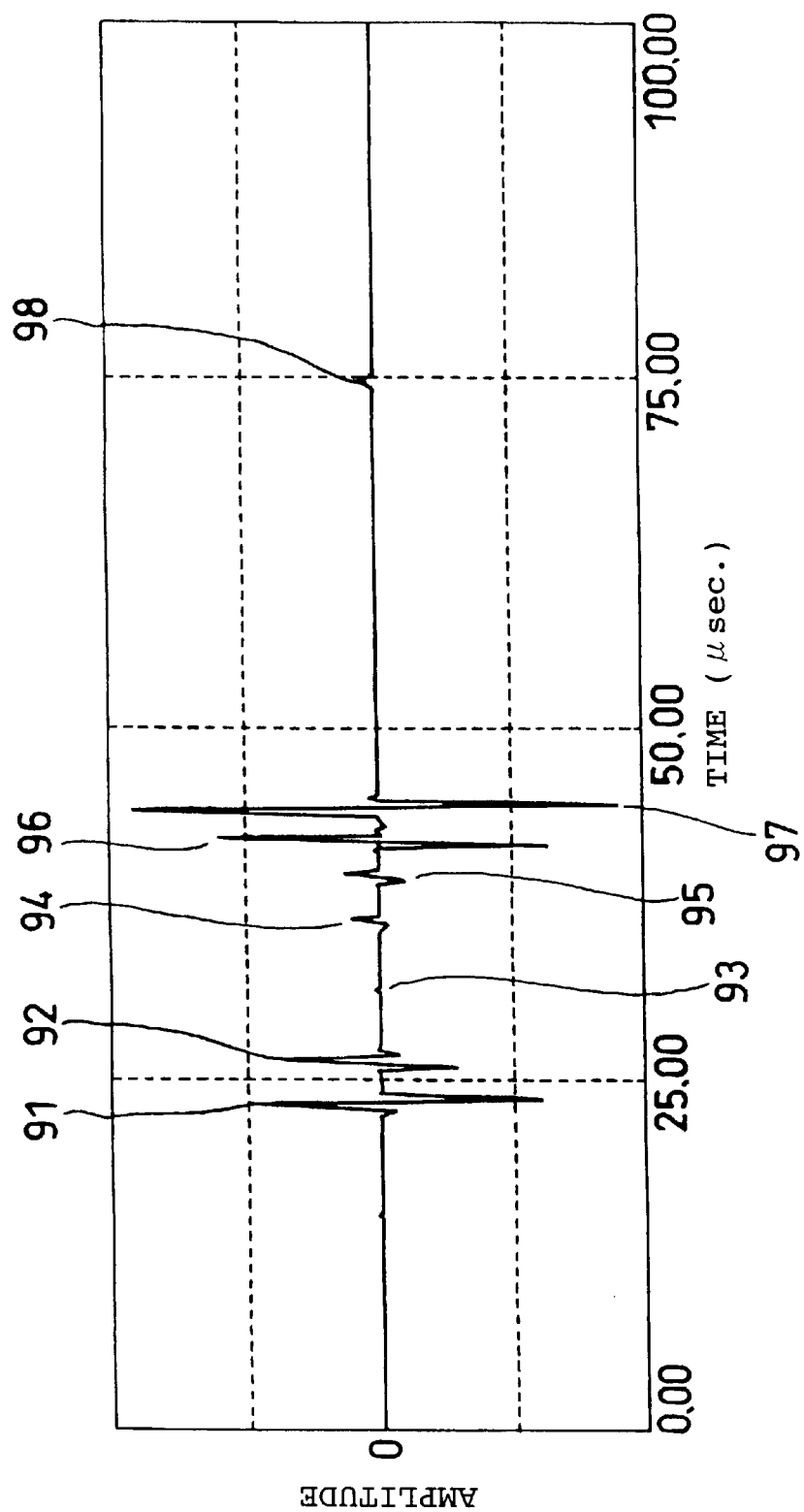
FIG. 35 is a graph illustrating time series waveforms obtained when four jigs are used.

Subsequently, a component wave in a bandwidth similar to the Fourier spectrum shown in FIG. 32 at a center frequency of 690 kHz was gained. Then, the amplitude of this wave was raised to the second power. FIG. 35 is a graph illustrating time series waveforms obtained for this case. In addition, Table 1 below shows the time of generation of each of the generated waves in FIG. 35. Incidentally, the time of generation is also shown by reference in Table 1 for waves gained with a center frequency of 1,200 kHz.

TABLE 1

| Frequency (kHz) | 91 | 92 | 93 | 94 | 95 | 96 | 97 |
|---|---|---|---|---|---|---|---|
| 690 | 23.3 | 25.8 | 30.9 | 35.9 | 38.1 | 41.7 | 43.7 |
| 1200 | 22.0 | 25.0 | 30.1 | 33.5 | 37.2 | 39.3 | 41.3 |

Of these generated waves, the peaks 91 to 97 indicate the reflected waves from the deformed reinforcing bars 82 immediately below the transducers and the waves detouring around the deformed reinforcing bars 82 or in the concrete material 81 along the periphery of the deformed reinforcing bars 82.

Now, the thickness of covering and the diameter of the reinforcing bar is measured from the time of generation shown in Table 1.

For the thickness of the covering of the reinforcing bar, the peak 91 indicates the reflected wave from the upper end of the reinforcing bar 82 with a transmission length "a" thereof being 51.73 mm from 23.3×4.44/2. In addition, according to the results of a number of measurements, letting d be the thickness of the covering of the reinforcing bar, the following equations 32 holds.

$$d = \sqrt{a^2 - \left(\frac{l_{ave} - c}{2}\right)^2} \tag{32}$$

where c is the diameter of the transducer. Then, substituting a=51.73 and the like into the equation 32 gives the thickness of the covering by the following equation 33.

$$d = \sqrt{51.73^2 - \left(\frac{46 - 20}{2}\right)^2} \approx 50 \text{ (mm)} \tag{33}$$

Since the actual measurement shows 50 mm as mentioned above, it can be said that an extremely high accuracy is provided.

Figure 36:
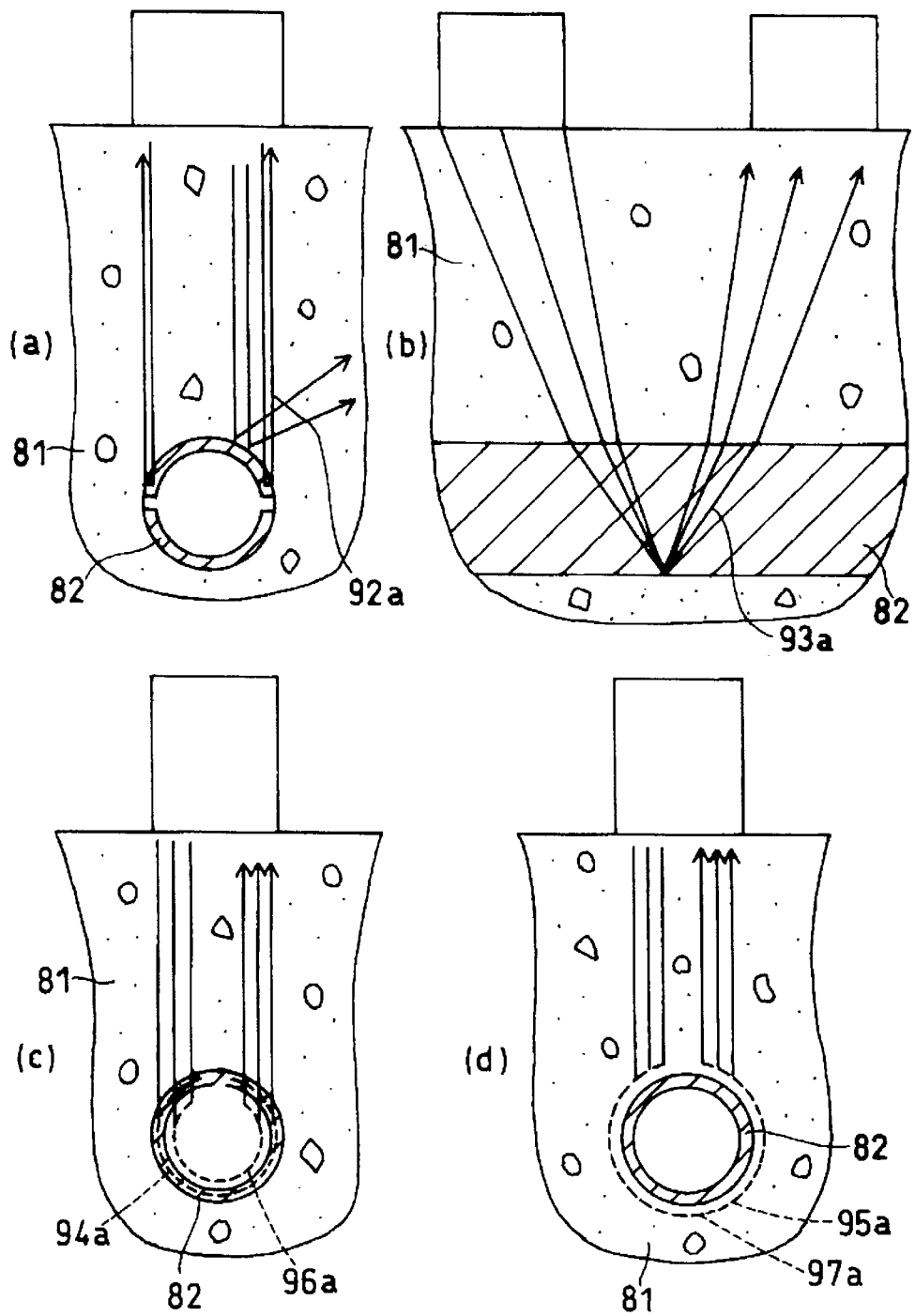
FIG. 36(a) is a schematic view illustrating a generated wave corresponding to peak 92, (b) being a schematic view illustrating a generated wave corresponding to peak 93, (c) being a schematic view illustrating generated waves corresponding to peaks 94 and 96, and (d) being a schematic view illustrating a generated wave corresponding to peak 64.

On the other hand, the generation indicated by the peaks 92 to 97 is a wave passing thorough the deformed reinforcing bar 82 immediately under the transducer. FIG. 36(a) is a schematic view illustrating a generated wave corresponding to the peak 92, (b) being a schematic view illustrating a generated wave corresponding to the peak 93, (c) being a schematic view illustrating generated waves corresponding to the peaks 94 and 96, and (d) being a schematic view illustrating a generated wave corresponding to the peaks 95 and 97.

That is, a generated wave 92a corresponding to the peak 92 is a reflected wave from the lateral edge portion of the reinforcing bar 82. On the other hand, a generated wave 93*a* corresponding to the peak 93 is a wave that is refracted at the upper end of the reinforcing bar 82, reflected on the lower end, and then further refracted at the upper end. A generated wave 94*a* corresponding to the peak 94 is a longitudinal wave detouring around in the deformed reinforcing bar 82 along the periphery of the deformed reinforcing bar 82, while a generated wave 96*a* corresponding to the peak 96 is a like transverse wave. On the other hand, a generated wave 95*a* corresponding to the peak 95 is a longitudinal wave detouring around in the deformed reinforcing bar 82 along the periphery of the deformed reinforcing bar 82, while a generated wave 97*a* corresponding to the peak 97 is a like transverse wave.

The aforementioned judgment was made in accordance with the results of measurements of the same type of about 200 examples in consideration of reproducibility of measurement.

Figure 66:
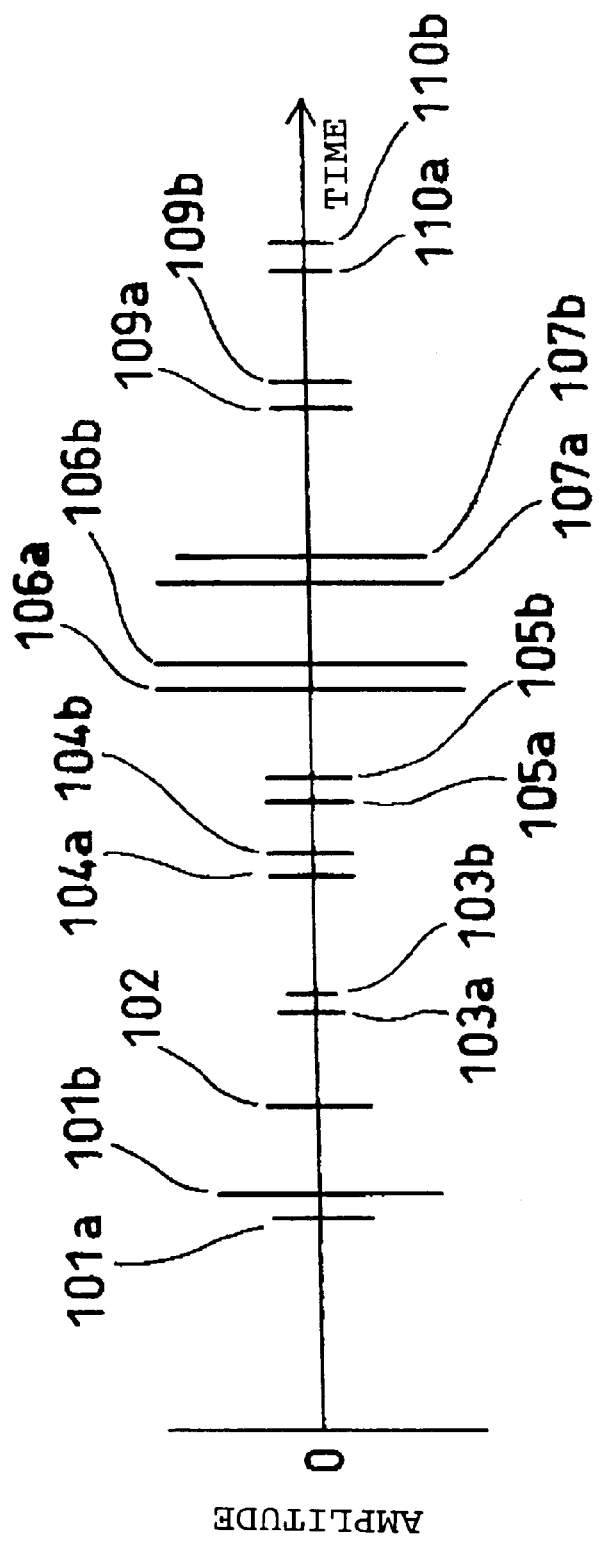
FIG. 66 is a schematic view illustrating the order of generation at various paths.

Theoretically, the order of generation of waves passing through a deformed reinforcing bar can be sorted out as follows in accordance with their path length and their velocity of sound. FIG. 66 is a schematic view illustrating the order of generation at various paths.

Referring to FIG. 66, generated waves 101*a* and 101*b* are longitudinal reflected waves from the upper end of the reinforcing bar, the former from a position of the maximum diameter and the latter from a position of the minimum diameter.

A generated wave 102 is a longitudinal reflected wave from a projection disposed in the longitudinal direction of the deformed reinforcing bar.

Generated waves 103*a* and 103*b* are longitudinal waves from the path of the generated wave 93*a*, the former from the position of the minimum diameter and the latter from the position of the maximum diameter.

Generated waves 104*a* and 104*b* are longitudinal waves detouring around in the reinforcing bar in the path of the generated wave 94*a*, the former from the position of the minimum diameter and the latter from the position of the maximum diameter.

Generated waves 105*a* and 105*b* are longitudinal waves of the path of the generated wave 95*a*, the former from the position of the minimum diameter and the latter from the position of the maximum diameter.

Generated waves 106*a* and 106*b* are transverse waves detouring around in the reinforcing bar in the path of the generated wave 94*a*, the former from the position of the minimum diameter and the latter from the position of the maximum diameter.

Generated waves 107*a* and 107*b* are transverse waves detouring around in the concrete material in the path of the generated wave 97*a*, the former from the position of the minimum diameter and the latter from the position of the maximum diameter.

All the aforementioned generated waves transmit in the form of longitudinal waves in the concrete material. Waves having a comparatively large amount of energy other than those include a wave that transmits in the form of a longitudinal wave through a go path in the concrete material and in the form of a transverse wave through the return path. Generated waves 109*a*, 109*b*, 1210*a*, and 110*b* are such a wave.

That is, the generated waves 109*a* and 109*b* take the path of the generated wave 96*a* to detour in the form of a transverse wave around in the reinforcing bar, transmitting in the form of a longitudinal wave in a go path in the concrete material and in the form of a transverse wave in the return path. The former is from the position of the minimum diameter and the latter is from the position of the maximum diameter.

The generated waves 110*a* and 103*b* take the path of the generated wave 97*a* to detour in the form of a transverse wave around in the concrete material, transmitting in the form of a longitudinal wave in a go path in the concrete material and in the form of a transverse wave in the return path. The former is from the position of the minimum diameter and the latter is from the position of the maximum diameter.

The generated waves of FIG. 35 obtained as the results of the aforementioned measurement indicate low-frequency component waves having a center frequency of 690 kHz. At such a level of frequency, for the reflected waves from the deformed reinforcing bar and the detouring waves, a wave from the position of the minimum diameter is superimposed upon one from the position of the maximum diameter, respectively.

As described above, the generated waves of FIG. 35 were obtained with the peak 91 as the superimposition of the generated wave 101*a* upon the generated wave 101*b*, the peak 92 as the generated wave 102 itself, the peak 93 as the superimposition of the generated wave 103*a* upon the generated wave 103*b*, the peak 94 as the superimposition of the generated wave 104*a* upon the generated wave 104*b*, the peak 95 as the superimposition of the generated wave 105*a* upon the generated wave 105*b*, the peak 96 as the superimposition of the generated wave 106*a* upon the generated wave 106*b*, and the peak 98 as the superimposition of the generated wave 108*a* upon the generated wave 108*b*. In FIG. 35, the generation of the superimposed wave of the generated waves 109*a* and 109*b* and the superimposed wave of the generated waves 110*a* and 110*b* was not found; however, the generation was often recognized in other measurements of the same type.

Accordingly, various values can be determined for the type of the reinforcing bar as follows. First, from the time of generation of the peaks 91 and 93, the maximum diameter can be determined as the following equations 34 and 35.

$$\Delta t = 30.9 - 23.3 = 7.6 \tag{34}$$

$$\Phi = \frac{7.6 \times 5.9}{2} = 22.4 \text{ (mm)} \tag{35}$$

A value of "l" of the maximum position that is obtained from the Snell's law is 22.5 mm, which is highly accurate.

In addition, from the time of generation of the peaks 91 and 94, the maximum diameter can be determined as the following equation 32 using the equation 17.

$$\Delta t = 33.5 - 22.0 = 11.5 \tag{36}$$

$$\Phi = 11.5 \times \frac{5.9}{\pi} = 21.6 \text{ (mm)} \tag{37}$$

Furthermore, from the time of generation of the peaks 91 and 95, the maximum diameter can be determined as the following equations 38 and 39.

$$\Delta t = 37.2 - 22.0 = 15.2 \tag{38}$$

$$\Phi = 15.2 \times \frac{4.44}{\pi} = 21.5 \text{ (mm)} \quad (39)$$

An actual maximum diameter is 21.5 mm, which is highly accurate.

Furthermore, from the time of generation of the peaks 91 and 96, the minimum diameter can be determined as the following equations 40 and 41.

$$\Delta t = 39.3 - 22.0 = 17.6 \quad (40)$$

$$\Phi = 17.6 \times \frac{3.2}{\pi} = 18 \text{ (mm)} \quad (41)$$

Furthermore, from the time of generation of the peaks 91 and 97, the minimum diameter can be determined as the following equations 42 and 43.

$$\Delta t = 41.3 - 22.0 = 19.3 \quad (42)$$

$$\Phi = 19.3 \times \frac{4.44 \times 0.68}{\pi} = 18.5 \text{ (mm)} \quad (43)$$

As described above, the thickness of the covering and the shape of the reinforcing bar can be measured with an extremely high accuracy. Therefore, it is possible to determine whether the reinforcing bar is a round reinforcing bar or a deformed reinforcing bar. Incidentally, the presence or absence of the generation of the peak 92 may be alternatively used to determine whether the reinforcing bar is a deformed reinforcing bar or a round reinforcing bar.

Furthermore, for a corroded reinforcing bar in a concrete material, ultrasonic waves do not transmit inside the reinforcing bar, never causing the peaks 93, 94, and 96 of the aforementioned measurement to be generated. Accordingly, it is possible to determine the level of corrosion of the reinforcing bar in accordance with the strength of the peaks. This makes the present invention highly useful from the viewpoint of maintenance and protection of the concrete material.

Furthermore, for a member such as a polyvinyl chloride pipe being embedded in the concrete material, it is also possible to measure the depth of the buried member and the diameter thereof.

Incidentally, this embodiment of measurement is to determine an arithmetic mean wave using the four jigs in accordance with the equations 19 and 20. In this case, the equation 44 is used instead of the equations 21 and 22 for the frequency of the component wave to be amplified by arithmetic averaging.

$$f \approx \frac{10^6 \times V}{\frac{1}{2}\Delta L} \quad (44)$$

where $\Delta L$ is the difference between the maximum and minimum distances between the transducers. Suppose that the ultrasonic wave in the aforementioned concrete material 81 is a longitudinal wave having a transmission velocity of 4.44(mm/$\mu$s) and the equivalent sound velocity of a direct wave and the like for transmitting between the transducers is 2.7 to 3.5 (mu/$\mu$s). In this case, assuming that $\Delta L = 490 - 400 = 90$ (mm), the frequency for amplifying the direct wave 35, the surface wave 37a, a longitudinal wave 37b and the like can be determined by the following equations 45 to 48. Incidentally, these waves make it difficult to identify the reflected waves 34 and 36 being detected and thus should essentially be eliminated. On the other hand, the equations 45 and 46 indicate those of the longitudinal wave 37b, while the equations 47 and 48 indicate those of the surface wave 37a and the direct wave 35.

$$\Delta t = \frac{9/2}{4.44} = 1.0 \quad (45)$$

$$f_B = \frac{10^6}{1.0} = 1000 \text{ (kHz)} \quad (46)$$

$$\Delta t = \frac{9/2}{2.7 \sim 3.5} = 1.3 \sim 1.7 \quad (47)$$

$$f_B = \frac{10^6}{1.3 \sim 1.7} = 590 \sim 770 \text{ (kHz)} \quad (48)$$

The aforementioned waves that should be eliminated are theoretically amplified at a frequency f of 590 to 770 kHz. Generated waves of such waves, when amplified, cause the reflected waves 34 and 36 being detected to be buried and thus made undetectable. However, in the aforementioned example of measurement, a broadband frequency component having a center frequency of 680 kHz was gained and thereby the generation of the desired peaks 91 to 97 were allowed to appear in a significantly distinct manner. Incidentally, though not illustrated, the same holds for a center frequency of 1,200 kz. This is because of the following reasons.

Figure 37:
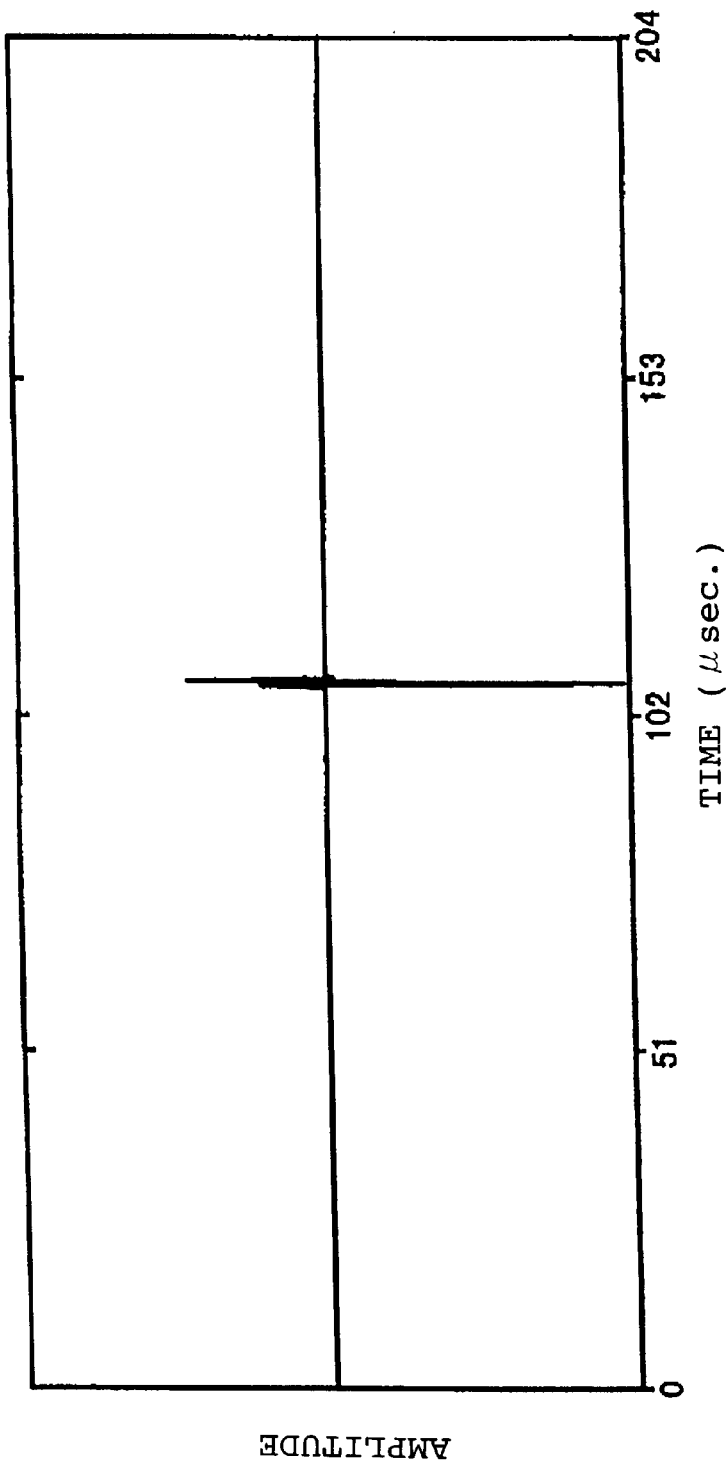
FIG. 37 is a graph illustrating a time series wave of a broadband frequency component gained from input ultrasonic waves with the center frequency being at 1100 kHz.
Figure 38:
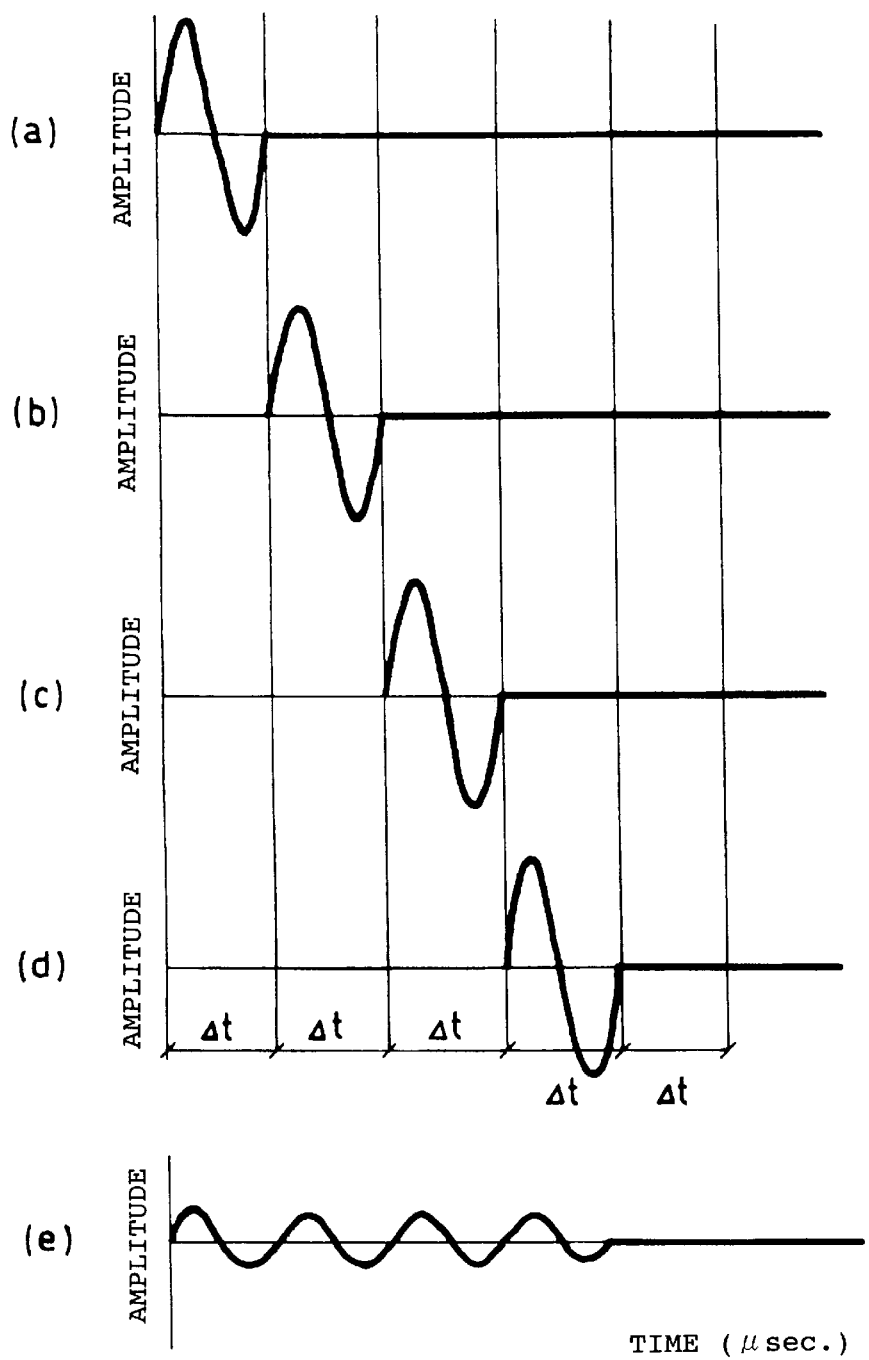
FIGS. 38(a) through (d) are schematic views illustrating waves obtained when each jig is used and 38(e) is a schematic view illustrating their arithmetic mean.

FIG. 37 is a graph illustrating a time series wave of a broadband frequency component gained from input ultrasonic waves with the center frequency being at 1100 kHz. As shown in FIG. 37, the wave has generally one cycle ($\mu$s). After having been input into a concrete material, this ultrasonic wave transmits and then received by a receiving transducer or the like, while being reflected, refracted, and subjected to mode conversion, and attenuated. At this time, the aforementioned one-cycle input wave is attenuated and diminished in amplitude to yield a 1,100 kHz component wave of a received wave.

Accordingly, for such a component wave of only about one cycle, those frequency component waves having a frequency equal to or higher than the frequency determined by $\Delta L$ are not amplified even when the arithmetic averaging is performed in accordance with the equation 19 or 20.

FIGS. 38(a) through (d) are schematic views illustrating waves obtained when each jig is used and 38(e) is a schematic view illustrating their arithmetic mean. In the aforementioned measurement, as shown in FIG. 38(e), the direct wave or the like included in the arithmetic mean $y_{ave}(t)$ resulting from the arithmetic averaging that is performed on four waves in accordance with the equation 20 is one-fourth the original wave in amplitude. Furthermore, referring to FIG. 35, the result is raised to the second power to be displayed, thereby making its apparent amplitude $(1/4)^2 = 1/16$.

On the other hand, concerning the reflected wave or the like from the reinforcing bar being detected, when a distance of 40 mm between the transducers is varied three times each by $\Delta L = 3$ mm and-thereby becomes 49 mm, the amount of variation $\Delta L$, is determined by the following equation 49.

$$\Delta L_t = \sqrt{50^2 + \left(\frac{40+9}{2}\right)^2} - \sqrt{50^2 + \left(\frac{40}{2}\right)^2} = 1.83 \text{ (mm)} \quad (49)$$

Accordingly, the frequency corresponding to this is expressed by the following equations 50 and 51.

$$\Delta t = \frac{1.83/2}{4.44} = 0.20 \quad (50)$$

$$f_A = 5.0 \text{ (MHz)} \quad (51)$$

Thus, the reflected wave from the reinforcing bar being detected will have the minimum amplitude at about 2.5 MHz or one-half of 5.0 MHz, and subsequently will be amplified as the wave is shifted toward lower frequencies.

From this, it is possible to recognize the generation of waves such as reflected waves and detouring waves, which pass through the reinforcing bar being detected, with considerably high accuracy if broadband component waves are gained at a given center frequency within the range of $\alpha f_B$ to $(\frac{1}{2})f_A$.

By the aforementioned third embodiment, a plurality of jigs are employed. In that case, the surface and direct waves that interfere with detection would be eliminated most efficiently in a low-frequency region by gaining a component wave from the arithmetic mean wave at a center frequency of one-half of the value of "f" of the equation 44. The reason for this is described below.

Figure 39:
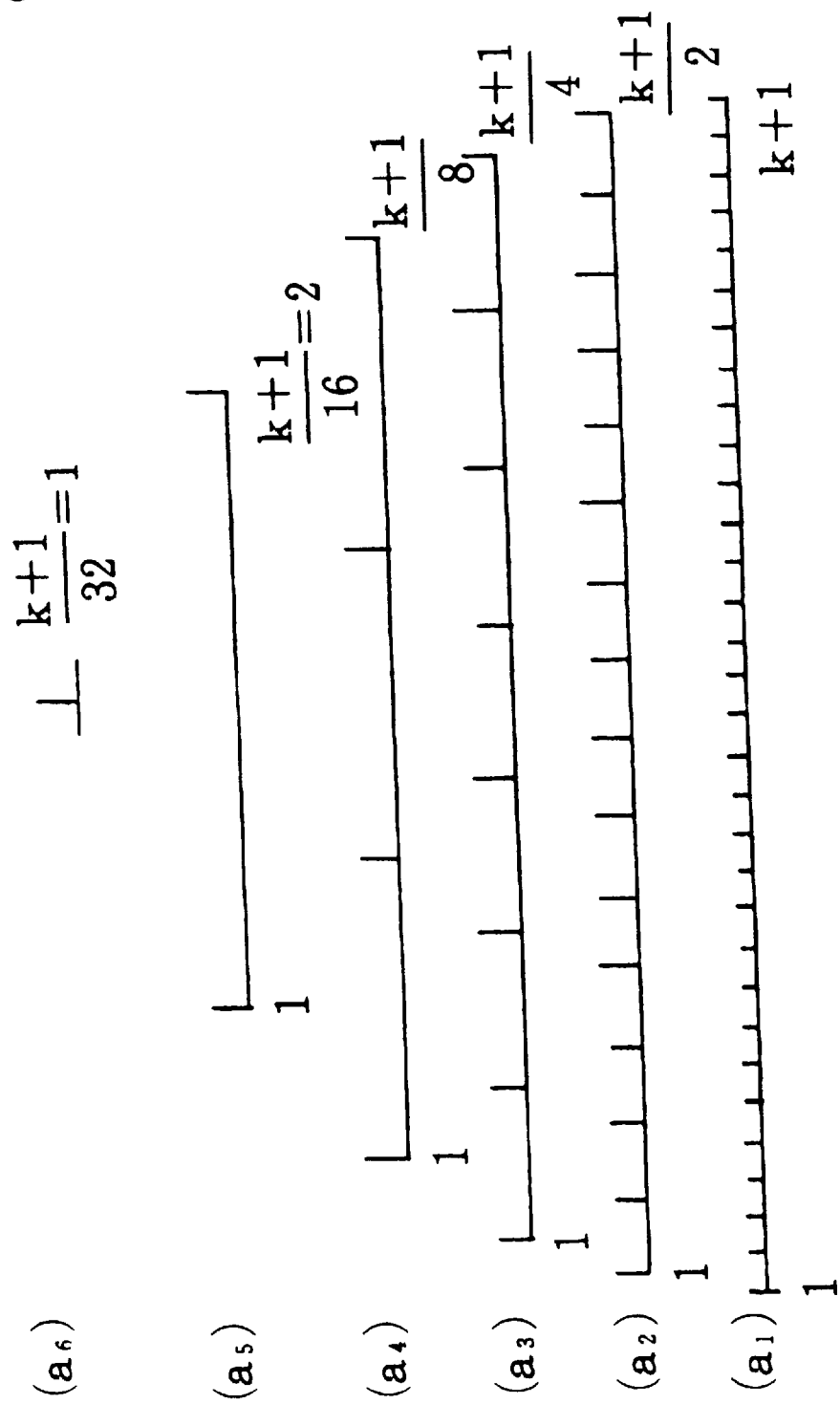
FIG. 39 is a view illustrating the procedure of arithmetic averaging according to equation 20.

Consider the (k+1) arithmetic mean waves that use $D_1$, $D_2$, ... $D_{k+1}$, shown in FIG. 21. It is assumed that the component waves having a given frequency of these arithmetic mean waves have substantially the same strength. FIG. 39 is a view illustrating the procedure of arithmetic averaging according to the equation 20. The lowermost stage ($a_1$) shows the measurement position of the (k+12) arithmetic mean waves. Instead of determining the arithmetic mean of these arithmetic mean waves in accordance with the equation 20, arithmetic averaging is performed on the adjacent arithmetic mean waves, thereby determining (k+1)/2 arithmetic mean waves as in ($a_2$). Repeating this processing will provide ($a_1$)→($a_2$)→($a_3$) ... →($a_6$) in sequence.

Figure 40:
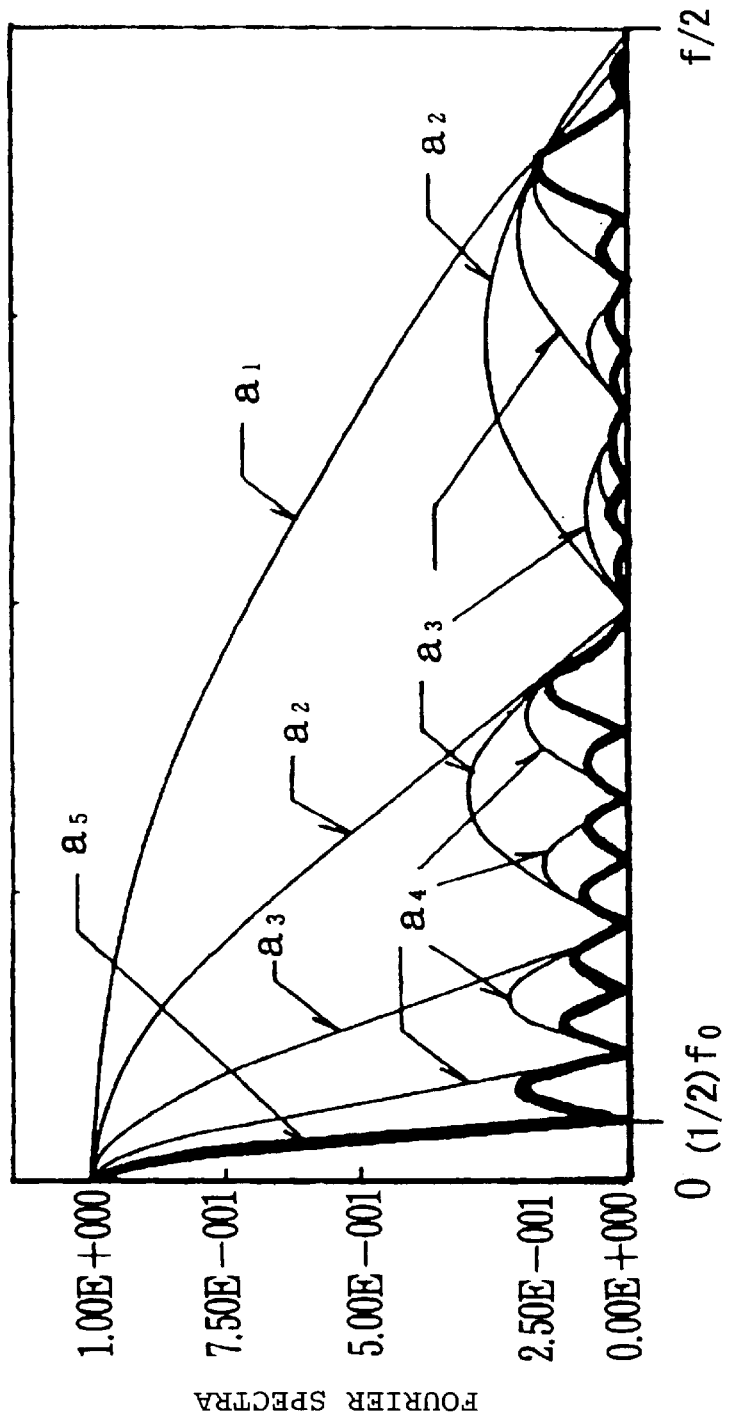
FIG. 40 is a graph illustrating changes in spectrum.

The wave obtained at the last stage ($a_6$) is the arithmetic mean wave shown in the equation 20. Assuming that each of the component waves of the arithmetic mean waves at the stage ($a_1$) has the same amplitude, FIG. 40 shows how the spectrum of the arithmetic mean waves at each stage changes. The figure is expressed with the spectrum value at the stage ($a_1$) being taken as 1.0 over the entire frequency band. The spectrum $a_1$ is the arithmetic mean wave at the stage ($a_2$) and shows the frequency region of 0 to ($\frac{2}{3}$)f in the spectrum of FIG. 28. The frequency ($\frac{1}{2}$)f is the frequency at which the surface and direct waves that interfere with detection at the stage ($a_2$) are eliminated most efficiently from the arithmetic mean waves in the low-frequency region.

Now, the arithmetic mean wave spectrum at the next stage ($a_3$) is as in $a_2$. Similarly, the arithmetic mean wave spectrum at the stage ($a_4$) is as in $a_3$. Finally, the arithmetic mean wave spectrum at the stage ($a_6$) is obtained as shown by a bold line in $a_5$.

The $f_0$ value from the ($\frac{1}{2}$)$f_0$=f/32 shown in the figure corresponds to the f value shown by the equation 44. For this reason, the following equation 52 is defined in place of the equation 44.

$$f_0 = \frac{10^6 \times V}{\frac{1}{2}\Delta L} \quad (52)$$

The numerical value of 32 in the foregoing comes from the assumption that jigs are 32 in number. Accordingly, jigs that are 128 in number would cause the aforementioned numerical value of 32 to be changed to 128.

The aforementioned explanation was made for a measurement using a number of (32) jigs with the $D_i$ and $D_{i+1}$ jigs being different by $\Delta l$ in length.

It is possible to obtain perfectly the same effect as in the aforementioned measurement without using such jigs by carrying out the scanning of the transducers shown in FIGS. 3 and 6 in a manner such that the distance between the transducers has he minimum value of $l_1$ ad the maximum value of $l_M$, and is changed at a constant velocity.

In this case, $\Delta L$ to be applied to the equation 52 is given by equation 53.

$$\Delta L = l_M - l_1 \quad (53)$$

On the other hand, in the aforementioned processing of arithmetic averaging, consider the spectrum of reflected waves of a detected target such as a plate thickness.

This is explained using the measurement diagram of FIG. 24. Referring to the figure, letting d be the plate thickness, the maximum path length of 201 is $\{(l_M/2)^2 + d^2\}^{1/2}$ and the minimum path length is $\{(l_1/2)^2 + d^2\}^{1/2}$. Letting $\Delta L_B$ be the difference between the path lengths, the lowest frequency at which the component wave of the plate thickness reflected wave disappears is expressed by the following equation 52 in accordance with the equation 52 in the same manner as in the foregoing.

$$\frac{1}{2}f_B = \frac{10^6 \times V}{\frac{1}{2}\Delta L_B} \quad (54)$$

Figure 41:
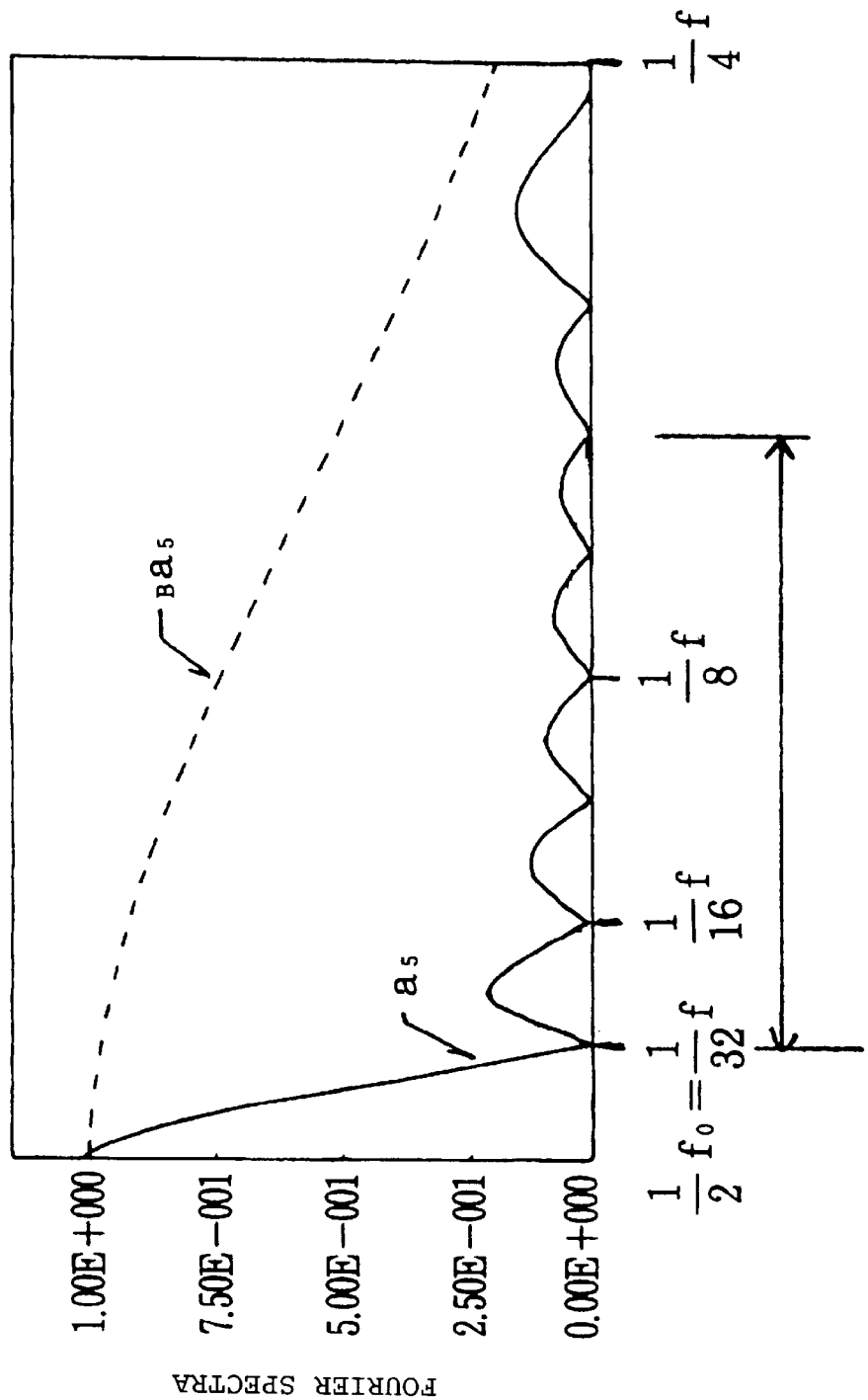
FIG. 41 is a graph illustrating spectra $_B a_5$ and $a_5$.

Accordingly, it is possible to obtain the spectrum of the plate thickness reflected waves with the vale of "If" of FIG. 40 being replaced by $f_B$. Letting $l=l_M-l_1$, if the relationship holds that d>>21 between "l" and "d", the value of $f_B$ is extremely greater than the value of "f". A spectrum corresponding to the $a_5$ spectrum of FIG. 40 is determined using the value of $f_B$ and taken as $_Ba_5$, and FIG. 41 shows the $_Ba_5$ and $a_5$ together. This $_Ba_5$ is a normalized spectrum of the 201 path wave of the arithmetic mean wave that is finally obtained. At the frequency band shown by "⇋" of FIG. 41, the spectrum $_Ba_5$ of the 201 path wave being detected is significantly prominent relative to the 202 and 203 surface waves and the 204 direct wave, which interfere with detection. By gaining a time series wave in this frequency band, this makes it possible to obtain a wave, in which only the 201 path wave is extremely prominent, with no mistake.

A measurement which is carried out using the aforementioned equations 52 and 53 is shown as a fourth embodiment. In the second embodiment, arithmetic averaging was performed 10,000 times in accordance with the transducer scanning method shown in FIG. 6, and the arithmetic mean wave was obtained as shown in FIG. 7. The measurement to be shown corresponds to this measurement. The measurement is carried out by the scanning of FIG. 6, with L=15 cm, the maximum distance being 15 cm and the minimum distance being 10 cm between the transducers, and the velocity being made constant for varying the distance. FIG.

42 shows the arithmetic mean wave that is obtained with the transmitting and receiving transducers having an oscillator 40 mm in diameter whose resonant frequency of 500 kHz.

Figure 42:
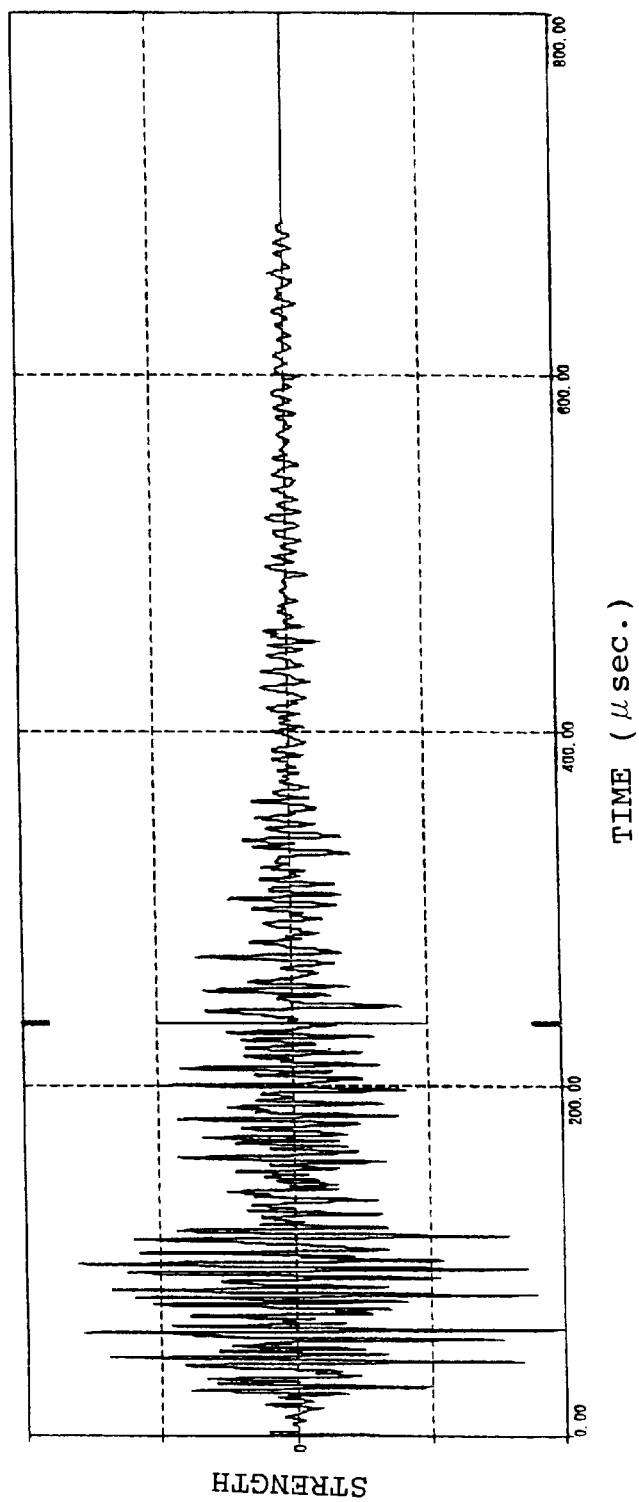
FIG. 42 is a graph illustrating an arithmetic mean wave obtained when both transmitting and receiving transducers have an oscillator 40 mm in diameter whose resonant frequency of 500 kHz.
Figure 43:
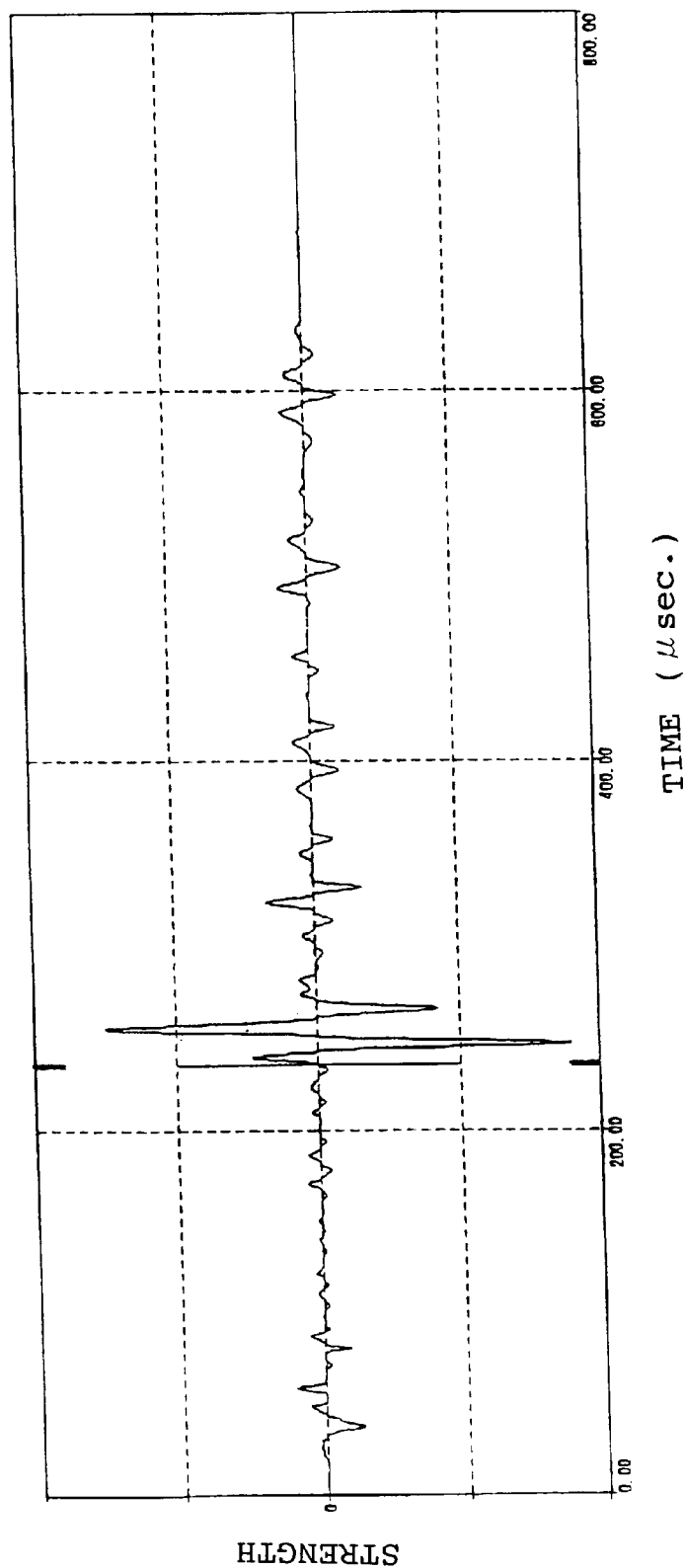
FIG. 43 is a graph illustrating a component wave gained by applying equations 52 and 53 to the arithmetic mean wave of FIG. 42 with the frequency shown in the following equation 55 being employed as the center frequency.

FIG. 43 illustrates a component wave gained by applying the equations 52 and 53 to the arithmetic mean wave of FIG. 42 with the frequency shown in the following equation 55 being employed as the center frequency.

$$\frac{1}{2}f = \frac{\frac{1}{2} \times 10^6}{\frac{1}{2}\Delta L/\bar{V}} \quad (55)$$

Here, the equation 55 is rewritten as the following equation 56, based on the longitudinal-wave sound velocity in-the concrete being 4,300 m/s and assuming that the surface and direct waves, which interfere detection, vary in its equivalent sound velocity within the range of 3,000 to 4,000 m/s and thus have an average velocity of 3,500 m/s.

$$\frac{1}{2}f = \frac{\frac{1}{2} \times 10^6}{\frac{1}{2}(150-100)/3.5} = 70 \text{ (kHz)} \quad (56)$$

When compared with those in FIG. 42, most of the surface, direct, and scattered waves, which interfere with detection, are eliminated in FIG. 43, making it possible to clearly recognize the reflected wave of A'-B' path. Incidentally, the arithmetic averaging was performed 3,000 times in this measurement.

On the other hand, FIG. 44 shows the method that is considered as a method for scanning transducers without measuring jigs. FIG. 44(a) illustrates the method shown in the fourth embodiment. FIG. 44(d) illustrates a method for scanning two transducers at a constant velocity in either straight-line or curved-line scanning manner, at random within the movement region 7 of FIG. 3 and 11a and 11b of FIG. 6, from the points C to D as shown in FIG. 11 along immediately above the subject being detected, with the distance between the transducers being fixed. On the other hand, FIG. 44(b) shows two transducers brought into contact with each other in the scanning method shown in FIG. 44(d). FIG. 44(c) illustrates a measurement with one transducer, showing a method for scanning one transducer, serving as the transmit receiving transducers, at a constant velocity (in either straight-line or curved-line scanning manner), at random within the circular region 7 of FIG. 3 (alternatively within an elliptical or a rectangular region), from the points C to D as shown in FIG. 11 along immediately above the subject being detected.

Figure 45:
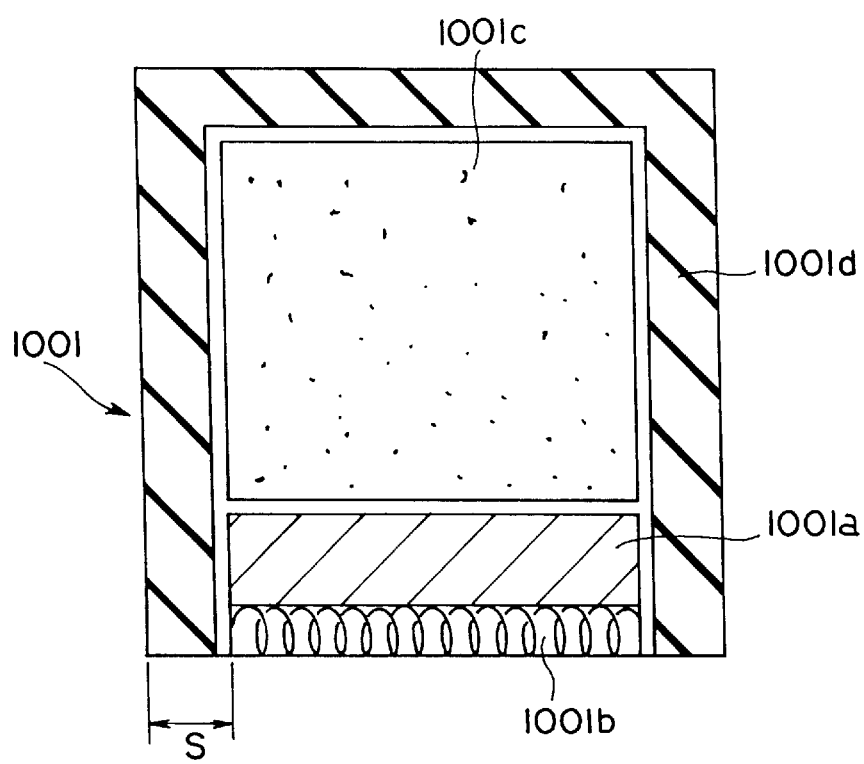
FIG. 45 is a cross-sectional view illustrating the typical shape of a longitudinal-wave transducer.

For each of the aforementioned scanning methods, it is shown below how the equation 52 looks like. It is first explained that a limit value of a predetermined amount exists commonly with respect to the scanning methods shown in FIGS. 44(a) to (d) in the value of "$f_0$" of the equation 52 indicating the frequency at which the surface and direct waves, which interfere with detection, are eliminated most efficiently in a low-frequency region. A general shape of a longitudinal-wave transducer is shown in FIG. 45. With such a transducer being employed as a receiving transducer, the received wave is mixed with a component wave excited at the resonant frequency of $f_p$ of an outer sheath. A transducer 1001 is provided with an oscillator 1001a, a protective material 1001b for protecting the contact face of a detected material, an attenuating material 1001c, and an outer sheath 1000d. With one-half of the value of $f_0$ defined by the equation 52 being consistent with this $f_p$ and a component wave being gained at a center frequency of (½)$f_0$, the component wave is superimposed upon an excited wave at the resonant frequency of the outer sheath 1001d. This makes it necessary to avoid gaining a component wave at such a frequency. According to a number of experimental measurements, it has been found that the value of $f_0$ should be given by the following equation 57 to avoid this. Incidentally, the letter "S" shown in the figure designates the thickness of the outer sheath.

$$f_0 = 4f_P \quad (57)$$

Now, it is adjusted how the right-hand side ΔL of the aforementioned equation 52 is expressed for each scanning method.

For the scanning method shown in FIG. 44(a) because of the reason described in the fourth embodiment, the ΔL is determined in accordance with the equation 53 and then applied to the equation transducer 52 to determine $f_0$. Incidentally, with $f_0 < 4f_P$, it may be employed that $f_0 = 4f_P$. In other words, ΔL my be changed to ΔL=$10^6$V/(2$f_p$) to determine $f_0$.

For the scanning method shown in FIG. 44(d), ΔL is applied to the equation 52 to determine $f_0$, letting $\Phi_2$ be the diameter of the oscillator inside the receiving transducer as shown in the following equation 58, assuming that the receiving transducer consists of a set of small transducers and because of the reasons described in the fourth embodiment. However, expressing that $f_0 = 4f_P$ at $f_0 < 4f_P$ and changing ΔL to ΔL=$10^6$V/(2$f_p$) may be allowed to determine $f_0$.

$$\Delta L = \Phi_2 \quad (58)$$

Incidentally, in the method in which an arithmetic mean wave is determined for each jig for holding the distance between the two transducers shown in the third embodiment, using the scanning method shown in FIG. 44(d), to determine the arithmetic mean of these two arithmetic mean waves, ΔL may be given as in the following equation 59 using the difference Δl in length between the two jigs. This ΔL is applied to the equation 52 to determine $_0$. However, expressing that $f_0 = 4f_P$ at $f_0 < 4f_P$ and changing ΔL to ΔL=$10^6$V/(2$f_p$) may be allowed to determine $f_0$.

$$\Delta L = 2 \times l \quad (59)$$

For the scanning method shown in FIG. 44(b), as shown in the following equation 60, the ΔL used in the equation 52 may be employed as the predetermined amount $G_1$, which is defined by the material of the body being detected, the diameter of the oscillator in the transducers, the thickness of the outer sheath of the receiving transducer, and the resonant frequency of the outer sheath.

$$\Delta L = G_1 \quad (60)$$

For the scanning method shown in FIG. 44(c), as shown in the following equation 61, the ΔL used in the equation 52 may be employed as the predetermined amount $G_2$, which is defined by the material of the body being detected, the diameter of the oscillator in the transducers, the thickness of the outer sheath of the receiving transducer, and the resonant frequency of the outer sheath.

$$\Delta L = G_2 \quad (61)$$

Shown below is the amount given to the predetermined amount $G_1$ in the aforementioned scanning method shown in FIG. 44(b).

Figure 46:
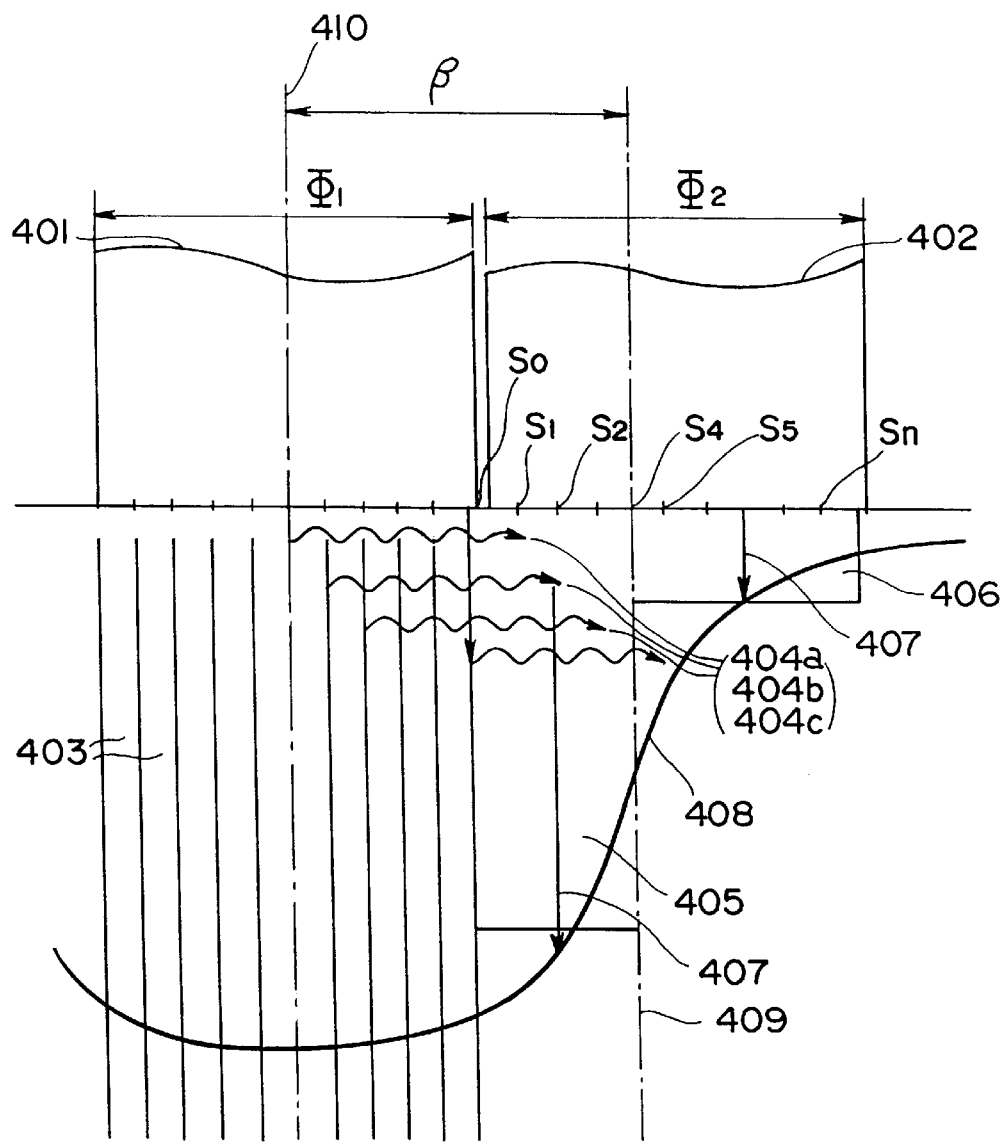
FIG. 46 is a schematic view illustrating the manner of transmission of longitudinal ultrasonic waves input to a concrete material from a surface thereof directly downwards.

FIG. 46 is a view illustrating a longitudinal wave 404a, a transverse wave 404b, and a surface wave 404c, transmitting on a concrete surface to a receiving transducer 402, with a longitudinal ultrasonic wave 403 being input to the concrete surface directly downwards from a transmitting transducer 401. Here, the figure is drawn, letting the thickness S of the outer sheath of the transducers be zero.

Reference numeral 407 schematically indicates the strength of the combined wave of the waves 404 produced for each transmit ultrasonic wave of 403, which is discretely indicated. Reference numeral 408 is an envelope of these strengths, illustrating the aforementioned combines wave being suddenly attenuated. Following the introduction of the equation 52 showing a value two times greater than the frequency at which the component such as the surface and direct waves, which interfere with detection, is reduced to a minimum in the low frequency region, such an assumption has to hold for the receiving transducer of FIG. 46 that the strength of each of the frequency component waves, received at the discrete reception points $S_0, S_1, S_2, \ldots S_n$, is generally equal to each other. To satisfy the condition, a dotted line 409 was set, the reception points were divided into two regions 405 and 406, and then it was assumed in the figure that the strength of received component waves at the $S_0$ to $S_4$ was equal to each other and the strength of received component waves at the $S_5$ to $S_n$, was equal to each other. Here, the distance between the aforementioned dotted line 409 and a center line 401 of the transmitting transducer was defined as β.

Then, the strength of the component wave of the region 405 is compared with that of the region 406 to neglect the latter since the former is extremely larger than the latter. Assuming that the reception points $S_0, S_1, \ldots S_4$ are each a receiving transducer of a small diameter and due to the reason shown in the fourth embodiment, the predetermined amount $G_1$ of the equation 60 for determining the frequency (½) $f_0$ of the lowest-frequency component wave, reduced in strength, of the waves 404a, 404b, 404c, which interfere with detection, can be introduced as in the following equations 62 and 63.

$$G_1 = \beta - \frac{\Phi_1 + 2S}{2} \tag{62}$$

where $\Phi_1$ is the diameter of the oscillator in the transmitting transducer, $\Phi_2$ is the diameter of the oscillator in the receiving transducer, S is the thickness of the outer sheath of the aforementioned transducers, and $f_p$ is the resonant frequency of the outer sheath of the receiving transducer.

Here, it holds that $G_1 = \Phi_2$ when $(\Phi_2 < G_1$.

With the value of $f_0$ obtained by applying the aforementioned $G_1$ to the equations 60 and 52, it holds that $f_0 = 4f_P$ when $f_0 < 4f_P$. In other words, the value of $G_1$ is given by the equation 63.

$$G_1 = \frac{10^6 \times V}{2 \times f_P} \tag{63}$$

Incidentally, it has been found from a number of experimental measurements that the value of β takes on the following numerical values for typical concrete having a strength of 350 to 450 kg/cm².

An oscillator of diameter 40 mm in the transmitting transducer: β=50~53 mm

An oscillator of diameter 76 mm in the transmitting transducer: β=65~68 mm

Furthermore, it is shown below what value is given to the predetermined amount $G_2$ in the scanning method shown in FIG. 44(c). Assuming that the transmitting and receiving transducers are a set of discrete transducers of a small diameter, the predetermined amount $G_2$ can be introduced as in the equation 64, following the introduction of the aforementioned predetermined amount $G_1$ and the introduction of the equations 52 and 53. That is, $$G_2 = \Phi \tag{64}$$

where Φ is the diameter of the oscillator of the transmitting and receiving transducers.

Moreover, letting $f_p$ be the resonant frequency of the outer sheath of the transducer, the value of G2 is given by the equation 65 when it holds for the value of 0 calculated by the equations 52, 61 and 64 that $f_0 < 4_P$.

$$G_2 = \frac{10^6 \times V}{2 \times f_P} \tag{65}$$

Incidentally, the value of $f_0$ obtained by the equation 52 increases when measurements are made using the scanning method shown in FIG. 44(b) or (c). According to the scanning method shown in FIG. 44(b) in which a transducer having an oscillator 40 mm in diameter, a frequency of 500 kHz, and an outer sheath of thickness 10 mm, the equation 66 holds in accordance with the equation 62.

$$G_1 = 50 - \frac{40 + 2 \times 10}{2} = 20 \tag{66}$$

Then, suppose that the average sound velocity of waves, which interfere with detection, is 3,500 to 4,000 m/s in the equation 52 and 60. In this case, the $f_0$ shown in the following equation 67 is obtained.

$$f_0 = \frac{10^6 \times 3.75}{\frac{1}{2} \times 20} = 380 \text{ (kHz)} \tag{67}$$

Consequently, the frequency at which the lowest-frequency waves, which interfere with detection, are reduced to a minimum will be at about $f_0=190$ kHz.

Figure 47:
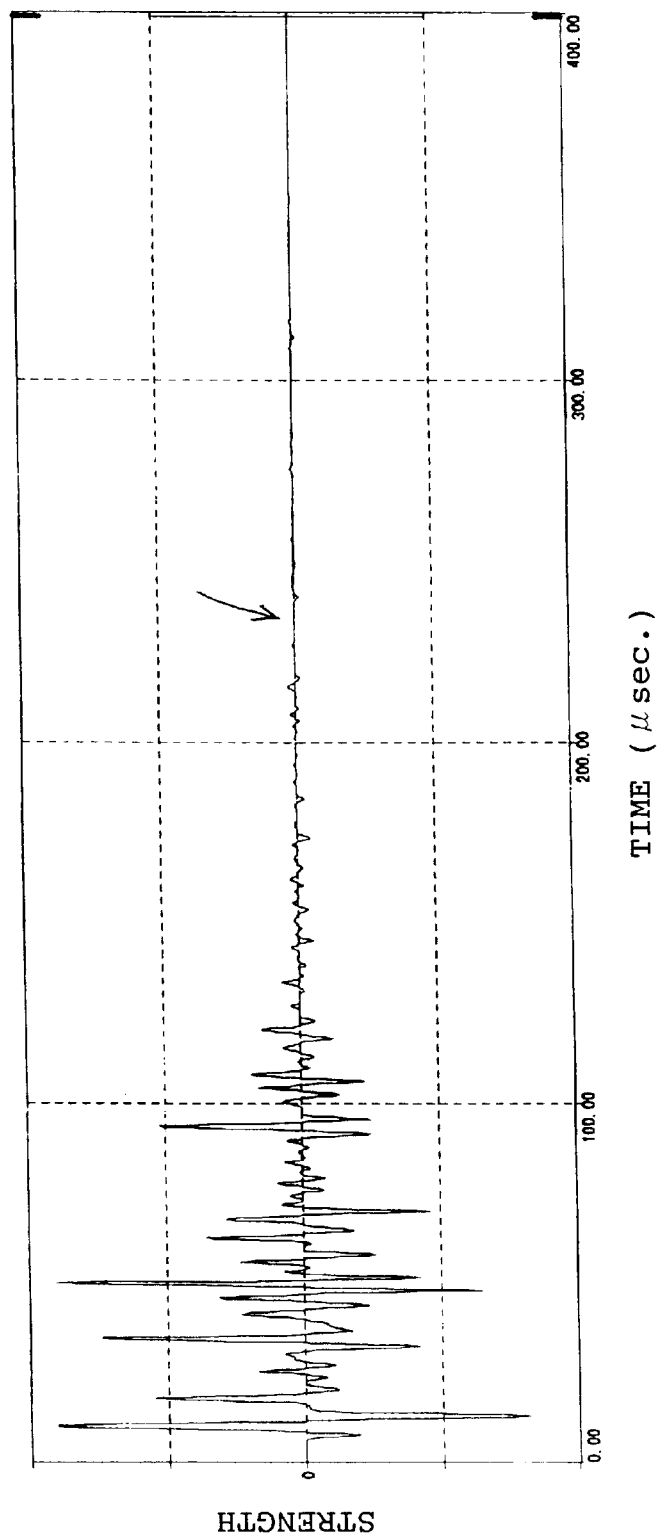
FIG. 47 is a graph illustrating the results of measurement by the method, shown in FIG. 44(b), for scanning the model of concrete of FIG. 72.

It is not rare that the ultrasonic waves in the concrete are acceleratingly attenuated due to the scattering phenomenon as the transmission distance increases, making the attenuation proportional to the second to third power of the transmission distance. In the measurement of plate thickness of 50 cm, 100 cm, or more, it is difficult in some cases to measure the aforementioned waves of a frequency of about 190 kHz due to attenuation caused by scattering. As an example, FIG. 47 illustrates an embodiment of a measurement made at point Δl of the concrete model of FIG. 72 according to the scanning method shown in FIG. 44(b), using the transmitting and receiving transducers having an oscillator 40 mm in diameter and a frequency of 500 kHz. The presence of reflected waves cannot be recognized at the position, indicated by the arrow, where a plate thickness reflected wave is theoretically generated. This is because the remaining surface waves, which interfere with detection, have a relatively larger amplitude than that of the plate thickness reflected wave that is significantly attenuated due to its long transmission distance.

Figure 48:
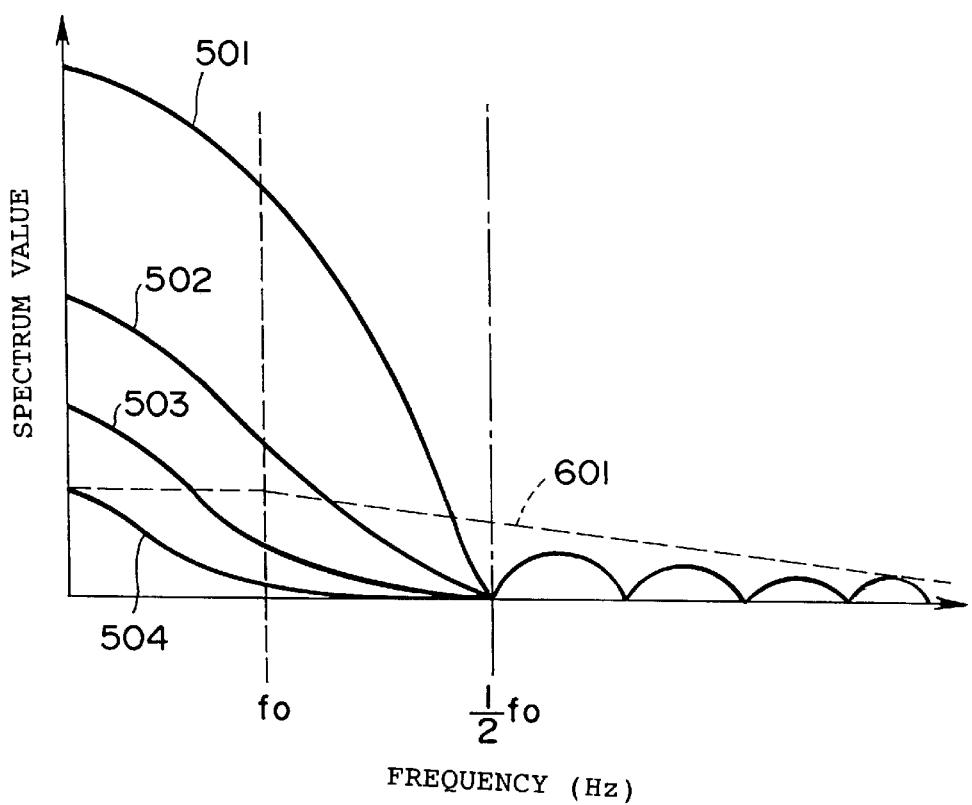
FIG. 48 is a graph illustrating the comparison between the spectra of interference waves interfering detection and waves of targets to be detected such as plate thickness.

FIG. 48 illustrates the comparison between the spectra of interference waves, which interfere with detection, included in such a received wave and of waves of a target to be detected such as a plate thickness.

Designated as 501 is an interfering wave, which interferes with detection, included in an arithmetic mean wave, while designated as 601 is the spectrum of a detection target wave. The interfering wave would be significantly attenuated through a long transmission distance like the detection target wave. Therefore, the time series wave of the spectrum 501 of the interfering wave must be concentrated at an earlier time of generation in the arithmetic mean wave. From this, a time series filter is defined as in the equation 68.

$$G(t) = \sin\left(\frac{\pi}{2} \cdot \frac{t}{t_0}\right) \quad (68)$$

where $t_0$ is defined by the equation 69, letting $\tilde{d}$ be the depth of a target being detected.

$$t_0 = \frac{2\tilde{d}}{V} \quad (69)$$

Multiplying the arithmetic mean wave by to would cause 501 to be reduced to a spectrum 502, and further multiplications would cause 502 to be reduced to 503 and 503 to 504, thus reducing the spectrum values as shown in the figure. At a stage where the spectrum of the interfering wave included in the arithmetic mean wave has been reduced to 504, the detection target wave spectrum 601 is extremely greater than the interfering wave 504 in the range of frequencies of $(\frac{1}{2})f_0$ to $f_D$. Thus, by shifting the center frequency for gaining a component wave from the arithmetic mean wave from $(\frac{1}{2})f_0$ to as low a frequency as possible, the attenuation due to transmission scattering is reduced as the component wave has a lower frequency, thereby possibly causing the detection target wave to emerge. Therefore, $f_D$ is given by the equation 70 using the resonant frequency $f_p$ of the outer sheath of the aforementioned receiving transducer.

$$f_D = 4f_P \quad (70)$$

As described above, to obtain a reflected wave from a deep position using the scanning method shown in FIG. 44(*b*) or (*c*), the value of to, which is determined from a predetermined detected depth $\tilde{d}$, is determined in accordance with the equation 69. The to is applied to the equation 68 and then the aforementioned arithmetic mean wave is multiplied by the resulting time series filter a plurality of times. Then, a center frequency is set within the range of the value of $(\frac{1}{2})f_0$, determined by the combination of the equations 60 and 52 or the combination of equations 61 and 52, to $f_D$ of the equation 70. Then, a component wave is gained while the setting is gradually being shifted from $(\frac{1}{2})f_0$ to $f_D$.

Figure 49:
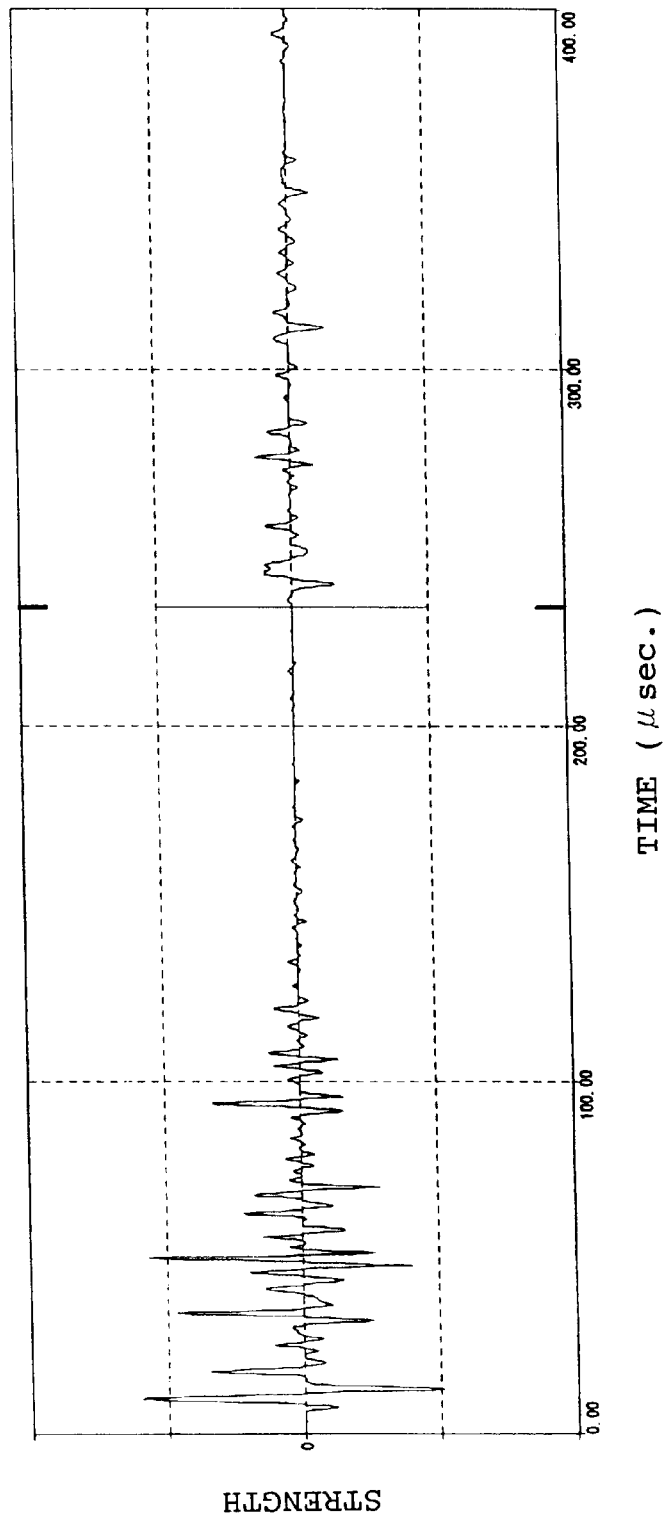
FIG. 49 is a graph illustrating the result of raising a wave or a component wave having a center frequency of 200 kHz of FIG. 42 to the third power.

The acquisition of a reflected wave from a deep position using the aforementioned scanning method shown in FIG. 44(*b*) or (*c*) is shown as a fifth embodiment. Nevertheless, the scanning methods shown in FIGS. 44(*b*) and (*c*) are essentially the same. The fifth embodiment is shown in accordance with the scanning method shown in FIG. 44(b). An explanation is made using an embodiment of measurement of FIG. 42 of the plate thickness reflection with a plate thickness being 50 cm, which employs the concrete model of FIG. 72. FIG. 49 illustrates a wave of FIG. 42 which has a center frequency of 200 kHz and is multiplied three times by a time series filter function G or G(t)=sin (($\pi$/2) (t/400) with a depth to be detected being given about 80 cm, or $t_0$ being given 400 $\mu$s in FIG. 69, which is applied to the equation 68. AT this point in time, something like a plate thickness reflection can be seen at the position indicted by the cursor; however, it is difficult to identify this as a plate thickness reflection. Thus, such an analysis is carried out in which the center frequency for gaining a component wave is gradually shifted from $(\frac{1}{2})f_0$ to $f_D$.

Figure 50:
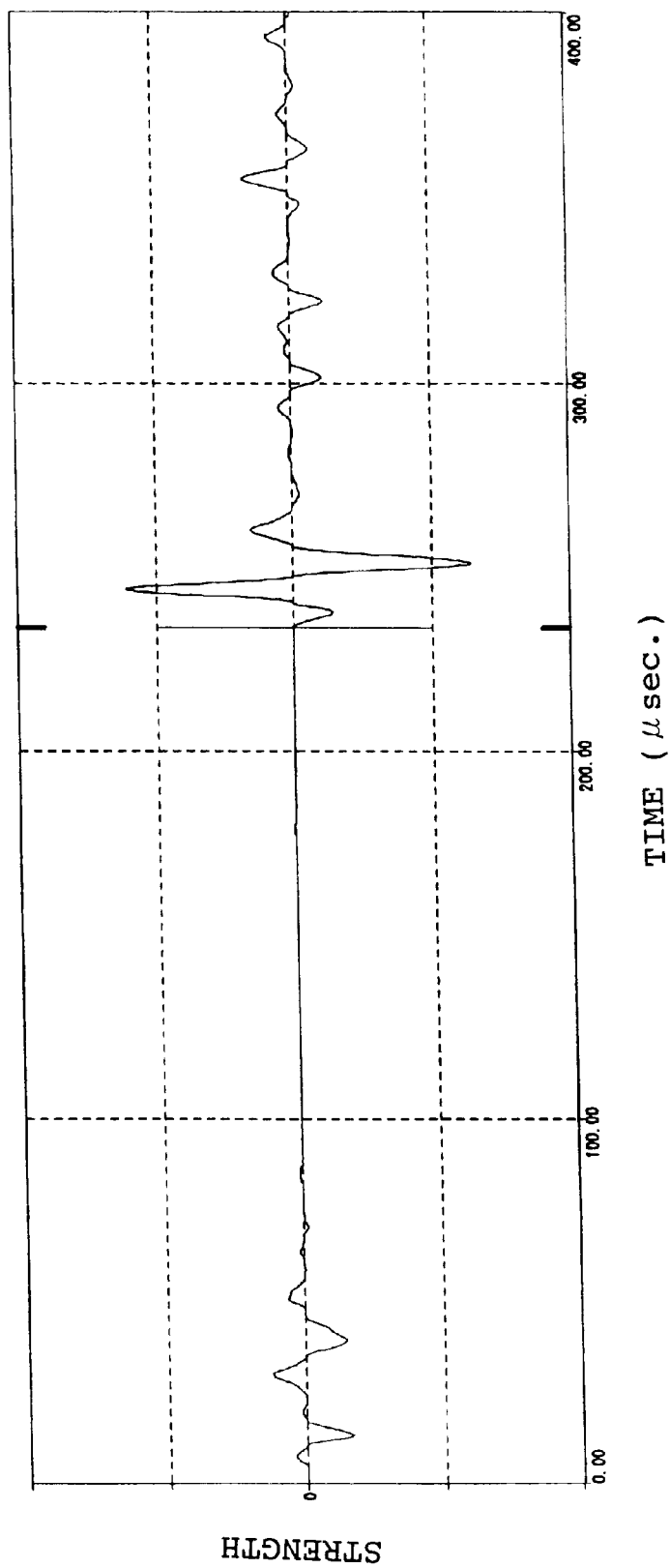
FIG. 50 is a graph illustrating the result of gaining a component wave with the center frequency being at $f_D$=65 kHz.

As described above, $(\frac{1}{2})f_0$ is 190 kHz. The value of $f_D$ is found to be 4×16.5≈65 kHz in accordance with the equation 70 in which the transducers used have a resonant frequency of about 16.5 kHz. Omitting the intermediate course, FIG. 50 illustrates the result of a gained component wave with the center frequency being at $f_D$=65 kHZ. It is possible to recognize, astonishingly in a distinct manner, the plate thickness reflected wave that could not be recognized in the component wave near 200 kH (FIG. 47).

An embodiment of measurement is shown as a sixth embodiment in which the aforementioned component wave gained with center at one-half of $f_0$ is shifted towards high frequencies or low frequencies.

Figure 51:
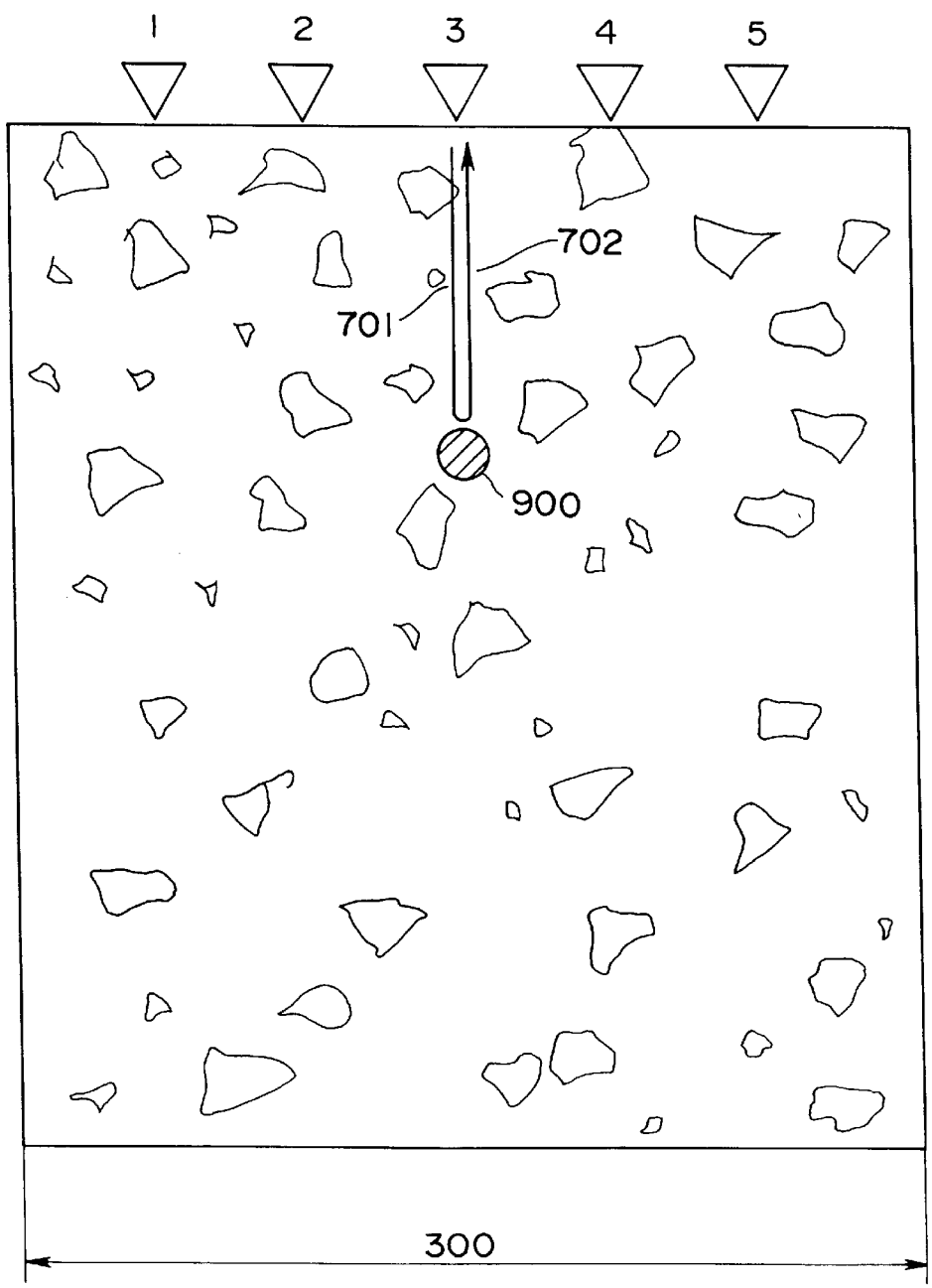
FIG. 51 is a schematic cross-sectional view illustrating a model of concrete used for measurement.

FIG. 51 illustrates a model of concrete used for measurement. The model has a plane of 30 cm×30 cm and a thickness of 35 cm, with a round reinforcing bar 900 of diameter 19 cm being embedded at a position of 10 cm in covering thickness from a surface. At measurement points 1 to 5, using the scanning method shown in FIG. 44(*b*), transducers are scanned across a movement width of 20 cm in parallel to the longitudinal direction of the embedded reinforcing bar. Arithmetic averaging was performed 3,000 times at each point, and both the transmitting and receiving transducers used have an oscillator of diameter 40 mm and a resonant frequency of 1 MHz with each transducer being 60 mm in diameter.

The value of $f_0$ in this measurement is the same as that of the fifth embodiment. That is, $(\frac{1}{2})f_0$=190 kHz.

Figure 52:
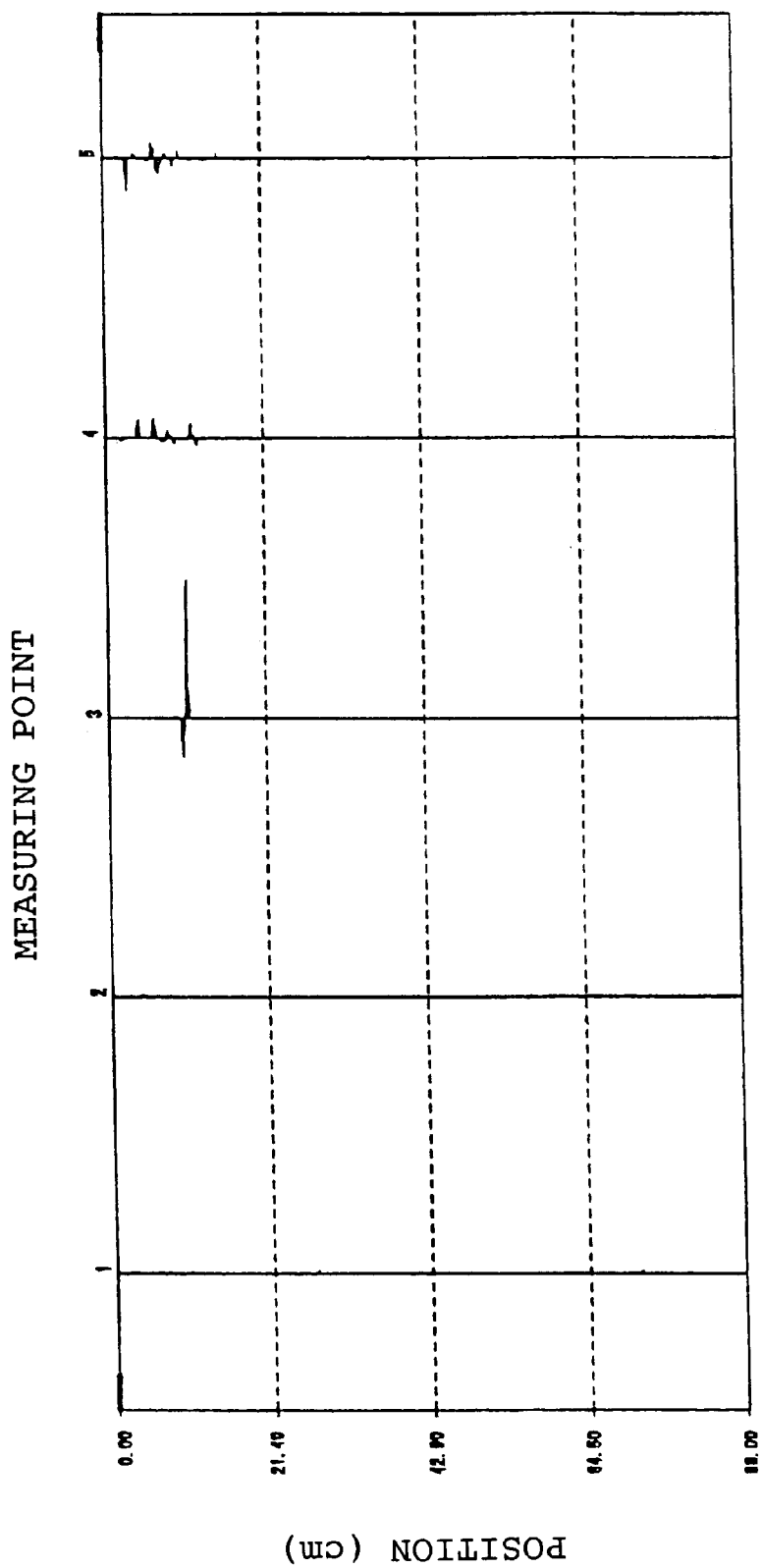
FIG. 52 is a graph illustrating component waves gained at each measurement point with the center frequency being at 190 kHz.
Figure 53:
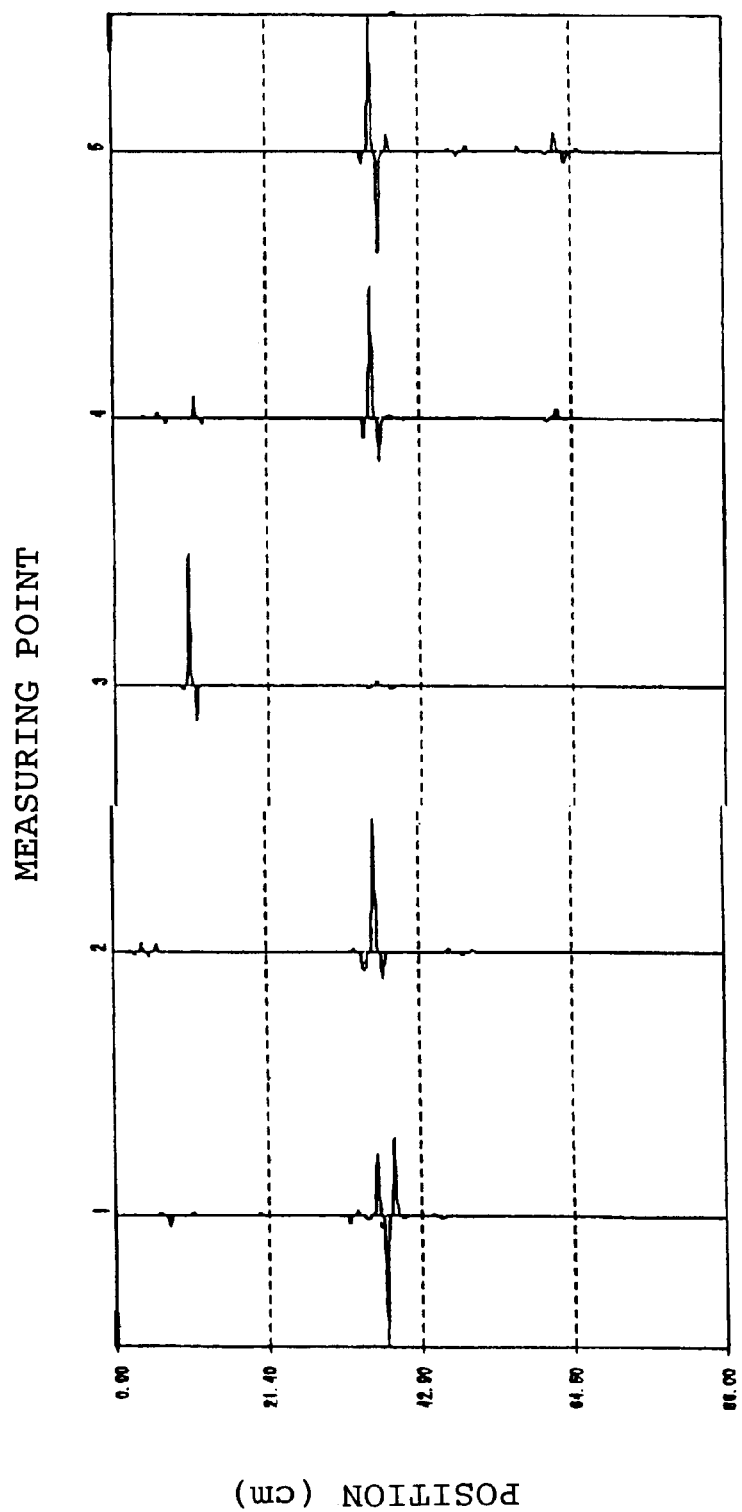
FIG. 53 is a graph illustrating an example obtained in the course of shifting, by filtering, the center frequency employed for gaining a wave obtained by raising each component wave of FIG. 52 to the tenth power.

FIG. 52 illustrates component waves gained at each measurement point with the center frequency being at 190 kHz. At this frequency, an interfering wave has disappeared and only a reflected wave from the reinforcing bar disposed immediately under the measurement point 3 can be distinctly recognized. On the other hand, FIG. 53 illustrates an example obtained in the course of shifting the center frequency for gaining a component wave from the wave that has been obtained by multiplying ten times each component wave of FIG. 52 by the time series filter, G(t)=sin($\pi$t/(2× 230), obtained by applying $t_0$=(2×500/4.3≈230 $\mu$s to the equation 68, the $t_0$ being given by the equation 69 with the depth to be detected being made equal to 50 cm. Here, the center frequency is shifted, by filtering, from the aforementioned $(\frac{1}{2})f_0$ (=190 kHz) to the value (60 kHz) obtained by successively applying the resonant frequency of the outer sheath of the receiving transducer (16.5 kHz for the transducers used) to the equation 70. The example has a gaining center frequency of 150 kHz. Both of the reflected waves from the reinforcing bar and indicative of the plate thickness are allowed to emerge distinctly. This is an example which allows for gaining a reflected wave indicative of the thickness even at frequencies higher than $4f_D$=60 kHz since the thickness is relatively as thin as 35 cm. Incidentally, FIGS. 52 and 53 illustrate a gained component wave that is raised to the fourth power.

By the aforementioned analysis, or in FIGS. 52 and 53, it is possible to measure the planar position of presence and the thickness of the reinforcing bar; then, how the diameter of the reinforcing bar can be measured?

FIG. 52 shows the component wave gained at 200 kHz and FIG. 72 at 150 kHz. It is impossible to acquire reflected waves for recognizing the diameter of the reinforcing bar with component waves of such low frequencies. In this regard, it is necessary to shift the center frequency for gaining a component wave towards higher frequencies. A method employed for this purpose is described.

Figure 54:
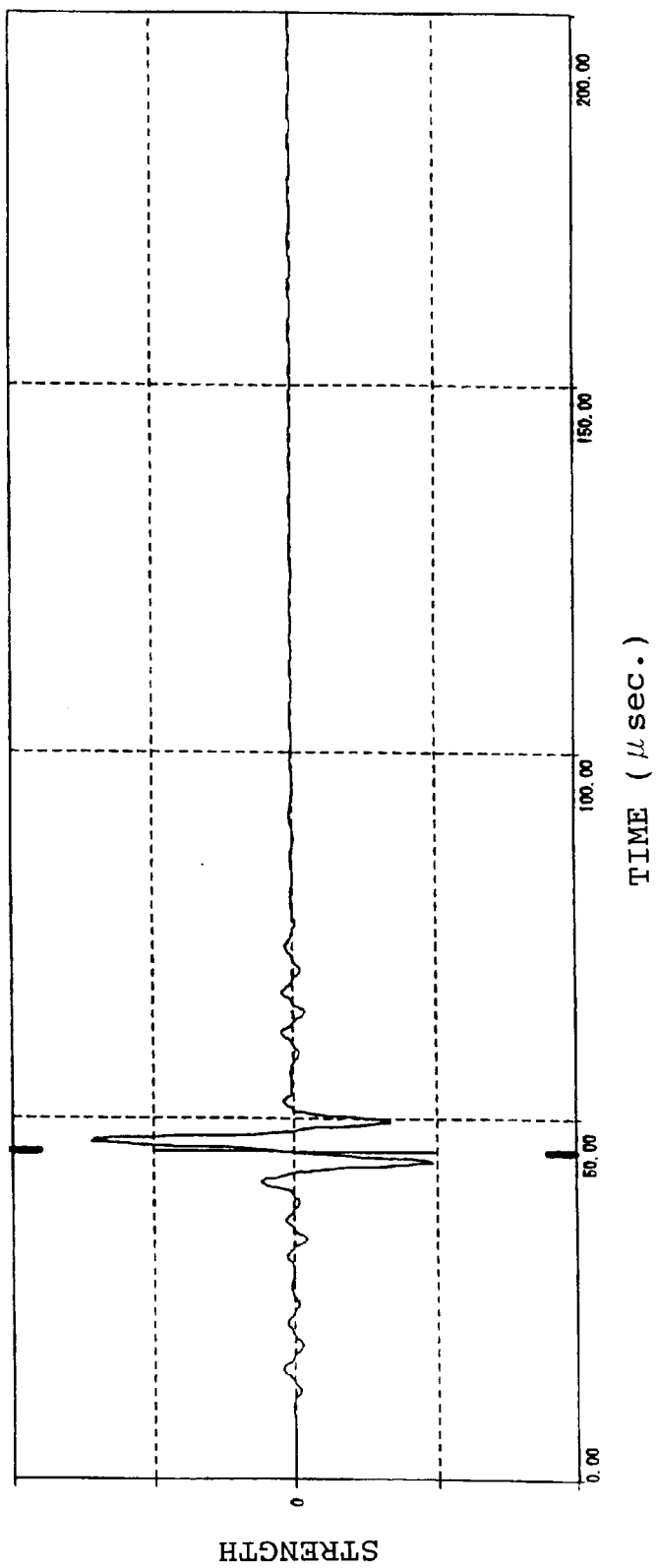
FIG. 54 is a graph illustrating a 200 kHz component wave provided by measurement 3.

FIG. 54 illustrates a 200 kHz component wave provided by measurement 3. Since high-frequency components of a reflected wave from the target being detected are reduced in strength as the depth of the subject being detected becomes comparatively deeper, gaining a high-frequency component will allow an interfering wave, which has disappeared, to relatively emerge.

Figure 55:
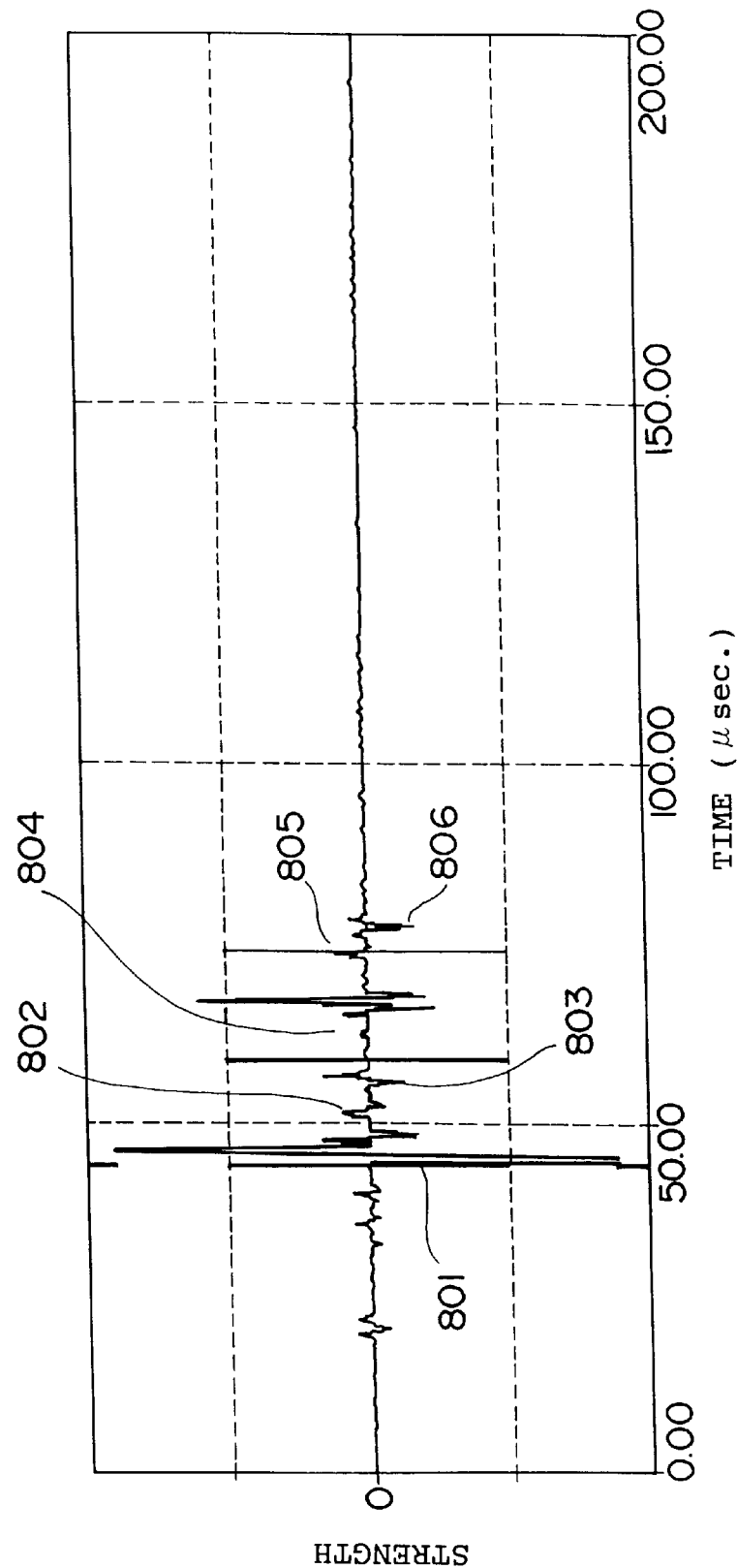
FIG. 55 is a view illustrating an amplified component wave obtained at a center frequency of 680 kHz reached after gradual sweeping of center frequencies towards higher frequencies.

In this regard, prior to sweeping in higher frequencies, the position of the reflected wave from the reinforcing bar of FIG. 54, indicated by the cursor, is designated as to, which is applied to the equation 68 to prepare the time series function G(t), by which the component wave of 200 kHz of FIG. 54 is in turn multiplied a plurality of times. In this embodiment, the multiplication is carried out three times. A high-frequency component wave is gained from a wave on which such time series filtering has been performed. FIG. 55 illustrates an amplified component wave obtained at a center frequency of 680 kHz reached after gradual sweeping of center frequencies towards higher frequencies. A wave 801, having a large amplitude, on the leftmost is a reflected wave from the upper end of the reinforcing bar. The position indicated by the cursor is its time of generation.

The cursor to the right indicates the position of generation of a reflected wave that transmits through a go path 701 in the form of a longitudinal wave and through a return path 702 in the form of a transverse wave. In addition, the cursor further to the right indicates the position of generation of a reflected wave that allows a trace amount of transverse wave transmitted from the transducer to transmit through the paths 701 and 702 in the form of a transverse wave. It should be noted that a reflected wave 805 with a trace amplitude is generated at this position.

Designated as 802 is a reflected wave 76, from the lower end of the reinforcing bar shown in FIG. 19(c), which transmits through the go and return paths within the concrete in the form of a longitudinal wave and through the reinforcing bar also in the form of a longitudinal wave.

Designated as 803 is a wave which transmits through the reinforcing bar on the circumference of the reinforcing bar of FIG. 20(a) in the form of a longitudinal wave and through the go path 701 and the return path 702 within the concrete also in the form of a longitudinal wave.

Designated as 804 is a two-wave-superimposed wave which transmits through the reinforcing bar of FIG. 20(a) on the circumference thereof in the form of a transverse wave and within the concrete in the form of a transverse wave, and which transmits through the go and return paths 701 and 702 and within the concrete in the form of a longitudinal wave. Furthermore, designated as 806 is the generation of a very special wave. The longitudinal wave input into the concrete from the transmitting transducer is subjected to a mode conversion at the interface between the concrete and a number of fine stones and gaps within the concrete. The superimposed transverse wave produced through this conversion is reflected on the upper end of the reinforcing bar and transmits through both the paths 701 and 702 in the form of a transverse wave.

From the foregoing, letting $t_2$ be the time of generation of the wave 801, $t_1$ be the time of generation of the waves 802, 803, 804, 805, and $V_P$ be the longitudinal-wave sound velocity of the ultrasonic waves in the iron material, the diameter d of the reinforcing bar is calculated in accordance with the following equation 71 using the waves 801 and 802.

$$d = \frac{(t_1 - t_2) \times V_P}{2} \quad (71)$$

The diameter d of the reinforcing bar is calculated in accordance with the equation 17 using the waves 801 and 803.

The diameter d of the reinforcing bar is calculated in accordance with the following equation 72 using the waves 801 and 804.

$$d = \frac{(t_1 - t_2) \times V_S}{\pi} \quad (72)$$

where $V_S = 0.53 V_P$.

Incidentally, suppose the wave 804 can be separated into two waves by gaininig a high-frequency component wave. In this case, of these two waves, letting $t_1$ be the time of generation of the wave that is produced earlier in time, the diameter of the reinforcing bar can be calculated in accordance with the aforementioned equation 72, and letting $t_1$ be the time of generation of the wave that is produced later in time, the diameter of the reinforcing bar can be calculated in accordance with the following equation 73.

$$d = \frac{(t_1 - t_2) \times {_c}V_S}{\pi} \quad (73)$$

where ${_c}V_s$ is the velocity of a transverse wave of the reflected wave within the concrete and determined to be 0.59 to 0.62 of the longitudinal wave ${_c}V_p$. From the foregoing, 801 and 802 give the diameter of the reinforcing bar d=(50.9−44.5)5.9/2=18.9 mm, 801 and 803 give d=(54.5−44.5)5.9/π=18.8 mm, and 801 and 804 give d=(65−44.5)5.9×0.53/π=20.4 mm, all of which allow the actual value of 19 mm to be measured with extremely high accuracy.

Figure 56:
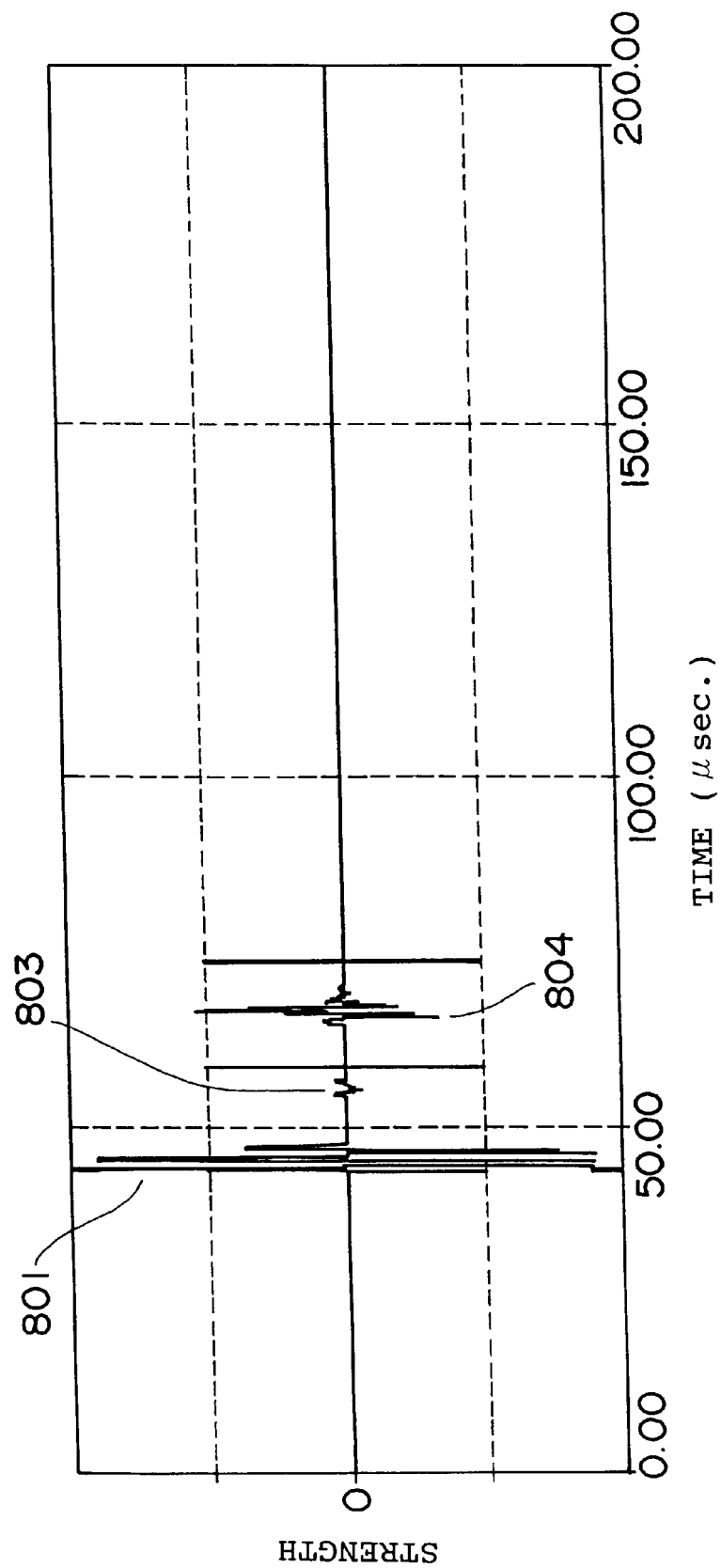
FIG. 56 is a graph illustrating a component wave having a center frequency of 1 MHz.

Furthermore, sweeping in higher frequencies possibly causes the waves 802, 805, 806 to be diminished in amplitude. FIG. 56 illustrates a component wave having a center frequency of 1 MHz.

Incidentally, FIGS. 55 and 56 illustrate a component wave raised to the third power.

In the aforementioned embodiment, a component wave having a predetermined center frequency was gained from a received wave by filtering the aforementioned received wave. Though not illustrated, in an ultrasonic detection apparatus with a mechanism having a transmitting transducer for outputting an oscillating ultrasonic wave of the aforementioned predetermined center frequency and a receiving transducer for measuring a received wave, the received ultrasonic wave is generally the same as the component wave gained by filtering in the aforementioned embodiment. By using such an ultrasonic detection apparatus having the aforementioned mechanism, it is possible to obtain, as a received wave, a component wave that is equivalent to the component wave of the aforementioned predetermined center frequency.

Figure 57:
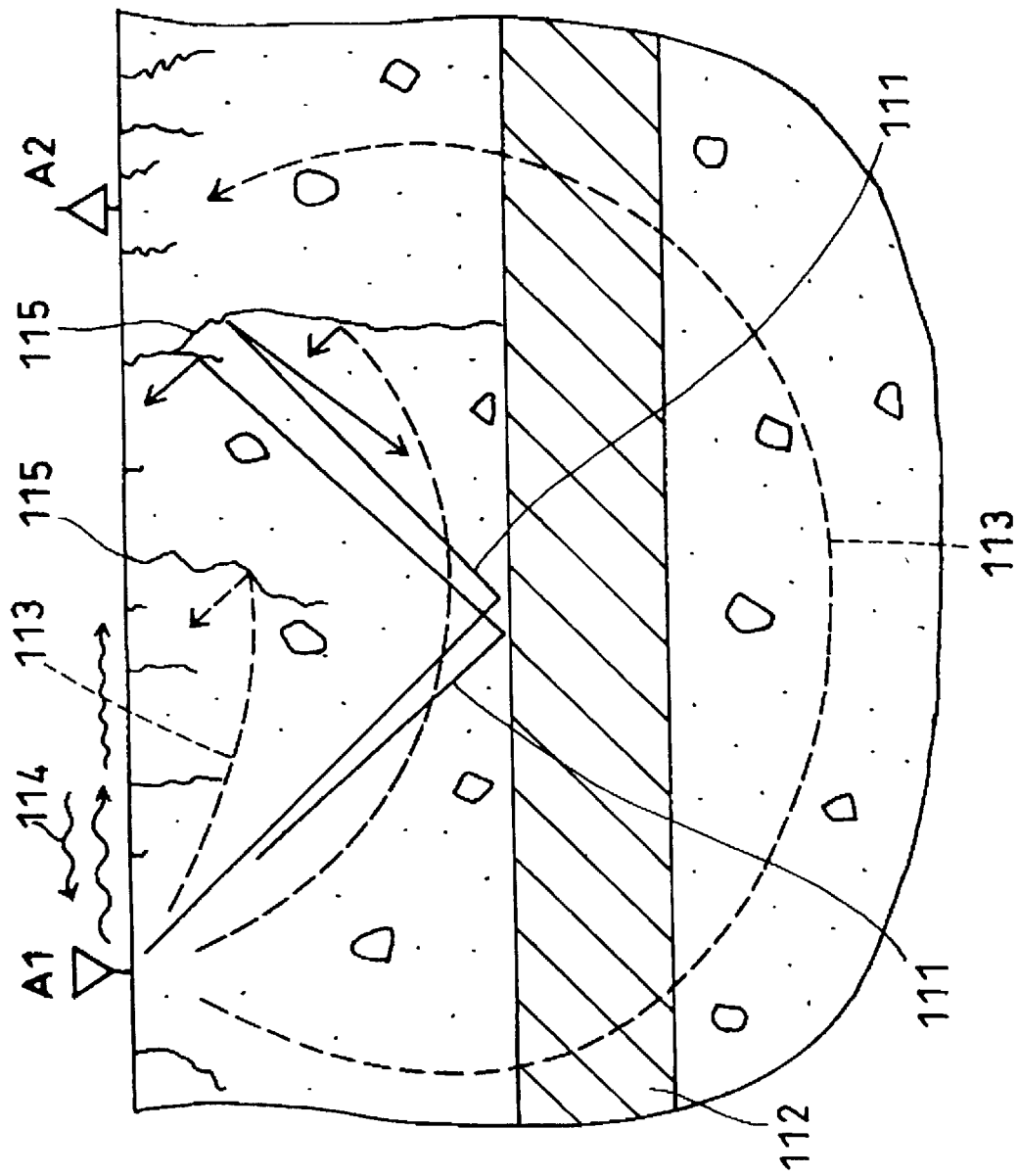
FIG. 57 is a schematic view illustrating the transmission of various waves in a concrete material that has been subjected to aging.

According to the aforementioned measuring method, it is possible to measure the planar position, the thickness of the covering, and the diameter of the reinforcing bar with high accuracy; however, a concrete material that has been subjected to weather damage and aging has a deterioration in physical property of the surface layer and numerous cracks of fine widths even when the surface of the concrete material looks comparatively good. FIG. 57 is a schematic view illustrating the transmission of various waves in a concrete material that has been subjected to aging.

In an attempt to measure the covering thickness and the like of such a concrete material, the transmission of reflected waves 111 and the like from a reinforcing bar 112 being detected is blocked by cracks 115 of a fine width. On the other hand, a larger number of direct waves 113, which transmit through deep paths, are received at reception point A2. Accordingly, by the aforementioned method, it is in some cases possible to detect the planar position of the reinforcing bar but impossible in some other cases. Incidentally, the path of a surface wave 114 to the reception point A2 is also blocked by the crack 115.

Figure 58:
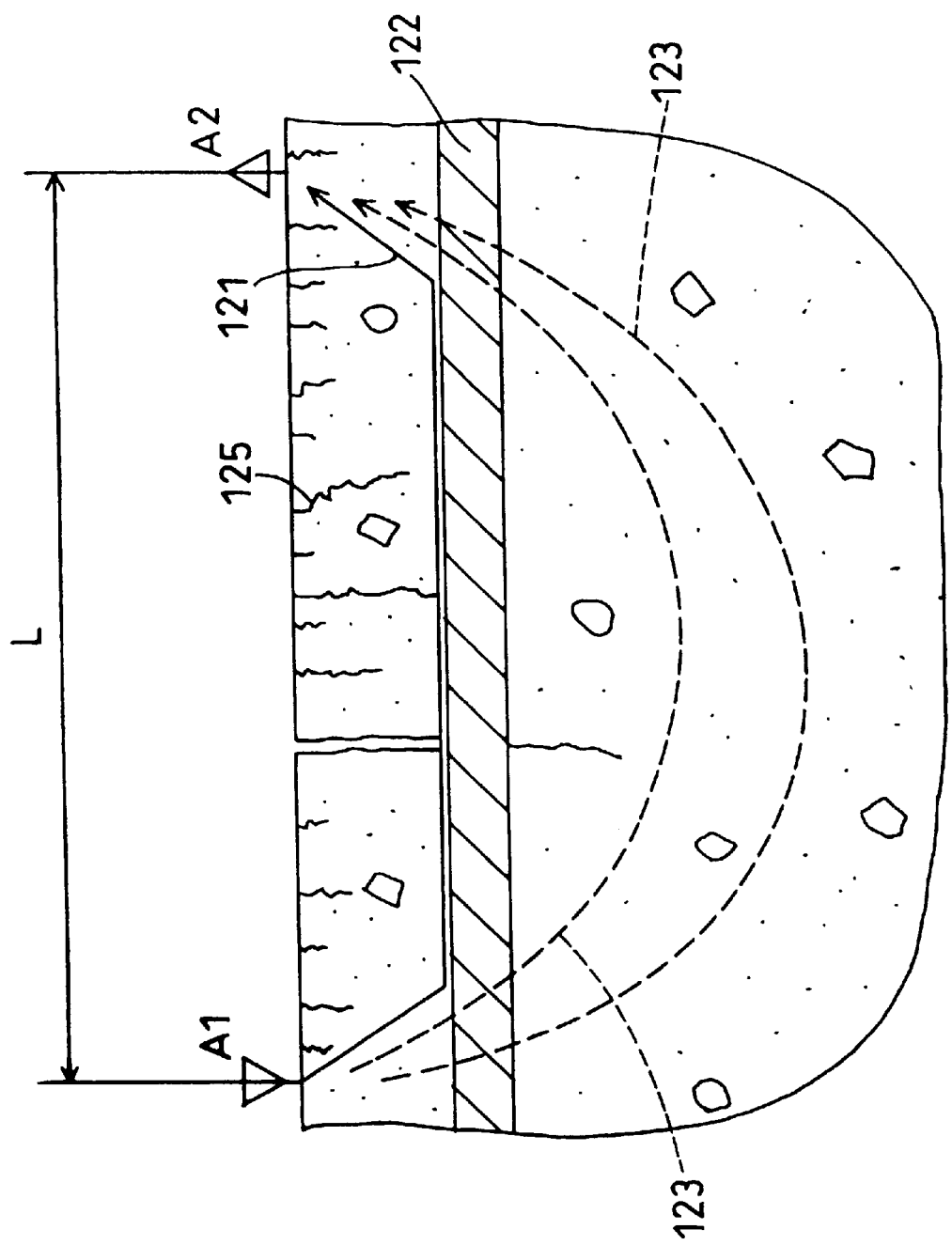
FIG. 58 is a schematic view illustrating the path of critical refracted waves.

Even in such a case, use of the transmission path of an ultrasonic wave of a critical refracted wave that transmits on the surface of the reinforcing bar makes it possible to positively detect the position of the reinforcing bar with an extremely high accuracy. FIG. 58 is a schematic view illustrating the path of critical refracted waves.

As described above, suppose numerous cracks 125 have been produced on the surface. In this case, since the transmission of a reflected wave and the like is blocked by the cracks 125, a wave 121 transmitting as a critical refracted wave via a reinforcing bar 122 and a direct wave 123 through a deep layer of the concrete material transmit as the ultrasonic waves input at transmission point A1 and received at reception point A2.

Here, for the paths for the wave 121 transmitting as a refracted wave and the direct wave 123, the former is shorter than the latter. In addition, the transmission velocity of ultrasonic waves is greater in the reinforcing bar 122 than in the concrete material. Accordingly, at reception point A2, the wave 121 transmitting as a refracted wave is received earlier than the direct wave 123. In addition, the greater the distance between the transmission point Δland the reception point A2, the larger the difference between their reception times becomes.

Incidentally, since the wave 121 transmitting as a refracted wave has an extremely small amplitude, the presence of an extremely low level of electrical noise or a disturbance in measurement environments would cause the wave 121 transmitting as a refracted wave to be buried therein, thereby conventionally making it difficult to detect the wave 121.

In this regard, as the results of intense study made by the inverter of the present invention, it was found that measurements could be made with an extremely high accuracy on a concrete material having cracks formed on the surface thereof. This was accomplished by incorporating an ultrasonic transmitting circuit (the stepped-voltage generator circuit 1a and the stepped-voltage driving circuit 1c) and a receiving circuit (the amplifier circuit 4a) into the transducers, respectively, to electrically separate the circuits from each other, thereby reducing standing or non-standing electrical noise as much as possible. Then, provided was an apparatus for performing arithmetic averaging at extremely high speeds on a received wave to eliminate still remaining non-standing electrical noise and disturbances of high energy and then measurements were made in accordance with the method shown below.

Figure 59:
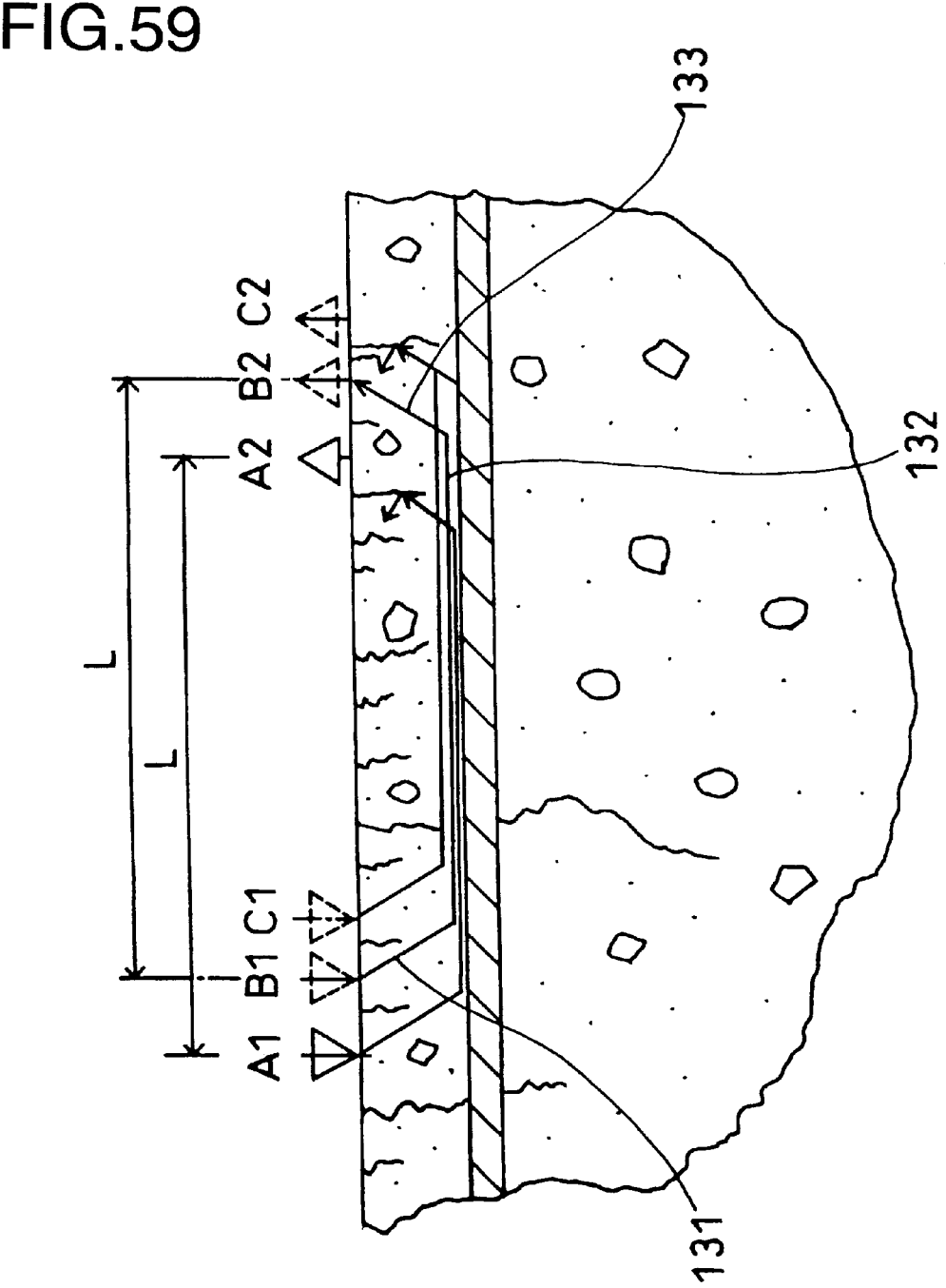
FIG. 59 is a schematic view illustrating a method for detecting a reinforcing bar in a concrete material on the surface of which cracks are formed.

FIG. 59 is a schematic view illustrating a method for detecting a reinforcing bar in a concrete material on the surface of which cracks are formed. First, with the transmitting transducer and the receiving transducer being spaced apart from each other by L, a measurement is made between a transmission point Δland a reception point A2. Δ*t this time, measurements are repeated* 1,000 times to 2,000 times to perform arithmetic averaging or the arithmetic averaging is performed 10,000 times or 20,000 times in some cases. Δit this time, it is not necessary to move the transmitting transducer and the receiving transducer as shown in FIG. 30 to perform the arithmetic averaging of the equation 19 or 20. This is because waves such as the surface wave 114, which interfere with detection, and the direct wave 113 through a shallow path are blocked by the cracks 115. Thereafter, in accordance with the same method, measurements are made between a transmission point B1 and a reception point B2 as well as between a transmission point C1 and a reception point C2. Incidentally, L is the distance between the transmission point B1 and the reception point B2, and between the transmission point C1 and the reception point C2.

According to this method, like a measurement between the transmission point B1 and the reception point B2, a wave of a critical refracted wave may be received without causing the cracks to block the transmission of the waves through paths 131 and 133. Incidentally, the transmission of waves through a path 132 is not blocked irrespective of the presence of a crack deeper in depth than the embedded reinforcing bar. In addition, the transducers are moved in the direction of arrangement of the reinforcing bar being detected.

Figure 60:
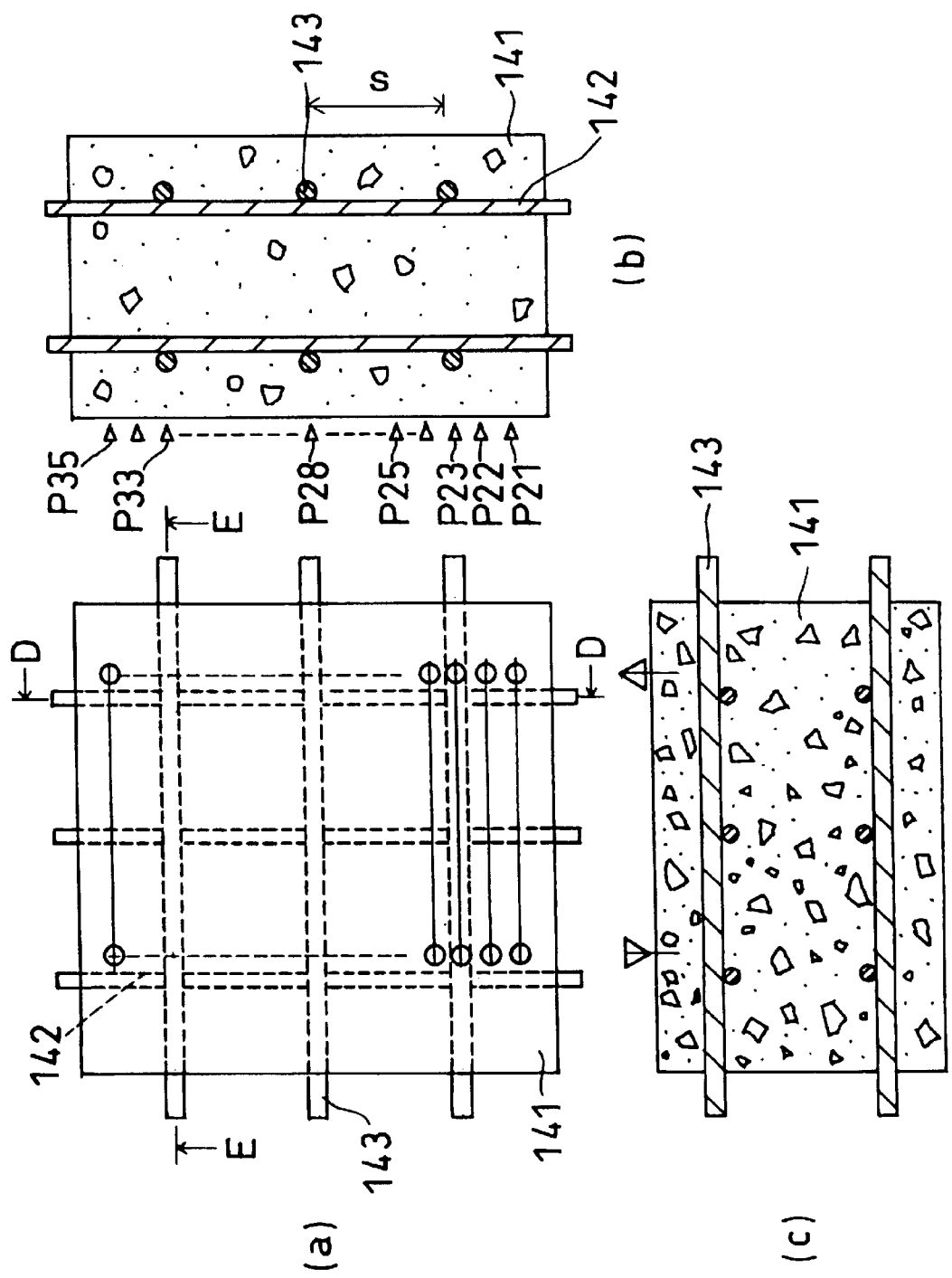
FIG. 60 is a view illustrating a concrete material that has been left for five years dried after poured, (a) being a plan view thereof, (b) being a cross-sectional view taken along line D—D of (a), and (c) being a cross-sectional view taken along E—E of (a).

Now, the results obtained by an actual measurement in accordance with the aforementioned method are explained below. FIG. 60 is a view illustrating a concrete material that has been left for five years dried after poured, (a) being a plan view thereof, (b) being a cross-sectional view taken along line D—D of (a) and (c) being a cross-sectional view taken along E—E of (a0. The dimensions of a concrete material 141 in the vertical and horizontal are each 50 cm, with a thickness of 30 cm. Furthermore, a total of six round reinforcing bars 142, each having a diameter of 19 mm, are embedded at a position of 5 cm from the front and reverse surfaces. Now, at each of measurement positions P21 to P35, letting L be 30 cm, obtained was a received wave after 1,000 times of arithmetic averaging from a measurement with the distance between the transmitting transducer and the receiving transducer being fixed.

FIG. 61 is a view illustrating waves received at the measurement position P28, (a) being a graph illustrating a case where standing or non-standing electrical noise and disturbance has never been eliminated and (b) being a graph illustrating a case where they have been eliminated. That is, FIG. 61(b) illustrates a wave from which electrical noise and disturbance have been eliminated using the aforementioned arithmetic averaging in accordance with the equation 1. Incidentally, as a method for eliminating electrical noise, the stepped-voltage generator circuit 1a and the stepped-voltage driving circuit 1c in the stepped-voltage generator 1 were reduced in size to be placed on-board and then incorporated into the transmitting transducer 2a, while the amplifier circuit 4ain the analyzer 4 was reduced in sized to be placed on-board and then incorporated into the receiving transducer. As shown in FIG. 61(a), suppose that the electrical noise and disturbance have not been eliminated. In this case, although the time indicated by line X—X of the figure is a theoretical time of generation of a wave of a critical refracted wave, it is difficult to determine the time. That is, standing and non-standing electrical noise and non-standing disturbance have been generated, thereby causing the wave of the refracted wave to be buried in these waves.

On the other hand, as shown in FIG. 61(b), suppose that the electrical noise and disturbance have been eliminated. In this case, various types of noises are eliminated, thereby making it possible to distinctly identify the time of generation of the refracted wave. At this point in time, as a method for eliminating standing and non-standing electrical noise and disturbance, the aforementioned method was employed for separating a hardware circuit in the ultrasonic transmitter and receiving circuits to perform the arithmetic averaging 2,000 times in accordance with the equation 1.

Figure 62:
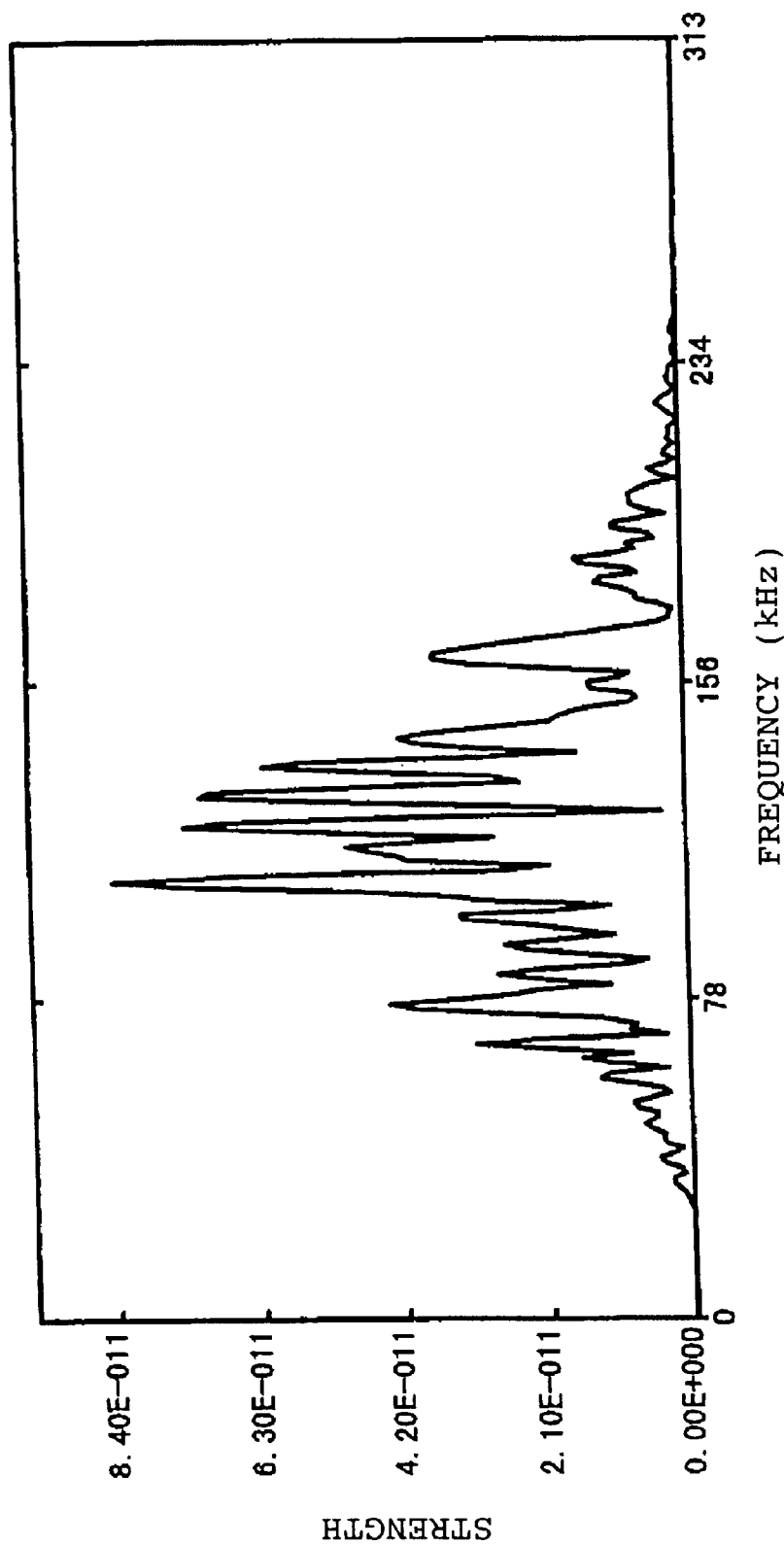
FIG. 62 is a graph illustrating a Fourier spectrum with the center frequency being at 120 kHz.

Incidentally, the time series waves of FIGS. 61(a) and (b) are gained at a center frequency of 120 kHz. FIG. 62 is a graph illustrating a Fourier spectrum with the center frequency being at 120 kHz. In addition, time 103.9 μs, which is indicated by the dashed lines in FIGS. 61(a) and (b) is the time for transmitting ultrasonic waves.

In the detection of a reinforcing bar 143 shown in FIG. 60, the angle of incidence of ultrasonic waves is found to be 42° by applying the sound velocity in the concrete model $_cV_p$=3950 m/s and the sound velocity in the reinforcing bar $_gV_p$=5900 m/s to equation 77, described later, which is derived from the Snell's law. Thus, the transmission length is 67.3 mm×2 in the concrete material 141 and 210 mm in the reinforcing bar 143. Therefore, a theoretical time of reception $t_k$ is expressed by the following equation 74.

$$t_k = \frac{67.3 \times 2}{3.95} + \frac{210}{5.9} = 69.6 \text{ (μs)} \tag{74}$$

This matches almost to a measured value 68.3 (μs) determined from 172.2–103.9.

Figure 63:
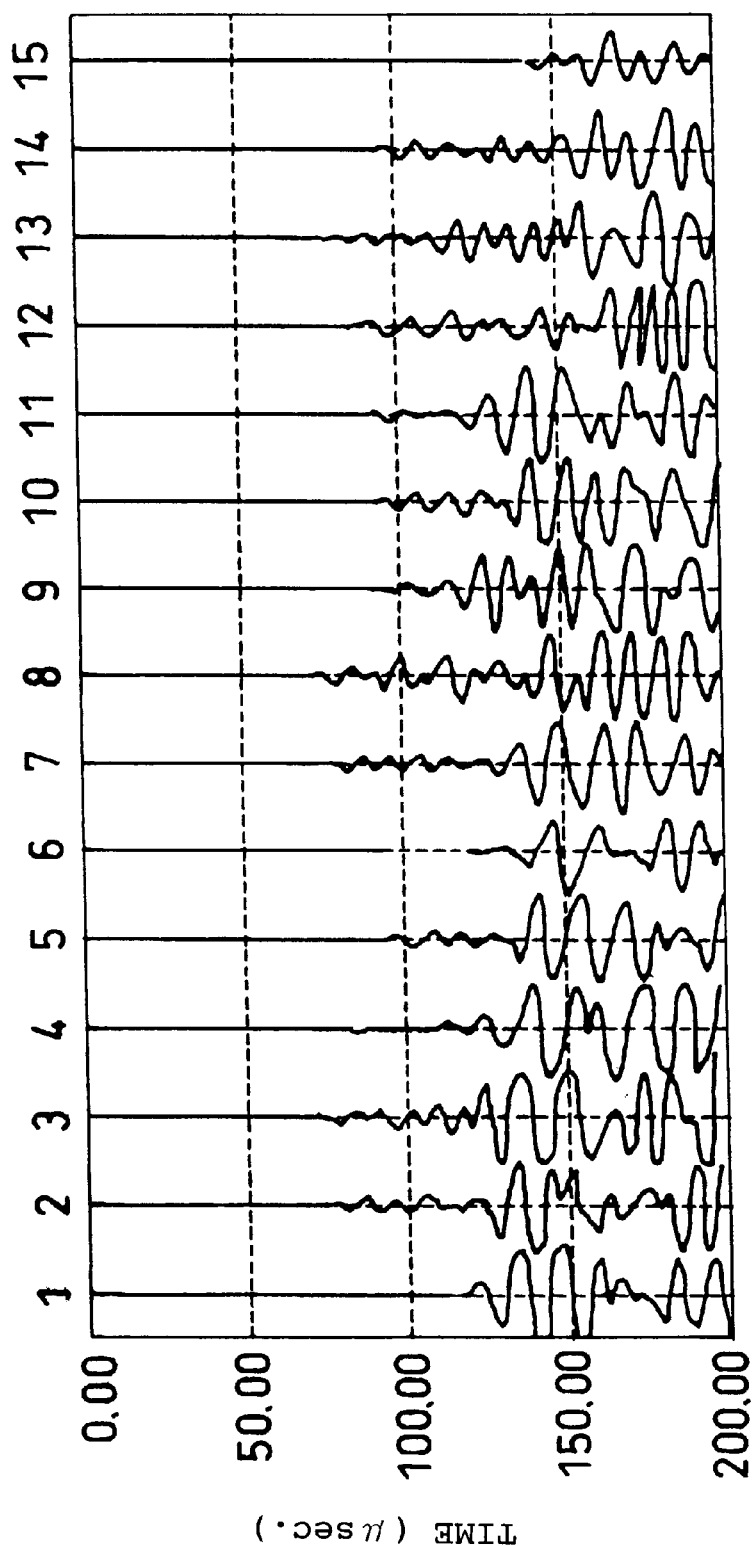
FIG. 63 is a schematic view illustrating a time series wave obtained at each measurement position when electrical noise or the like has been eliminated.
Figure 64:
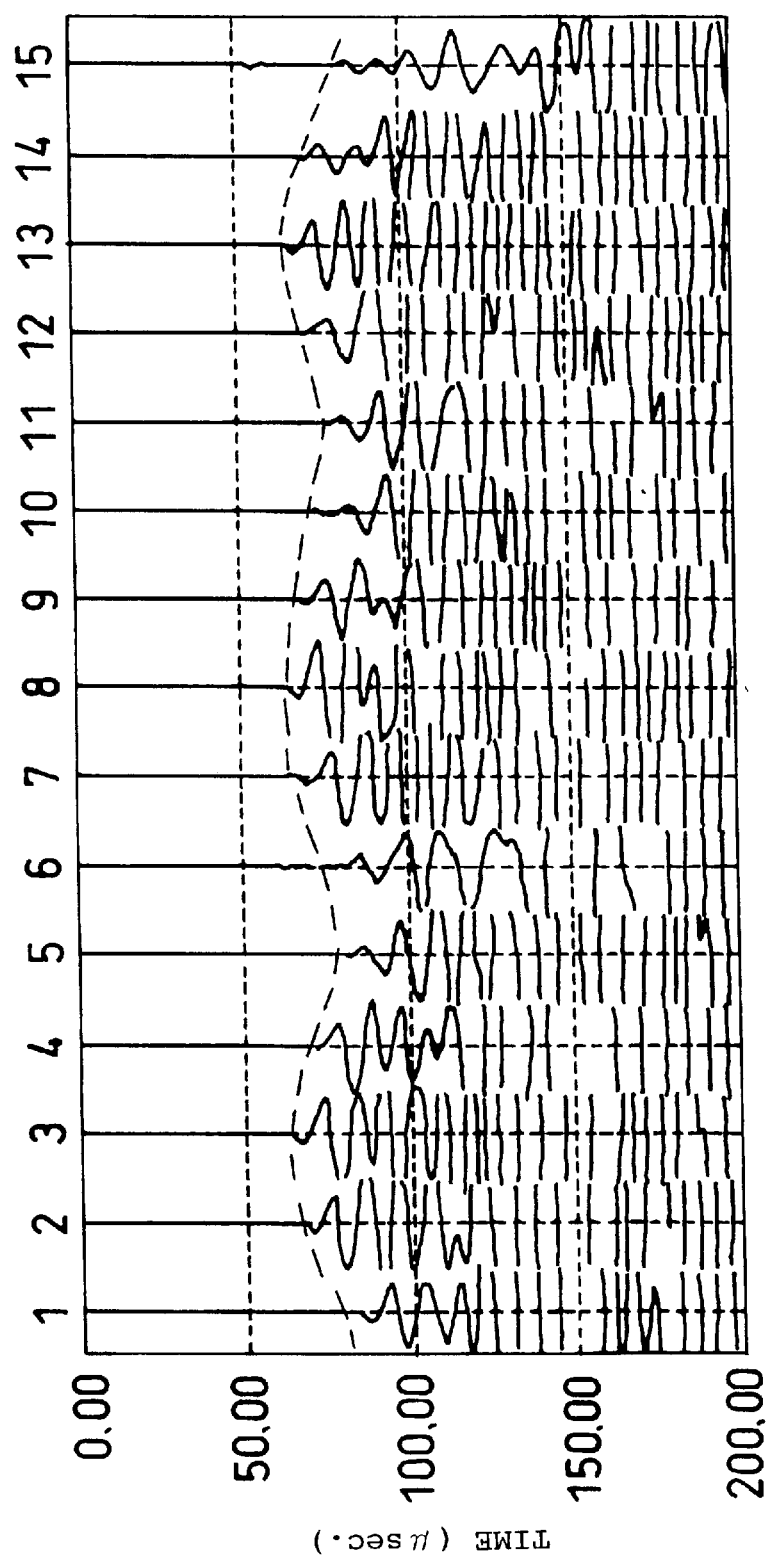
FIG. 64 is a schematic view also illustrating a time series wave obtained at each measurement position when electrical noise and the like have been eliminated, with the scale of FIG. 63 being changed.

FIGS. 63 and 64 are schematic views illustrating time series waves obtained at each measurement position when electrical noise and the like have been eliminated. Incidentally, FIG. 64 illustrates the waves with amplitude being made ten times as large as that of FIG. 63. As shown in FIG. 63, at each measurement position, waves having a small amplitude are generated prior to waves having a large amplitude indicative of direct waves. The waves having a small amplitude are derived from waves of a critical refracted wave via the reinforcing bar 143. In addition, referring to FIG. 64, the waves of a critical refracted wave are generated the earliest in time at the positions P23, P28, and P33, which are located immediately above the reinforcing bar. Furthermore, the waves have maximum amplitudes. Then, at positions farther away from these positions, generation times are delayed and amplitudes are diminished. In the figure, the time of generation of each wave is connected to that of another by a dotted line. A reinforcing bar is embedded at a measurement position where this dotted curve takes on a maximum value. In addition, the covering thickness d can also be calculated by replacing the time of generation $t_k$ at the position of the aforementioned maximum value with $t_{11}$, which is in turn applied to the equation 80, described later.

As described above, electrical noise and serious disturbances such as traffic noise in measurement environments are eliminated as well as two transducers are evenly spaced apart in parallel to the direction of arrangement of reinforcing bars to make measurements and perform arithmetic averaging. It is thereby made possible to detect the reinforcing bar even in a concrete material having cracks formed on the surface thereof. Incidentally, it is necessary to provide the following software for the ultrasonic detection apparatus.

Figure 67:
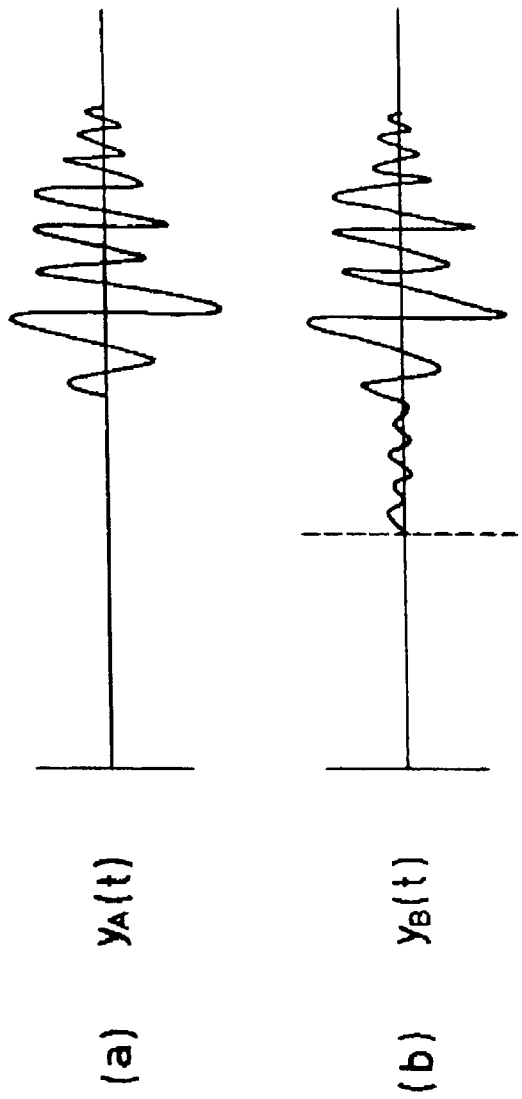
FIG. 67(a) is a schematic view illustrating an arithmetic mean wave $y_A(t)$ and (b) is a schematic view illustrating an arithmetic mean wave $y_B(t)$.
Figure 68:
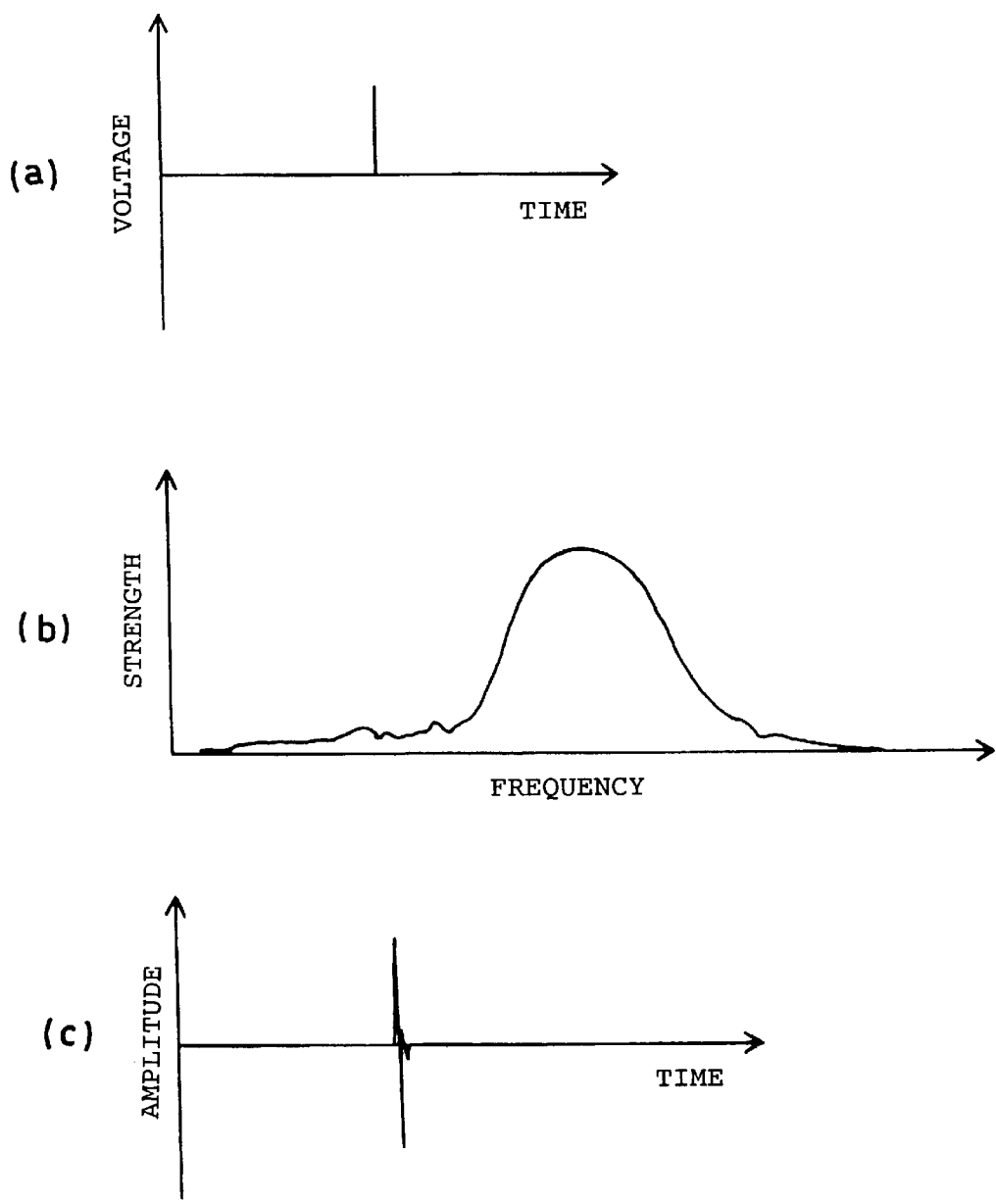
FIG. 68(a) is a graph showing a pulsed voltage, (b) being a graph showing the spectrum of the pulsed voltage, and (c) being a graph showing a time series waveform of the pulsed voltage.
Figure 70:
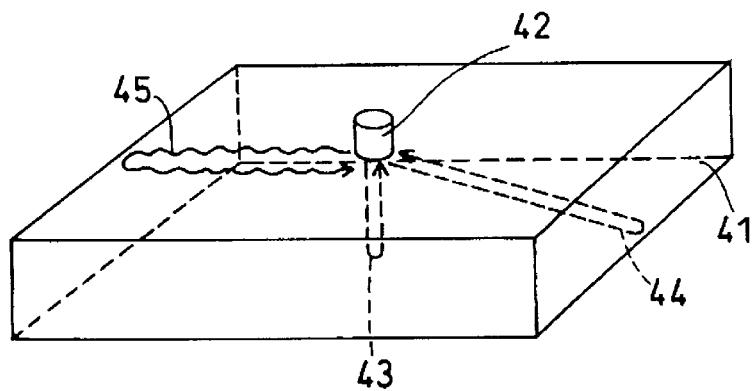
FIG. 70 is a schematic view illustrating a concrete plate as a material to be detected.
Figure 71:
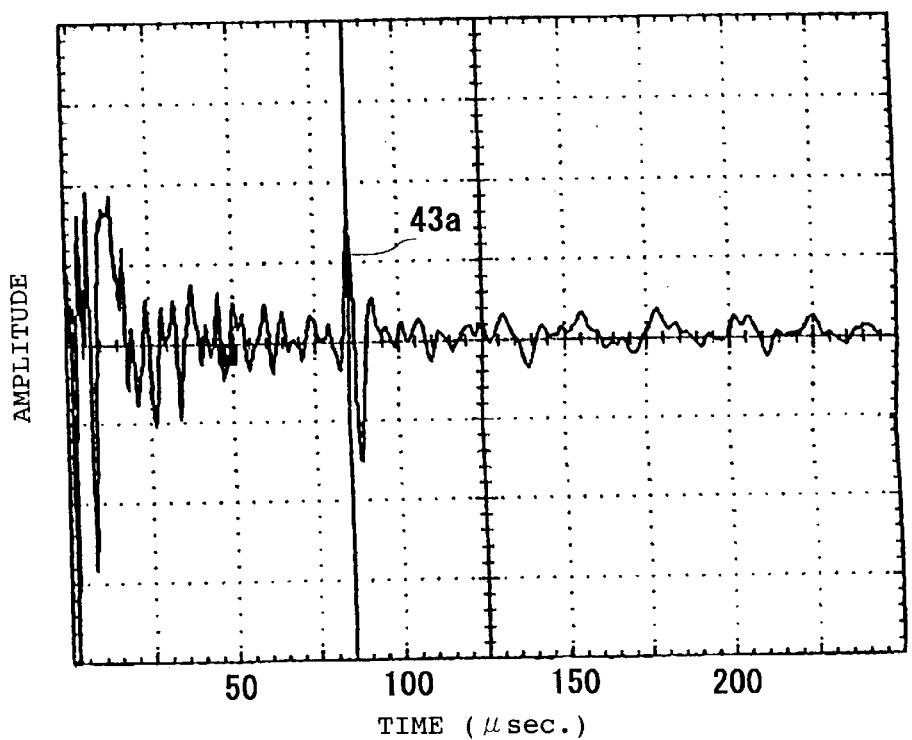
FIG. 71 is a graph illustrating a reflected wave obtained under a prior-art measuring method.
Figure 73:
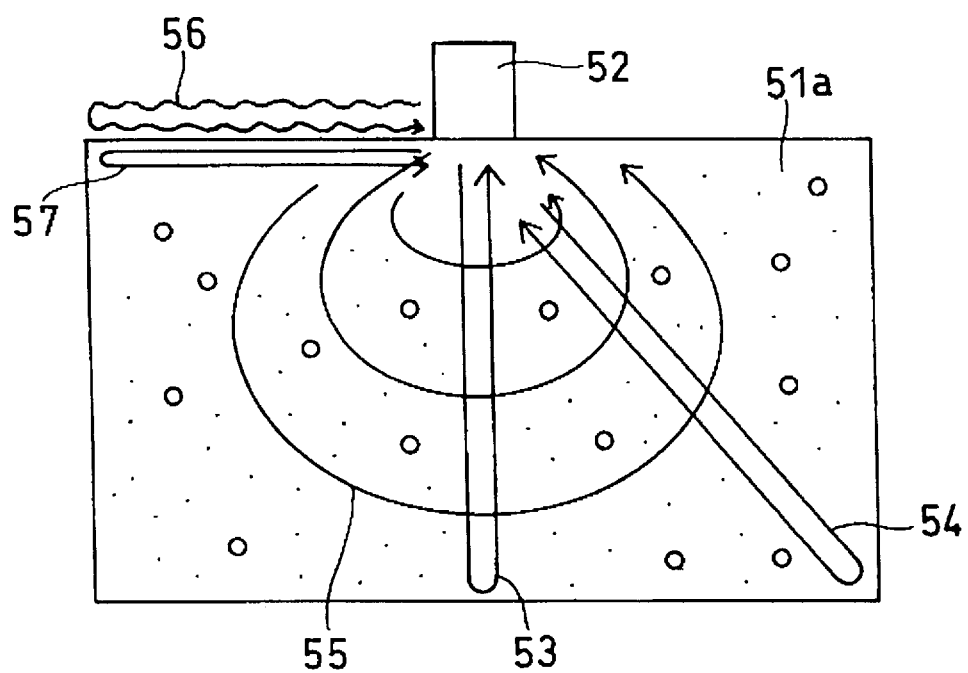
FIG. 73 is a schematic view illustrating the transmission of a wave produced when a transducer 52 is placed at center A for measurement of thickness.
Figure 74:
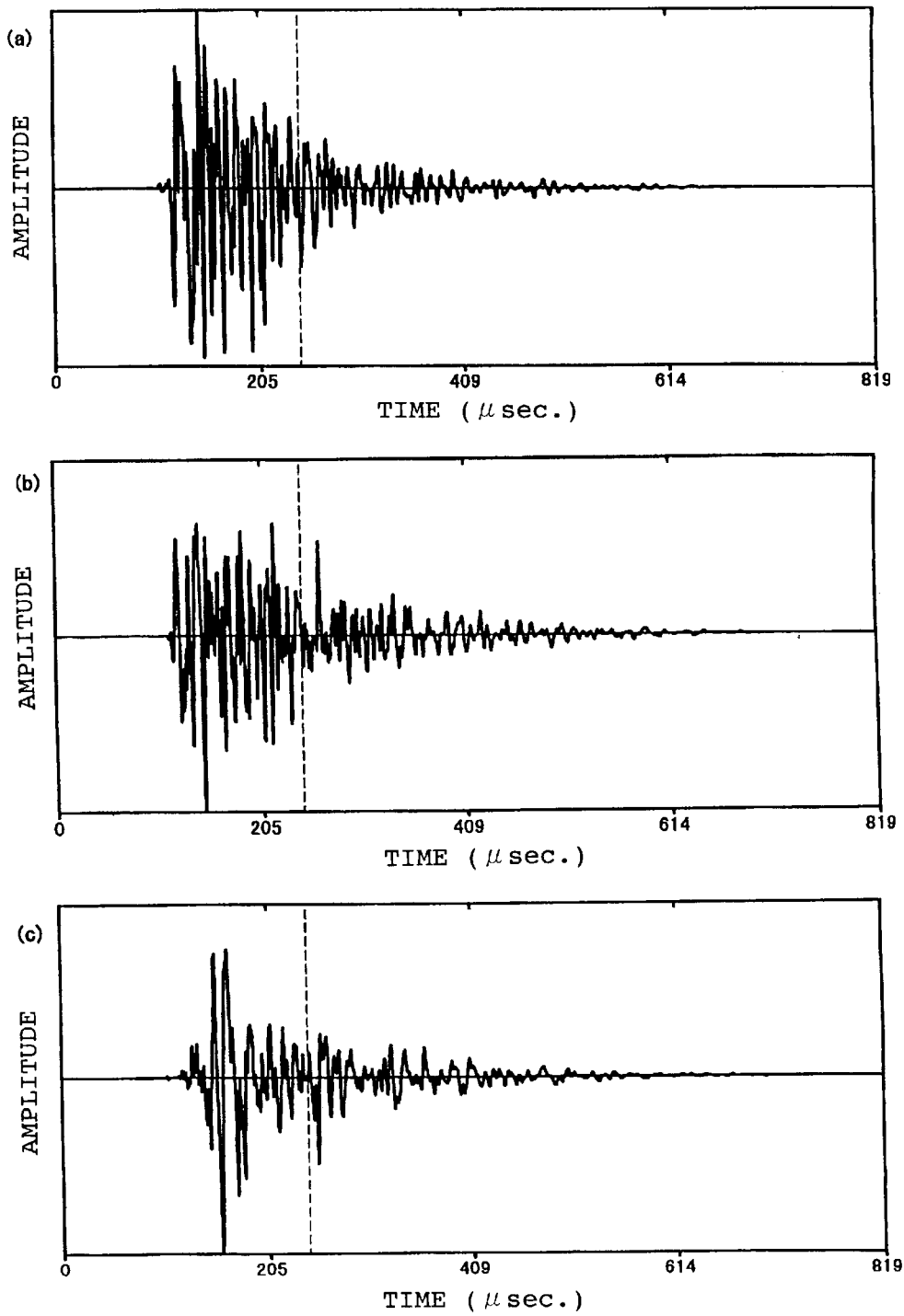
FIG. 74(a) through (c) are graphs illustrating time series waveforms resulted from a prior-art detection method.

Now, the contents of the software are described. Here, let $y_A(t)$ be the arithmetic mean wave obtained according to the equation 1 from the measurement at A1–A2 of FIG. 59 and $y_B(t)$ be the arithmetic mean wave obtained according to the equation 1 from the measurement at B1–B2. FIG. 67(a) is a schematic view illustrating the arithmetic mean wave $y_A(t)$ and (b) is a schematic view illustrating the arithmetic mean wave $y_B(t)$.

As shown in FIG. 67(a), in the arithmetic mean wave $y_A(t)$, the wave 121 of a critical refracted wave via reinforcing bars is blocked by the cracks 125 and the like and thereby only the direct wave 123 is received. In contrast, as shown in FIG. 67(b), in the arithmetic mean wave $y_B(t)$, absence of cracks for blocking the wave 121 would cause the wave 121 of a critical refracted wave, having an extremely small amplitude, to be produced prior to the generation of the direct wave 123. At this time, the time indicated by the dotted line of FIG. 57(b) shows the time of generation of the wave 121 of a critical refracted wave. In addition, the aforementioned software takes, as a received wave, the arithmetic mean wave that has the time, indicated by the dotted line, produced the earliest when measurements are repeated at A1–A2, B1–B2, C1–C2, and so on.

As shown in FIGS. 63 and 64, such measurements made at each measurement position would make it possible to positively identify the generation of waves passing on reinforcing bars as critical refracted waves.

Incidentally, as the distance L becomes larger between the aforementioned transmitting transducer and the receiving transducer, the difference between the dotted curves, shown in FIG. 64, of a maximum and a minimum value becomes larger, thereby facilitating it to identify the position of a maximum value, or in other words, the planar position of presence of the reinforcing bars.

This tells that the value of L preferably has a large value to some extent. However, the value of L is limited. Too large a value of L would cause the aforementioned wave transmitting in the form of a critical refracted wave on the reinforcing bar to be reduced in strength, thereby making it difficult to read the time of generation of the waves of FIGS. 63 and 64 to be received by a receiver. It was determined, based on a number of measurements, that the value of L might be defined by the following equation 75.

$$L \approx 300 \sim 500 \text{ (mm)} \tag{75}$$

Incidentally, the aforementioned detection method employing a critical refracted wave can also be applied to the concrete having no cracks on the surface thereof. However, at this time, it should be understood that the value of L is defined by the following equation 76.

$$\left(1 - \frac{_cV_P}{5.9}\right) \times L > 2 \times \left(\frac{1}{\cos\theta} - \frac{_cV_P}{5.9}\tan\theta\right) \times \tilde{d} \tag{76}$$

where θ can be determined by the equation 79, described later. In addition, numerical value 5.9 in the equation shows the longitudinal-wave sound velocity (μm/μs) in a reinforcing bar. Furthermore, d is an expectation value of the depth of an embedded reinforcing bar.

That is, this is applicable under the condition that, when a longitudinal wave is input from the transmitting transducer immediately downwards, the time $L/_cV_p$ for a feeble longitudinal wave produced on the surface of the concrete to reach the receiver is greater than the $t_{11}$, to be calculated in accordance with equation 80 to be described later, indicative of the time of generation of a wave transmitting on a reinforcing bar in the form of a critical refracted wave.

Figure 65:
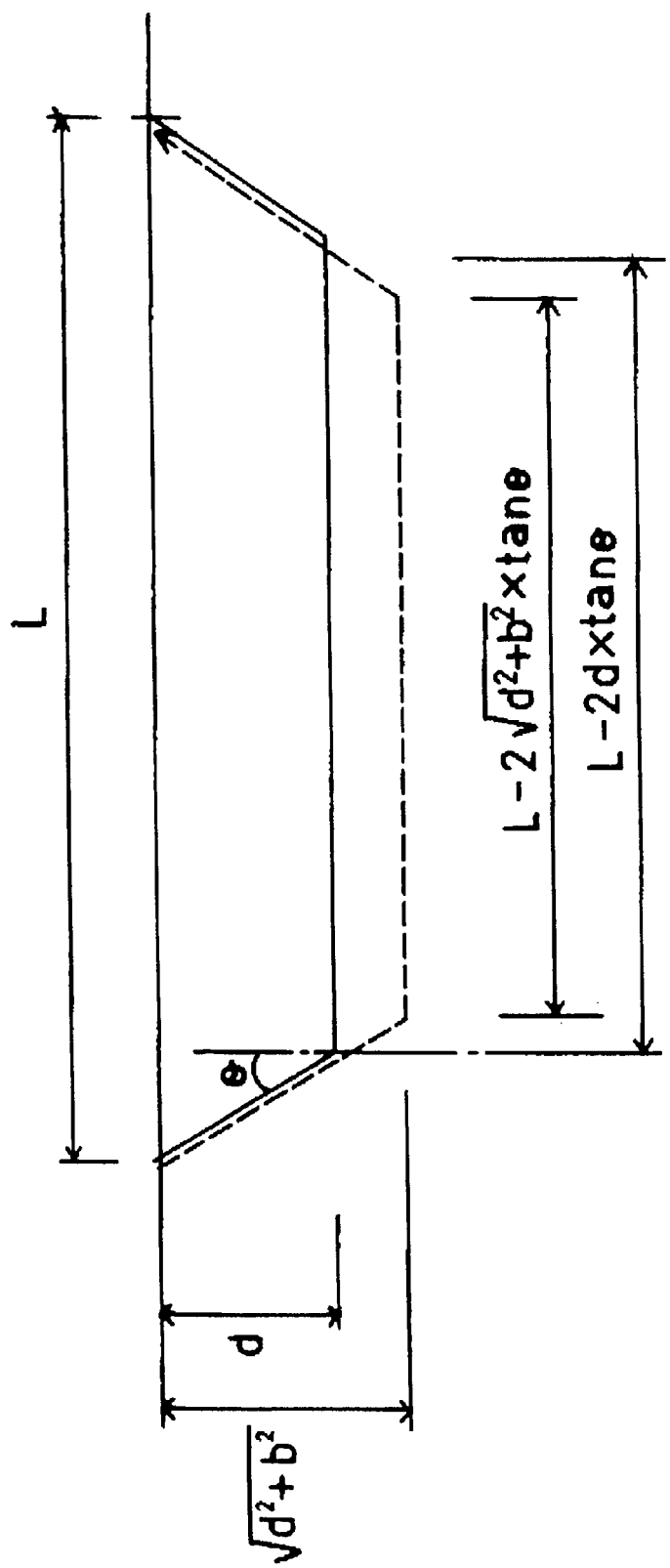
FIG. 65 is a schematic view illustrating the transmission path of refracted waves at measurement positions P23 and P25.

The transmission velocity of ultrasonic waves in a concrete material is assumed to be known in conventional detection methods, however, it is not possible in some cases to measure the transmission velocity beforehand depending on the concrete structure especially when the concrete material has significantly deteriorated. However, from the results shown in FIGS. 63 and 64, it is possible to calculate not only the planar position of presence and the depth of an embedded reinforcing bar but also the transmission velocity of ultrasonic waves in the concrete material. Now, this calculation method is explained below. FIG. 65 is a schematic view illustrating the transmission path of refracted waves at measurement positions P23 and P25. In FIG. 65, the transmission path at the measurement position P23 is indicated by a solid line, while the transmission path at the measurement position P25 is indicated by a dashed line. In addition, d is the covering thickness of the reinforcing bar and b is the distance between the measurement position P23 and the measurement position P25.

As shown in FIG. 65, the length of the reinforcing bar path at the measurement position P25 is expressed by the following equation 77, while that at the measurement position P23 is expressed by the following equation 78.

$$L - 2\sqrt{d^2 + b^2} \times \tan\theta \tag{77}$$

$$L - 2d \times \tan\theta \tag{78}$$

On the other hand, the angle of incidence θ can be determined by the following equation 79 in accordance with the Snell's law, where $_sV_p$ is the longitudinal-wave transmission velocity (5.9 mm/μs) in the reinforcing bar and $_cV_p$ is the longitudinal-wave transmission velocity (unknown) in the concrete material.

$$\sin\theta = \frac{_cV_P}{_sV_P} \tag{79}$$

Referring to FIG. 65, the diagonal path is a region for ultrasonic waves to transmit through the concrete material, while the horizontal path is for those to transmit through the reinforcing bar. Accordingly, letting $t_{11}$ be the time of generation of a refracted wave immediately above the reinforcing bar (at the measurement position P23) and $t_{12}$ be the time of generation at b apart from the position in the horizontal direction (at the measurement position P25), the following equations 80 and 81 hold.

$$t_{11} = \frac{2d}{_cV_P} \times \frac{1}{\cos\theta} + \frac{1}{5.9} \times (L - 2d \times \tan\theta) \tag{80}$$

$$t_{12} = \frac{2\sqrt{d^2 + b^2}}{_cV_P} \times \frac{1}{\cos\theta} + \frac{1}{5.9} \times (L - 2\sqrt{d^2 + b^2} \times \tan\theta) \tag{81}$$

In addition, since the times of generation $t_{11}$ and $t_{12}$ are determined with an extremely high accuracy from FIGS. 63 and 64, these values are substituted into the equations 80 and 81 to solve the simultaneous equations, thereby making it possible to calculate the two known quantities or the transmission velocity in the concrete material and the depth of the embedded reinforcing bar. From FIG. 64, since $t_{11}$=172.2−103.9=68.3 (μs), $t_{12}$=182−103.9=78.1 (μs), b=60 (mm), and L=300 (mm), the equations 80 and 81 give that d=49.5 (mm) and $_cV_p$=4.0 (mm/μs). It can be said that the transmission velocity is calculated within 2% error with respect to the actual transmission velocity of ultrasonic waves. As described above, it is possible to determine not only the depth of the embedded reinforcing bar but also the transmission velocity of ultrasonic waves in the concrete material.

Incidentally, the aforementioned value of b may be determined by the following equation 82 using the planar minimum distance (the value of S in FIG. 60(*b*)) between the position at which the aforementioned $t_{11}$ has been obtained and the reinforcing bar embedded in parallel.

$$b \leq \frac{1}{2}S \tag{82}$$

Industrial Applicability

As described above, according to the present invention, provided is an arithmetic averaging device for performing arithmetic averaging, every time an ultrasonic wave is received, on the ultrasonic wave and the ultrasonic waves that have been received until then, thereby making it possible to gain, by the arithmetic averaging, only such waves that have not been substantially changed in their phase. Accordingly, measurements carried out under the conditions which cause substantially no change in phase of a desired wave would make it possible to detect, with high accuracy, the thickness of a concrete material narrow in width and thick in thickness, the thickness of a reinforcing bar covering, and the diameter thereof, and the depth of cracks. Furthermore, the arithmetic averaging device performs directly the arithmetic averaging, thereby obviating the need for purpose-oriented software and the like and making it possible to perform processing at high speeds.

Furthermore, according to the present invention, while a transmitting transducer for transmitting ultrasonic waves and a receiving transducer for receiving ultrasonic waves are moved within a predetermined region on the surface of the material being detected, transmissions and receptions of ultrasonic waves are carried out a plurality of times to perform arithmetic averaging, every time an ultrasonic wave is received, on the ultrasonic wave and the ultrasonic waves that have been received until then. This makes it possible to vanish unnecessary received waves and thereby gain only the desired received wave. Furthermore, arithmetic averaging is performed on the arithmetic means for each distance between transducers, thereby making it possible to carry out detection with high accuracy even under harsh conditions.

What is claimed is:

1. An ultrasonic detection apparatus, including a receiving transducer configured to receive a plurality of ultrasonic waves transmitted by a transmitting transducer, comprising:

an arithmetic averaging device configured to perform an arithmetic averaging process a plurality of times per one detection, each of said plurality of times performed in response to one of said plurality of ultrasonic waves being received by said receiving-transducer, said arithmetic averaging process includes averaging said one of said plurality of ultrasonic waves and at least one prior received ultrasonic wave of the plurality of ultrasonic waves so as to produce a set of averaged ultrasonic waves; and an extractor configured to extract an extracted ultrasonic wave from said set of averaged ultrasonic waves, said extracted ultrasonic wave having a predetermined frequency as a center frequency, wherein said predetermined frequency is given by ((n± (½)×(10⁶×v/ΔL)(Hz), where ΔL is a variation in a distance between said transmitting transducer and said receiving transducer, v is an ultrasonic wave transmission velocity of a material being detected, and n is a natural number.

2. The ultrasonic detection apparatus according to claim 1, further comprising:

a transducer-distance adjusting device configured to adjust said distance between said transmitting transducer and said receiving transducer by a predetermined value every time a predetermined number of arithmetic averaging operations is performed.

3. The ultrasonic detection apparatus according to claim 2, further comprising:
  a transmitting circuit configured to output an electrical signal to said transmitting transducer;
  a receiving circuit provided in a housing different from one for said transmitting circuit and configured to receive an electrical signal from said receiving transducer; and
  a received-wave determination device connected to said receiving circuit and configured to determine an earliest ultrasonic wave when predetermined ultrasonic waves are included in a plurality of ultrasonic waves received at a measurement point, said earliest ultrasonic wave having the earliest time of generation among said predetermined ultrasonic waves received wave at said measurement point.

4. The ultrasonic detection apparatus according to claim 2, wherein said transducer-distance varying device comprises:
  a plurality of transmitting oscillators evenly spaced apart from said receiving transducer and disposed within said transmitting transducer.

5. The ultrasonic detection apparatus according to claim 2, wherein said transducer-distance adjusting device comprises:
  a plurality of receiving oscillators evenly spaced apart from said transmitting transducer and disposed within said receiving transducer.

6. The ultrasonic detection apparatus according to claim 1, wherein said arithmetic averaging device is configured to perform arithmetic averaging 1,000 times or more per one detection.

7. The ultrasonic detection apparatus according to claim 1, wherein said distance between said transmitting transducer and said receiving transducer is adjustable.

8. An ultrasonic detection apparatus, including a receiving transducer configured to receive a plurality of ultrasonic waves transmitted by a transmitting transducer, comprising:
  an arithmetic averaging device configured to perform an arithmetic averaging process a plurality of times per one detection, each of said plurality of times performed in response to one of said plurality of ultrasonic waves being received by said receiving transducer, said arithmetic averaging process includes averaging said one of said plurality of ultrasonic waves and at least one prior received ultrasonic wave of the plurality of ultrasonic waves, said one of said plurality of ultrasonic waves being formed by applying a step function voltage to an oscillator,
  wherein said predetermined frequency is given by $((n\pm\frac{1}{2})\times(10^6\times v/\Delta L))(Hz)$, where $\Delta L$ is a variation in a distance between said transmitting transducer and said receiving transducer, v is an ultrasonic wave transmission velocity of a material being detected, and n is a natural number.

9. An ultrasonic detection apparatus, including a receiving transducer configured to receive a plurality of ultrasonic waves transmitted by a transmitting transducer, comprising:
  an arithmetic averaging device configured to perform an arithmetic averaging process a plurality of times per one detection, each of said plurality of times performed in response to one of said plurality of ultrasonic waves being received by said receiving transducer, said arithmetic averaging process includes averaging said one of said plurality of ultrasonic waves and at least one prior received ultrasonic wave of the plurality of ultrasonic waves, said one of said plurality of ultrasonic waves being formed by applying a step function voltage to an oscillator; and
  an extractor configured to extract an extracted ultrasonic wave from said set of averaged ultrasonic waves, said extracted ultrasonic wave having a predetermined frequency as a center frequency,
  wherein said predetermined frequency is given by $((n\pm\frac{1}{2})\times(10^6\times v/\Delta L))(Hz)$, where $\Delta L$ is a variation in a distance between said transmitting transducer and said receiving transducer, v is an ultrasonic wave transmission velocity of a material being detected, and n is a natural number.

10. A method for detecting an ultrasonic wave, comprising the steps of:
  transmitting a plurality of ultrasonic waves with a transmitting transducer;
  receiving said plurality of ultrasonic waves with a receiving transducer;
  moving said transmitting transducer and said receiving transducer within a predetermined region on a surface of a material being detected;
  performing arithmetic averaging every time on a received ultrasonic wave and on a plurality of previously received ultrasonic waves so as to produce a set of averaged ultrasonic waves; and
  extracting an extracted ultrasonic wave having a predetermined frequency as a center frequency from said set of averaged ultrasonic waves,
  wherein said predetermined frequency is given by $((n\pm\frac{1}{2})\times(10^6\times v/\Delta L))(Hz)$, where $\Delta L$ is a variation in a distance between said transmitting transducer and said receiving transducer, v is an ultrasonic wave transmission velocity of a material being detected, and n is a natural number.

11. The method for detecting an ultrasonic wave according to claim 10, wherein said moving step comprises:
  moving said receiving transducer within a first region, said first region set to be outside a predetermined transmitting transducer movement region.

12. The method for detecting an ultrasonic wave according to claim 10, wherein said moving step comprises:
  moving said transmitting transducer and said receiving transducer immediately above a target being detected in said material being detected.

13. The method for detecting an ultrasonic wave according to claim 10, wherein said ultrasonic wave is transmitted and received 1,000 times or more.

14. The method for detecting an ultrasonic wave according to claim 10, wherein said transmitting step comprises:
  applying a step function voltage to an oscillator.

15. A method for detecting an ultrasonic wave comprising the steps of:
  transmitting a plurality of ultrasonic waves with a transmitting transducer;
  receiving said plurality of ultrasonic waves with a receiving transducer, said receiving transducer is moved within a predetermined region on a surface of a material being detected;
  performing arithmetic averaging every time on a received ultrasonic wave and on a plurality of previously received ultrasonic waves so as to produce a set of averaged ultrasonic waves; and extracting an ultrasonic wave having a predetermined frequency as a center frequency from said set of averaged ultrasonic waves, wherein said predetermined frequency is given by $((n\pm(1/2))\times(10^6 \times v/\Delta L)(Hz))$, where $\Delta L$ is a variation in a distance between said transmitting transducer and said receiving transducer, v is an ultrasonic wave transmission velocity of a material being detected, and n is a natural number.

16. A method for detecting an ultrasonic wave comprising the steps of: repeating a predetermined number of times the steps of:

transmitting a plurality of ultrasonic waves with a plurality of times a transmitting transducer;

receiving said plurality of ultrasonic waves with a receiving transducer, said receiving transducer within a predetermined region on a surface of a material being detected;

performing arithmetic averaging every time on a received ultrasonic wave and on a plurality of previously received ultrasonic waves so as to produce a set of averaged ultrasonic waves;

varying a distance between said transmitting transducer and said receiving transducer by a predetermined amount;

determining an arithmetic mean of ultrasonic waves obtained as results of said arithmetic averaging; and extracting an ultrasonic wave having a predetermined frequency as a center frequency from said set of averaged ultrasonic waves, wherein said predetermined frequency is given by $((n\pm(1/2))\times(10^6 \times v/\Delta L))(Hz)$, where $\Delta L$ is a variation in a distance between said transmitting transducer and said receiving transducer, v is an ultrasonic wave transmission velocity of a material being detected, and n is a natural number.

17. A method for detecting an ultrasonic wave comprising the steps of iteratively:

transmitting a plurality of ultrasonic waves with a transmitting transducer;

receiving said plurality of ultrasonic waves with a receiving transducer, said receiving transducer within a predetermined region on a surface of a material being detected;

performing arithmetic averaging every time on a received ultrasonic wave and on a plurality of previously received ultrasonic waves so as to produce a set of averaged ultrasonic waves;

extracting an ultrasonic wave having a predetermined frequency as a center frequency from said set of averaged ultrasonic waves; and moving said transmitting transducer and said receiving transducer on a surface of a material being detected, wherein said predetermined frequency is given by $((n\pm(1/2))\times 10^6 \times v/\Delta L))(Hz)$, where $\Delta L$ is a variation in a distance between said transmitting transducer and said receiving transducer, v is an ultrasonic wave transmission velocity of a material being detected, and n is a natural number.

18. The method for detecting an ultrasonic wave according to claim 17, further comprising:

calculating a transmission velocity of an ultrasonic wave in said material being detected in association with a time of generation of a predetermined wave appearing in a result, obtained at a different position, of said arithmetic averaging.

* * * * *